US007511121B2

(12) United States Patent
Arnason et al.

(10) Patent No.: US 7,511,121 B2
(45) Date of Patent: Mar. 31, 2009

(54) POLYMERIC IMMUNOGLOBULIN FUSION PROTEINS THAT TARGET LOW-AFFINITY FCγRECEPTORS

(76) Inventors: Barry G. W. Arnason, 4832 S. Ellis Ave., Chicago, IL (US) 60615; Mark A. Jensen, 3430 N. Lake Shore Dr. #11-M, Chicago, IL (US) 60657; David M. White, 1369 E. Hyde Park Blvd. #504, Chicago, IL (US) 60615

( * ) Notice: Subject to any disclaimer, the term of this patent is extended or adjusted under 35 U.S.C. 154(b) by 263 days.

(21) Appl. No.: 10/096,521

(22) Filed: Mar. 11, 2002

(65) Prior Publication Data

US 2003/0161826 A1    Aug. 28, 2003

Related U.S. Application Data

(60) Provisional application No. 60/274,392, filed on Mar. 9, 2001.

(51) Int. Cl.
    C07K 16/00    (2006.01)
(52) U.S. Cl. .................................................. 530/387.1
(58) Field of Classification Search .............. 530/387.1
    See application file for complete search history.

(56) References Cited

U.S. PATENT DOCUMENTS

| 4,658,019 A | 4/1987 | Kung et al. ................. 530/387 |
| 5,455,165 A | 10/1995 | Capon et al. ............... 435/64.7 |
| 5,714,147 A | 2/1998 | Capon et al. ............. 424/178.1 |
| 5,830,731 A | 11/1998 | Seed et al. ................ 435/172.3 |
| 5,998,166 A | 12/1999 | Luo .......................... 435/69.1 |
| 6,046,310 A | 4/2000 | Queen et al. ............. 530/391.7 |
| 6,165,745 A * | 12/2000 | Ward et al. ................ 435/69.1 |

FOREIGN PATENT DOCUMENTS

| JP | 5-503009 | 5/1993 |
| WO | 91/08298 | 6/1991 |
| WO | WO 92/10591 A1 | 6/1992 |
| WO | WO99/58572 | * 11/1999 |
| WO | WO 99/58572 A1 | 11/1999 |

OTHER PUBLICATIONS

Mikayama et al. PNAS, 1993. 90: 10056-10060.*
Burgess et al J Cell Biol. 111:2129-2138, 1990.*
Lazar et al. Mol Cell Biol. 8:1247-1252, 1988.*
Whisstock et al Quarterly Review of Biophysics, 2003, 36, pp. 307-340.*
Ngo et al, The Protein Folding Problem and Tertiary Structure Prediction, 1994. (ed.), Birkhauser, Boston, MA, pp. 433 and 492-495.*
Wang et al. JBC, 2001 276:49213-49220.*
Achiron et al., "Intravenous immunoglobulin treatment in multiple sclerosis. Effect on relapses," *Neurology*, 50:398-402, 1998.
Alcover et al., "A soluble form of the human CD8 alpha chain expressed in the baculovirus system: biochemical characterization and binding to MHC class I," *Mol. Immunol.*, 30:55-67, 1993.
Anegon et al., "Interaction of Fc receptor (CD16) ligands induces transcription of interleukin 2 receptor (CD25) and lymphokine genes and expression of their products in human natural killer cells," *J. Exp. Med.*, 167:452-472, 1988.
Antel et al., "Generation of suppressor cells by aggregated human globulin," *Clin. Exp. Immunol.*, 43:351-356, 1981.
Ashkenazi and Chamow, "Immunoadhesins as research tools and therapeutic agents," *Curr. Opin. Immunol.*, 9:195-200, 1997.
Berger et al., "Immune complex-induced interleukin-6, interleukin-10 and prostaglandin secretion by human monocytes: a network of pro- and anti-inflammatory cytokines dependent on the antigen: antibody ratio," *Eur. J. Immunol.*, 26:1297-1301, 1996.
Berger et al., "Immune complexes are potent inhibitors of interleukin-12 secretion by human monocytes," *Eur. J. Immunol.*, 27:2994-3000, 1997.
Brittenden et al., "Natural Killer Cells and Cancer," *Cancer*, 77:1226-1243, 1996.
Capon et al., "Designing CD4 immunoadhesins for AIDS therapy," *Nature*, 337:525-531, 1989.
Chamow and Ashkenazi, "Immunoadhesins: principles and applications," *Trends Biotechnol.*, 14:52-60, 1996.
Clynes et al., "Uncoupling of immune complex formation and kidney damage in autoimmune glomerulonephritis," *Science*, 279:1052-1054, 1998.
Duncan, et al., "Localization of the binding site for the human high-affinity Fc receptor on IgG," *Nature*, 332:563-564, 1988.
Durandy, et al., "Dysfunctions of pokeweed mitogen-stimulated T and B lymphocyte responses induced by gammaglobulin therapy," *J. Clin. Invest.*, 67, 867-877, 1981.
Edberg and Kimberly, "Cell type-specific glycoforms of Fc gamma RIIIa (CD16): differential ligand binding," *J Immunol*, 159:3849-3857, 1997.
Edberg, et al., "Analysis of FcgammaRII gene polymorphisms in Wegener's granulomatosis," *Exp Clin Immunogenet*, 14:183-195, 1997.
Eilat, et al., "Secretion of a soluble, chimeric gamma delta T-cell receptor-immunoglobulin heterodimer," *Proc Natl Acad Sci U S A*, 89:6871-6875, 1992.
Fazekas, et al., "Randomised placebo-controlled trial of monthly intravenous immunoglobulin therapy in relapsing-remitting multiple sclerosis," *Lancet*, 349:589-593, 1997.
Ferreri, et al., "Release of leukotrienes C4 and B4 and prostaglandin E2 from human monocytes stimulated with aggregated IgG, IgA, and IgE," *J Immunol*, 136:4188-4193, 1986.

(Continued)

*Primary Examiner*—Michail A Belyavskyi
(74) *Attorney, Agent, or Firm*—Wood Herron & Evans LLP

(57) ABSTRACT

The present invention concerns a family of nucleic acids, polypeptides and cloning vectors which direct expression of fusion proteins that can mimic aggregated IgG (AIG) and immune complex function with respect to their interactions with FcγR and which allow for the inclusion and targeting of a second protein domain to cells expressing FcγR. This was accomplished by expressing multiple linear copies of the hinge and CH2 domains (HCH2) of human IgG$_1$ fused to the framework region of human IgG$_1$. Convenient restriction sites allow for the facile introduction of additional amino-terminal domains. Methods for treating patients using fusion proteins are also disclosed. The HCH2 polymers described here represent a new strategy in the design of recombinant proteins for the therapeutic targeting of FcγR in autoimmune disorders.

24 Claims, 7 Drawing Sheets

OTHER PUBLICATIONS

Fortis, et al., "Dual role of TNF-α in NK/LAK cell-mediated lysis of chronically HIV-infected U1 cells. Concomitant enhancement of HIV expression and sensitization of cell-mediated lysis," *Eur. J. Immunol.*, 29:3654-3662, 1999.

Galon, et al., "Affinity of the interaction between Fc gamma receptor type III (Fc gammaRIII) and monomeric human IgG subclasses. Role of Fc gammaRIII glycosylation," *Eur J Immunol*, 27:1928-1932, 1997.

GenBank Accession No. M12824.

GenBank Accession No. V00494.

GenBank Accession No. Z17370.

Gessner, et al., "The IgG Fc receptor family," *Ann. Hematol.*, 76:231-248, 1998.

Goldstein, "Overview of the development of Orthoclone OKT3: monoclonal antibody for therapeutic use in transplantation," *Transplant Proc*, 19: 1-6, 1987.

Gomez-Guerrero, et al., "Administration of IgG Fc fragments prevents glomerular injury in experimental immune complex nephritis," *J. Immunol*, 164: 2092-2101, 2000.

Gray, et al., "The role of transforming growth factor beta in the generation of suppression: an interaction between CD8+ T and NK cells," *J Exp Med*, 180:1937-1942, 1994.

Greenwood et al., "Structural motifs involved in human IgG antibody effector functions," *Eur. J. Immunol.*, 23:1098-1104, 1993.

Harris, et al., "Induction of activation antigens on human natural killer cells mediated through the Fc-gamma receptor," *J. Immunol.*, 143:2401-2406, 1989.

Hayes et al., "Adoptive cellular immunotherapy for the treatment of malignant gliomas," *Crit. Rev. Oncology/Hematology*, 39:31-42, 2001.

Hulett and Hogarth, "Molecular basis for Fc receptor function," *Adv in Immunol.*, 57:1-127, 1994.

Kurosaki, et al., "A subunit common to an IgG Fc receptor and the T-cell receptor mediates assembly through different interactions," *Proc Natl Acad Sci U S A*, 88:3837-3841, 1991.

Lanier, et al., "Co-association of CD3 zeta with a receptor (CD16) for IgG Fc on human natural killer cells," *Nature*, 342:803-805, 1989.

Lanier, et al., "Molecular and functional analysis of human natural killer cell-associated neural cell adhesion molecule (N-CAM/CD56)," *J Immunol*, 146:4421-4426, 1991.

Legge, et al., "Coupling of peripheral tolerance to endogenous interleukin 10 promotes effective modulation of myelin-activated T cells and ameliorates experimental allergic encephalomyelitis," *J. Exp. Med.*, 191:2039-2051, 2000.

Lund, et al. "Human Fc gamma RI and Fc gamma RII interact with distinct but overlapping sites on human IgG," *J. Immunol.*, 147:2657-2662, 1991.

Majeau, et al., "Mechanism of lymphocyte function-associated molecule 3-Ig fusion proteins inhibition of T cell responses. Structure/function analysis in vitro and in human CD2 transgenic mice," *J Immunol*, 152:2753-2767, 1994.

Meyerson, et al., "Functional dissociation of CD8 alpha's Ig homologue and connecting peptide domains," *J. Immunol.*, 156:574-584, 1996.

Miyagi, et al., "Fc portion of intravenous immunoglobulin suppresses the induction of experimental allergic neuritis," *J. Neuroimmunol.*, 78:127-131, 1997.

Moingeon, et al., "CD3 zeta dependence of the CD2 pathway of activation in T lymphocytes and natural killer cells," *Proc Natl Acad Sci U S A*, 89:1492-1496, 1992.

Morgan, et al., "The N-terminal end of the CH2 domain of chimeric human IgG1 anti-HLA-DR is necessary for C1q, Fc gamma RI and Fc gamma RIII binding," *Immunology* 86:319-324, 1995.

Nagler, et al., "Constitutive expression of high affinity interleukin 2 receptors on human CD16-natural killer cells in vivo," *J. Exp. Med.*, 171:1527-1533, 1990.

Ohtsuka, et al., "Decreased production of TGF-beta by lymphocytes from patients with systemic lupus erythematosus," *J Immunol*, 160:2539-2545, 1998.

Passwell, et al., "Increased prostaglandin production by human monocytes after membrane receptor activation," *J Immunol*, 123:115-120, 1979.

Ptak, et al., "Heat-aggregated immunoglobulins increase in vivo immunogenicity of mouse hapten (TNP)-derivatized macrophages by upregulation of interleukin-12 secretion and expression of B7-1 and B7-2 costimulatory molecules," *Scand. J. Immunol*, 51:479-484, 2000.

Raghavan and Bjorkman, "Fc receptors and their interactions with immunoglobulins," *Ann. Rev. Cell. Dev. Biol.*, 12:181-220, 1996.

Rosenstein, et al., "Lymphokine-activated killer cells: lysis of fresh synergic natural killer-resistant murine tumor cells by lymphocytes cultured in interleukin-2," *Cancer Res.*, 44:1946-1953, 1984.

Shields, et al., "High resolution mapping of the binding site on human IgG1 for FcγRI, FcγRII, FcγRIII, and FcRn and design of IgG1 variants with improved binding to the FcγR," *J. Biol. Chem.*, 276:6591-6604, 2001.

Smith and Morrison, "Recombinant polymeric IgG: an approach to engineering more potent antibodies," *Bio/Technology*, 12:683-688, 1994.

Sondermann, et al., "The 3.2-Å crystal structure of the human IgG1 Fc fragment-FcγRIII complex," *Nature*, 406:267-273, 2000.

Sorensen, et al., "Intravenous immunoglobulin G reduces MRI activity in relapsing multiple sclerosis," *Neurology*, 50:1273-1281, 1998.

Traunecker, et al., "Highly efficient neutralization of HIV with recombinant CD4-immunoglobulin molecules," *Nature*, 339:68-70, 1989.

Vivier, et al., "CD2 is functionally linked to the zeta-natural killer receptor complex," *Eur J Immunol*, 21:1077-1080, 1991.

White, et al., "Design and Expression of Polymeric Immunoglobulin Fusion Proteins: A Strategy for Targeting Low-Affinity Fc Receptors," *Protein Expression and Purification*, 21:446-455, 2001.

Wiesenhutter, et al., "IgG aggregates of different sizes stimulate or suppress Ig secretion by human lymphocytes in vitro," *J. Clin. Immunol.*, 4:124-133, 1984.

Greenwood et al., "Engineering multiple-domain forms of the therapeutic antibody CAMPATH-IH: effects on complement lysis," *Therapeutic Immunology*, 1:247-255, 1994.

Scallon et al., "Addition of an extra immunoglobulin domain to two anti-rodent TNF monoclonal antibodies substantially increased their potency," *Molecular Immunology*, 41:73-80, 2004.

Deane et al., "IgG-assisted age-dependent clearance of alzheimer's amyloid beta peptide by the blood-brain barrier neonatal Fc receptor," *J. of Neuroscience*, 25:11495-11503, 2005.

Medesan et al., "Delineation of the amino acid residues involved in transcytosis and catabolism of mouse IgG1," *Journal of Immunology*, 158:211-2217, 1997.

Ober et al., "Exocytosis of IgG as mediated by the receptor, FcRn: an analysis at the single-molecule level," *The National Academy of Sciences of the United States of America*, 101:11076-11081, 2004.

Roopenian et al., The MHC class I-like IgG receptor controls perinatal IgG transport, IgG homeostasis, and fate of IgG-Fc-coupled drugs, *J. of Immunology*, 170:3528-3533, 2003.

Maxwell et al., "Crystal structure of the human leukocyte Fc receptor FcgR11a" Nature Structural Biology, vol. 6, No. 5, pp. 437-442 (May 1999).

Radaev et al., "The Structure of Human Type III Fcg Receptor in Complex with Fc," The Journal of Biological Chemistry, vol. 276, No. 19, pp. 16469-16477 (May 11, 2001).

Sondermann et al., "Crystal structure of the soluble form of the human Fcg-receptor IIb: a new member of the immunoglobulin superfamily at 1.7 A resolution," The EMBO Journal, vol. 18, No. 5, pp. 1095-1103 (1999).

Takai, "Roles of Fc Receptors in Autoimmunity," Nature Reviews Immunology, vol. 2, pp. 580-592 (Aug. 2002).

Woof et al., "Human Antibody-FC Receptor Interactions Illuminated by Crystal Structures," Nature Reviews Immunology, vol. 4, pp. 1-11 (Feb. 2004).

Armour et al., "Recombinant human IgG molecules lacking Fcγ receptor I binding and monocyte triggering activities," Eur.J. Immunol., vol. 29, pp. 2613-2624 (1999).

Japanese Patent and Trademark Office, office action, dated Jan. 11, 2008, 6pp. with English Translation, 8pp.

Dockal et al., "The Three Recombinant Domains of Human Serum Albumin," The Journal of Biological Chemistry, vol. 274, No. 41, pp. 29303-29310 (1999).

PCT/US08/56066, International Search Report and Written Opinion, mailed Oct. 6, 2008, 13 pp.

White et al. Design and expression of polymeric immunoglobulin fusion proteins: a strategy for targeting low-affinity Fcgamma receptors. Protein Expr Purf. (2001), vol. 21, pp. 446-455.

Jensen et al., A novel Fcgamma receptor ligand augments humoral responses by targeting antigen to Fc gamma receptors. Eur. J. Immunol. (2007), vol. 37, pp. 1139-1148.

Heijnen et al., Antigen targeting to myeloid-specific human Fc gamma RI/CD64 triggers enhanced antibody responses in transgenic mice. J. Clin. Invest. (1996), vol. 97, No. 2, pp. 331-338.

Wernersson et al. IgG-mediated enhancement of antibody responses is low in Fc receptor gamma chain-deficient mice and increased in Fc gamma RII-deficient mice. J. Immunol. (1999), vol. 163, pp. 618-622.

Duan et al. Antitumor activities of TEM8-Fc: an engineered antibody-like molecule targeting tumor endothelial marker 8. J. Natl. Cancer Inst. (2007), vol. 99, pp. 1551-1555.

* cited by examiner

POLYMERIC IMMUNOGLOBULIN FUSION PROTEINS THAT TARGET LOW-AFFINITY FCγRECEPTORS

This application claims the benefit of priority to U.S. Provisional Application No. 60/274,392 filed Mar. 9, 2001.

BACKGROUND OF THE INVENTION

A. Field of the Invention

The present invention relates generally to the field of immunology. More specifically, the present invention relates to immune complexes and the expression and use of recombinant proteins containing multiple hinge and CH2 regions of immunoglobulins.

B. Description of Related Art

Immune complexes (IC) exhibit diverse biological activities; some that contribute to disease whereas others ameliorate disease. Deposition of IgG containing IC on tissue surfaces, as for example in glomeruli, can contribute to the pathogenesis of antibody-mediated autoimmune diseases. On the other hand, IC can favorably modulate T- and B-cell activation pathways via binding to Fc receptors expressed on immunocytes. Aggregated IgG (AIG) shares many features and biological activities with IC. Both modulate T-cell suppressor function (Antel et al., 1981; Durandy et al., 1981), cytokine synthesis, IgG secretion, and lymphocyte proliferation (Berger et al., 1997; Wiesenhutter et al., 1984; Ptak et al., 2000).

Monomeric IgG, or the Fc fragment thereof, ameliorates disease progression in animal models of autoimmune disease (Miyagi et al., 1997; Gomez-Guerrero et al., 2000). Monomeric IgG is widely used therapeutically, usually in massive doses, to treat antibody-mediated diseases in man. The protective effect in antibody-mediated diseases may be achieved in part through blockade of FcγRs such that binding of IC to them is impeded (Clynes et al., 1998). IgG administration also favorably affects the course of T-cell mediated autoimmune diseases such as multiple sclerosis (Fazekas et al. 1997; Sorensen et al., 1998; Achiron et al., 1998). Here the basis for benefit is poorly understood though it is postulated to involve the increased production of anti-inflammatory cytokines initiated by binding of IV IgG, or complexes derived therefrom, to FcγR. In both antibody and T-cell mediated processes the mechanisms and consequences of FcγR engagement are fundamental to the understanding and treatment of autoimmune diseases.

Aggregated IgG has been proposed as a treatment for autoimmune diseases of humans. The use of aggregated IgG has been studied as a treatment for multiple sclerosis and other autoimmune diseases. However, aggregated IgG has major limitations. IgG is commonly aggregated by exposure to heat; the resultant aggregates are bound together in a random fashion limiting reproducibility from one preparation to the next. Preparations contain a heterogeneous collection of aggregates of varying size in diverse conformations.

The formation of immunoglobulin fusion proteins is known in the art. For example, U.S. Pat. Nos. 5,714,147 and 5,455,165 disclose novel hybrid immunoglobulin molecules and the expression vectors encoding them. These chimeric molecules are used in improving the circulating plasma half-life of ligand binding molecules, and comprise a lymphocyte homing receptor fused to an immunoglobulin constant region. Homo or hetero-dimers or tetramer hybrid immunoglobulins containing predominantly the heavy and light constant regions of immunoglobulin are used. U.S. Pat. No. 6,046,310 discloses FAS ligand fusion proteins comprising a polypeptide capable of specifically binding an antigen or cell surface marker for use in treatment of autoimmune disorders. The fusion protein preferably comprises IgG2 or IgG4 isotype, and may comprise antibodies with one or more domains, such as the CH2, CH1 or hinge deleted. Majeau et al. (1994) discusses Ig fusion proteins used for the inhibition of T cell responses. These fusion proteins comprise IgG1 and LFA-3. Eilat et al. (1992) disclose a soluble chimeric Ig heterodimer produced by fusing TCR chains to the hinge region, CH2, and CH3 domains of human IgG1.

Immunoglobulin fusion proteins have been employed to express numerous proteins in mammalian and insect cells (Ashkenazi, et al., 1997). Fusion protein platforms can permit the introduction of additional functions, for example, inclusion of the amino-terminal CD8α domain may result in the co-ligation of FcR on lymphocytes to MHC I on antigen presenting cells (Alcover, et al., 1993; Meyerson, et al., 1996).

Other Ig proteins and variants have also been studied for their therapeutic effect on autoimmune diseases, including a recombinant polymeric IgG that mimics the complement activity of IgM (Smith and Morrison, 1994) where the polymeric IgG is formed by the polymerization of $H_2L_2$ subunits. Greenwood et al. (1993) discusses therapeutic potency relative to the structural motifs involving the human IgG antibodies, IgG1, IgG3, and IgG4. U.S. Pat. No. 5,998,166 discloses human FcγR-III variants, which can be used in the therapy and/or diagnosis of autoimmune diseases. U.S. Pat. No. 5,830,731 discloses novel expression vectors in which cell surface antigens cloned according to that invention have diagnostic and therapeutic utility in immune-mediated infections. Cell surface antigens that are used to regulate lymphocyte activation, achieve antigen aggregation in vitro by incubating lymphocytes with immobilized ligands or antibodies or their fragments (WO9942077). However, the aggregated IgG and Fc aggregates have limited reproducibility, containing a random and heterogeneous mixture of protein thereby limiting their effectiveness as therapeutic agents. Other problems include a lack of an ability to target a number of cell types with a single agent and size limitations.

SUMMARY OF THE INVENTION

The present invention provides novel polypeptides that contain varying numbers of FcγR and/or complement binding domains. These polypeptides provide several advantages over other FcγR-binding moieties, including IgG, Fc fragments, IgG fusion proteins, and complexes and/or aggregates thereof. These advantages include: the ability to hone interaction with FcγR's by varying the construct design and protein product and the ability to obtain a precisely defined construct and protein product containing a known number of FcγR binding domains as opposed to the heterogeneous nature and considerable variations between batches when using aggregated IgG (AIG); an increase in the potency compared to AIG; and the ability to target a number of cell types (e.g. NK cells, monocytes, and B cells) with a single agent. Therefore, the invention allows one to design polypeptides that contain multiple FcγR binding sites and mimic aggregated proteins that are capable of moderating disease severity. Using the teachings of this specification according to the invention, one of ordinary skill is able to create a homogeneous protein with a small size range and conformation. One is also able to create soluble fusion proteins to facilitate generation of dose response curves over a range of concentrations.

Some embodiments of the invention relate to polypeptides comprising a first region comprising a protein or portion thereof and a second region comprising more than one copy of at least a portion of an HCH2 region of an IgG. These polypeptides may target to cells expressing FcγR, bind to FcγR, and/or bind complement components. These polypeptides may further comprise an immunoglobulin framework region. In some aspects of the invention, the polypeptides do not comprise an IgG constant region. In some preferred embodiments, the polypeptides may be single chains, dimers, or trimers, when in active form. The preferred size of the polypeptide is between 26 kDa and 1500 kDa or more preferably between 45 kDa and 600 kDa. It is an aspect of the current invention that the polypeptide is soluble in aqueous solution.

Some aspects of the invention comprise adapting the polypeptide to mimic aggregated IgG and immune complex functions in interactions with FcγR. The amino acid sequence is preferably of a mammalian immunoglobulin. In some cases, the polypeptide may comprise at least two immunoglobulin sequences. The immunoglobulin may be of any source, including, but not limited to a human, rodent, cow, goat, sheep, horse, dog, cat, or pig. The immunoglobulin is more preferably a murine or human immunoglobulin. More specifically, the polypeptide may comprise an amino acid sequence of human IgG1, IgG2, IgG3, IgG4, IgD, IgA, IgE, or IgM, and, in some cases an amino acid sequence comprising a sequence of at least two of human IgG1, IgG2, IgG3, IgG4, IgD, IgA, IgE, and IgM. In some cases the polypeptide is adapted to target to cells expressing one or more of FcγR, FcαR, FcεR, FcμR, FcδR, or FcRn under appropriate conditions. In some preferred embodiments, the polypeptide is adapted to bind to at least two of FcγR, FcαR, FcεR, FcμR FcδR, or FcRn.

In some preferred embodiments the first region of the polypeptide comprises at least a portion that comprises a binding site for a moiety in an organism or on a cell. For example, the first region may comprise a sequence from a Fab of an antibody or antibody-like protein, a CD8α, human serum albumin (HSA), or a transporter protein. In some preferred cases where the first region comprises a sequence from a Fab, the Fab is from a human antibody or a humanized antibody. In some preferred embodiments, the moiety in the organism or on the cell is a cell surface marker, with the cell surface marker, in some cases being an antigen. For example, the sequence may bind to a tumor-associated antigen or an antigen indicative of viral infection. In other cases, the binding may be a least a portion of a binding site of a cellular receptor, a receptor ligand, or an adhesion molecule. In some preferred embodiments, the first region of the polypeptide comprises binding sites that bind two separate antigens, or cell surface markers.

The second region of the polypeptide may comprise any number of copies of at least a portion of the HCH2 region, including, but not limited to, 2, 3, 4, 5, 6, 7, 8, 9, 10, 11, 12, 13, 14, 15, 20, and/or 25 or more copies. Further, the invention contemplates any range derivable between any of the above-described integers. An aspect of the current invention comprises making amino acid substitutions that will alter the tendency of the polypeptide to aggregate and/or an altered hinge region, which preserves FcγR and/or complement binding and prevents inter-molecular disulfide bond formation. These substitutions may be made in any manner known to those of skill in the art and described herein.

In some preferred embodiments, the HCH2 region is an HCH2 region from human IgG1. Further, in some preferred embodiments, the HCH2 region comprises at least amino acid residues 233 to 239 of human IgG1 heavy chain (Eu numbering). In some other embodiments, the HCH2 region comprises at least amino acid residues 216 to 340 of human IgG1 heavy chain (Eu numbering), which residues include the entirety of the human IgG1 hinge and CH2 portions. However, as one of ordinary skill in the art will understand in view of the disclosures herein, there are many different precise embodiments of the claimed polypeptides that may be prepared and tested according to the teaching of the invention. It is possible for the individual HCH2 regions to comprise any number of residues selected from the hinge and CH2 regions of an IgG, so long as the requisite activity for the polypeptide is obtained. Therefore, the invention encompasses, and this specification describes, polypeptides wherein the HCH2 regions comprise any one contiguous portion or combination of contiguous portions of any HCH2 of any type, which portions or contiguous portions may be mutated or modified away from a native HCH2 sequence in any manner possible, so long as the polypeptides have an activity as described herein.

A further aspect of the current invention comprises amino acid substitutions in the second region of the polypeptide that will increase the specific binding of the polypeptide for certain subtypes of FcγR and/or decrease the specific binding of the polypeptide for other subtypes of FcγR. Those of skill in the art will be able to prepare, test and use polypeptides comprising such mutations by following the teaching of this description.

It is another aspect of the current invention that a linker operably links the first and second regions of the polypeptide. This linker can be any form of molecule that links the first and second regions by either covalent or non-covalent forces. In particular, the linker can be a peptide or polypeptide of any length that will function in the context of the invention, including 1, 2, 3, 4, 5, 6, 7, 8, 9, 10, 15, 20, 25, 30, 40, 50, or more amino acids, or any number or range of amino acids that will work for the purposes of the invention. Those of ordinary skill in the art will be able to determine and test any number of types and lengths of linkers.

It is an aspect of the current invention that the polypeptide is adapted to treat immune deficiency disorder, dermatomyositis-polymyositis, an infectious disease, autoimmune thyroiditis, interstitial cystitis, prostatitis, an inflammatory disease, an autoimmune disease, an allergic disease, a degenerative disease of the central nervous system, a disease of the platelets, a disease of the blood vessels, inflammatory neuropathy, a traumatic condition, rheumatoid arthritis, lupus, and/or asthma. In preferred embodiments, the polypeptide is adapted to treat an inflammatory disease of the central nervous system such as multiple sclerosis, an inflammatory bowel disease such as Crohn's Disease or ulcerative colitis, autoimmune diseases of the eye such as uveitis or retinitis, an allergic disease such as allergic rhinitis, a degenerative disease of the central nervous system such as Alzheimer's disease or ALS (Lou Gehrig's disease), a disease of the white blood cells such as a lymphoma or a leukemia, a disease of platelets such as Immune Thrombocytopenic Purpura, a disease of the blood vessels such as Kawasaki disease or atheroma, an inflammatory neuropathy such as Guillain Barré Syndrome, and/or a traumatic condition such as a spinal cord injury. The polypeptide may also be adapted to promote apoptosis, necrosis, or lysis or decrease cell division of neoplastic or virally infected cells, or to alter complement binding.

It is a further aspect of the current invention that the polypeptide can target NK cells or that the polypeptide can target NK cells, monocytes, macrophages, dendritic cells, T cells or B cells. Further, the polypeptide may be adapted to induce immune tolerance. The polypeptide may, likewise, be adapted for use as a vaccine or for use as an antigen-presenting vehicle.

Further embodiments of the invention relate to nucleic acids that encode polypeptides according to the invention. These nucleic acids, in some embodiments, encode both the first region comprising a protein or portion thereof and the second region comprising more than one copy of at least a portion of an HCH2 region of an IgG. In other embodiments, the nucleic acids encode only one of the first polypeptide region comprising a protein or portion thereof and the second region comprising more than one copy of at least a portion of an HCH2 region of an IgG. Further, those of ordinary skill will understand that some nucleic acids according to the invention may encode only portions of either of these regions, and will be able to employ such nucleic acids.

In some preferred aspects of the invention, the nucleic acids are expressible. The polypeptides may be expressed in prokaryotic cells or eukaryotic cells or expressed in a cell free system. Preferred cells for expression include, but are not limited to, insect cells and mammalian cells. Preferred mammalian cells include human and rodent cells including murine and CHO cells. The nucleic acid may be expressible as a transgene or expressible in a genetically modified animal, for example a mouse. The polypeptide may be further defined as an immunoglobulin fusion protein.

In certain preferred embodiments, the nucleic acid allows for expression of a polypeptide comprising the first region and the second region as a single active fusion polypeptide, without the need for any additional protein or other components for function. In other embodiments, the nucleic acid will allow for the expression of either of the first region or the second region, or a portion of either region. In cases where only a single region of the polypeptide, or portion thereof, is encoded by the nucleic acid, then those of ordinary skill will know how to express those portions and, if they so desire, assemble and/or process them into fully functional polypeptides according to the invention. Such assembly and/or processing can employ any of the methods described herein or known to those of skill and/or any of the linkers described herein or known to those of skill.

Another aspect of the current invention comprises vectors that comprise a nucleic acid encoding all or part of a polypeptide of the present invention. The vectors may, for example, be cloning or expression vectors. In some cases, these vectors are produced by a method wherein the nucleic acid sequence encoding the second region comprising more than one copy of at least a portion of an HCH2 region of an IgG is inserted into an existing antibody sequence including a monoclonal antibody sequence or the sequence of any expressible protein.

The cloning vectors of the invention may be comprised in any suitable recombinant host cell, as described elsewhere herein or known to those of skill in the art.

In other aspects, the invention relates to methods comprising: obtaining a polypeptide according to the invention, i.e., a polypeptide comprising a first region comprising a protein or portion thereof and a second region comprising more than one copy of at least a portion of an HCH2 region of an IgG; and administering the polypeptide to a cell. In some such methods, the protein or portion thereof is specifically defined as comprising a soluble protein domain, a transporter domain and/or a ligand-binding domain. Additionally, the polypeptide further comprises an immunoglobulin framework region.

The methods of the invention are further defined, in some cases, as methods of treating an organism with the polypeptides of the invention. In many preferred embodiments, the organism is a mammal, for example, but not limited to, a human, rodent, horse, dog, cat, pig, cow, or goat. In some particularly preferred embodiments, the mammal is a human in need of treatment for a disease, condition, or disorder. In terms of rodents, some particularly preferred rodents are mice and rats.

In the methods of the invention the treating of an organism may occur in any manner, including, but not limited to oral treatment, intranasal treatment, or injection. For example, injection may include, but not be limited to, intravenous, intraperitoneal, intramuscular, or subcutaneous injection. Of course, those of skill will understand that there are many routes of treatment possible, and are enabled by this specification to perform them.

The methods of treating an organism will involve treatment with an amount of the polypeptide that is effective to treat the disease, condition, or disorder that the organism has, or is suspected of having, or to bring about a desired physiological effect. In many cases, this amount will be less than the amount of an IgG or aggregated IgG protein used to treat a comparable disease, condition, or disorder or to bring about a comparable desired physiological effect. In some preferred embodiments, the amount of the polypeptide is administered at a concentration of 0.05 to 10 mg/kg body weight, or more preferably 0.2 to 5 mg/kg body weight, or even more preferably 0.5 to 2 mg/kg body weight or 0.5 mg/kg, 0.6 mg/kg, 0.7 mg/kg, 0.8 mg/kg, 0.9 mg/kg, 1.0 mg/kg, 1.2 mg/kg, 1.4 mg/kg, 1.6 mg/kg, 1.8 mg/kg or 2.0 mg/kg. In regard to some conditions, it is preferred that the dosage will be about 0.75 mg/kg body weight. Of course, those of skill in the art will appreciate that it is possible to employ many concentrations in the methods of the present invention, and will be able to adjust and test any number of concentrations in order to find one that achieves the desired result in a given circumstance. For example, if the polypeptides of the invention are administered in combination with one or more other therapeutic agent for a given disease, condition, or disorder, it is possible to achieve a synergistic effect between the other therapeutic agent and the polypeptide, such that less of the polypeptide is needed.

In some specific embodiments, the polypeptides of the invention are used to treat a mammal that has immune deficiency disorder, dermatomyositis-polymyositis, an infectious disease, autoimmune thyroiditis, interstitial cystitis, prostatitis, an inflammatory disease, any autoimmune disease, an allergic disease, a degenerative disease of the central nervous system, a disease of the platelets, a disease of the blood vessels, inflammatory neuropathy, a traumatic condition, rheumatoid arthritis, lupus, and/or asthma. In preferred embodiments, the polypeptide is used to treat an inflammatory disease of the central nervous system such as multiple sclerosis, an inflammatory bowel disease such as Crohn's Disease or ulcerative colitis, autoimmune diseases of the eye such as uveitis or retinitis, an allergic disease such as allergic rhinitis, a degenerative disease of the central nervous system such as Alzheimer's disease or ALS (Lou Gehrig's disease), a disease of the white blood cells such as a lymphoma or a leukemia, a disease of platelets such as Immune Thrombocytopenic Purpura, a disease of the blood vessels such as Kawasaki disease or atheroma, an inflammatory neuropathy such as Guillain Barré Syndrome, and/or a traumatic condition such as a spinal cord injury. The polypeptide may also be used to promote apoptosis, necrosis, or lysis or decrease cell division of neoplastic or virally infected cells, or to alter complement binding.

In some aspects of the invention, the methods of the invention are further defined as methods of altering immunity in a mammal comprising administering a polypeptide of the invention to the mammal.

The invention also relates to methods of killing neoplastic cells comprising treating a neoplastic cell with one or more polypeptides of the invention. In many such cases, the neoplastic cell is a carcinoma cell, tumor, and/or other form of cancer cell. In some preferred embodiments, the treating results in complement-dependent cytotoxicity, antibody-dependent cell-mediated cytotoxicity, or complement-dependent cell-mediated cytotoxicity of the neoplastic cell. In many cases, the neoplastic cell is comprised in an organism, such as, but not limited to, any of the organisms described above and elsewhere in this specification. In some particularly preferred embodiments, the invention relates to methods of using the polypeptides of the invention as described herein to treat a human who has cancer. In other cases, the neoplastic cell is in cell culture.

The methods of the invention may be further defined as a method of killing a virally infected cell comprising treating a virally infected cell with a polypeptide of the invention. In some preferred such cases, the treatment results in complement-dependent cytotoxicity, antibody-dependent cell-mediated cytotoxicity, or complement-dependent cell-mediated cytotoxicity of the virally infected cell. In some embodiments, the virally infected cell is comprised in a mammal, for example, a human or rodent.

While many of the more commercially valuable aspects of the methods of the invention relate to methods of treating organisms, especially humans, who have some form of disease, disorder or condition, there are other reasons for treating animals with the polypeptides of the invention. For example, it is possible to treat a laboratory animal with the polypeptides in order to test whether or not the polypeptides will be useful in treating humans or other animals in a real-life situation.

In other aspects of the methods of the invention one is able to use the polypeptides of the invention to treat cells in cell culture. There is any number of reasons known to those of skill in the art for wanting to treat cells in culture with the polypeptides. For example, one may want to test polypeptides produced according to the methods described herein for any utility for the given specific methods described herein. Also, one may wish to use the polypeptides of the invention to kill neoplastic or virally infected cells in culture or a assay immune cell function in vitro.

The invention also relates to methods of delivering a therapeutic agent to a delivery site in a mammal comprising: providing a polypeptide comprising a first region which targets the delivery site and a second region comprising more than one copy of at least a portion of an HCH2 region of an IgG; and providing the therapeutic agent to the mammal; wherein the therapeutic agent is delivered to the delivery site to treat the mammal. The polypeptides in this aspect of the invention may further comprise an immunoglobulin framework region. The therapeutic agent can be any form of therapeutic agent known to those of skill in the art. For example, the thereaeutic agent, may be a vaccine component, monoclonal antibody, cytokine, interleukin, steroid, interferon, toxin, chemotherapeutic agent, radioisotope, or immunomodulatory agent such as glatiramer acetate and interferon-β. Further, the invention relates to methods of delivering labels to sites in mammals for imaging or other related procedures. These labels may be any form of labeling moiety known to those of skill in the art, including, but not limited to, fluorescent labels, affinity labels, radiolabels, etc.

Further, the invention relates to methods of preparing one or more of an immunological product comprising: immunizing a mammal with an amount of an antigen and a polypeptide comprising a first region comprising more than one copy of at least a portion of an HCH2 region of an IgG; and producing an immunological product in the mammal. In these embodiments of the invention, the polypeptide may be any of the polypeptides described above. Further, the immunological product may comprises at least one T cell, product produced by a T cell, B cell, or antibody produced by a B cell, wherein the product is directed against the antigen. In some cases, the method is a method of obtaining an immunological product for further use, and the immunological product is obtained from the mammal. In other cases, the method is a method of vaccinating or inducing immunity against the antigen in the mammal. In some aspects of these methods of the invention, the first region comprises a portion of or all of an antibody. Further, the first region may be adapted to bind to tumor, a virus, a fungus, a rickettsia, a mycoplasma, a bacterium, a protozoal parasite or a metazoal parasite. Additionally, the first region may be conjugated to a protein or non-protein molecule derived from a tumor, a virus, a fungus, a rickettsia, a mycoplasma, a bacterium, a protozoal parasite, or a metazoal parasite.

In this specification and the claims, the words "a" and "an," when used with the conjunction "comprising," mean "at least one" or "one or more."

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A. Recombinant proteins were separated on 7% SDS-PAGE gels and stained with Coomassie brilliant blue dye to reveal protein. FIG. 3B. Recombinant proteins were transferred to nitrocellulose membrane and stained with antibodies directed against human Fc. Note that the human IgG control and the fusion proteins are recognized by anti-Fc antibody. FIG. 3C. Recombinant proteins were transferred to nitrocellulose membrane and stained with antibodies directed against human CD8α. Note that only the fusion proteins are recognized by anti-CD8α antibody, indicating specific detection of CD8α.

FIG. 7 compares disease scores of mice treated with saline alone to those treated with HSAR4 or HSAR0. Mice injected with HSAR4 displayed less severe acute disease than mice injected with saline alone or with HSAR0.

DESCRIPTION OF ILLUSTRATIVE EMBODIMENTS

Figure 1:
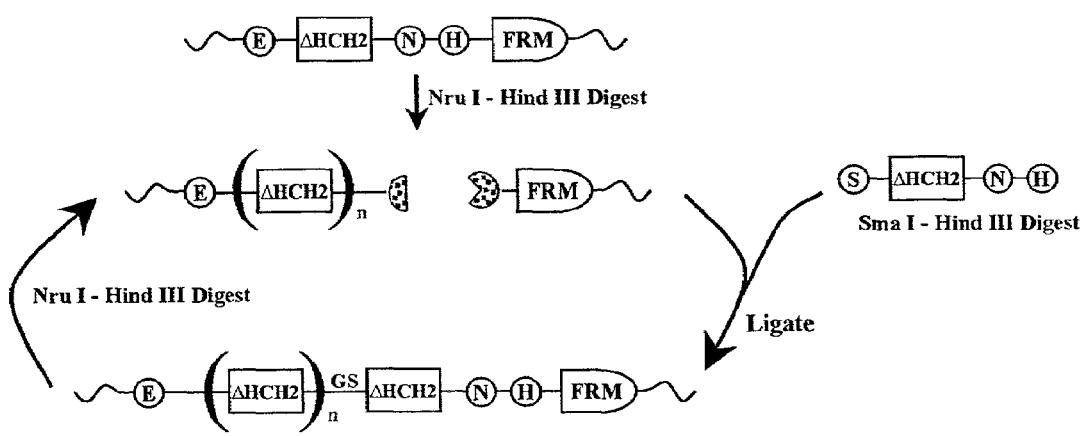
FIG. 1—Schematic depicts the design rationale utilized in the construction of the HCH2 polymer, the key feature of which is the iterative regeneration of cloning sites in the extension step. The ΔHCH2 shown in the schematic represents an HCH2 monomer in which the hinge cysteines have been changed to serines.

This invention describes a family of nucleic acids with a region encoding a polypeptide and the polypeptide encoded by the nucleic acid which can mimic aggregated IgG (AIG) and immune complex function with respect to their interactions with FcγR and which allow for the inclusion and targeting of a second protein domain to cells expressing FcγR. The invention also describes a family of cloning vectors which direct expression of fusion proteins and fusion proteins that can mimic aggregated IgG (AIG) and immune complex function with respect to their interactions with FcγR and which allow for the inclusion and targeting of a second protein domain to cells expressing FcγR. Expressing multiple linear copies of at least portions of the hinge and CH2 domains (HCH2) of human $IgG_1$ fused to the framework region of human $IgG_1$ gives a recombinant protein with these features. Convenient restriction sites allow for the facile introduction of additional amino-terminal domains. The resulting molecule is tripartite. The carboxyl-$IgG_1$ framework domain provides stability and permits dimerization; the intervening HCH2 polymer confers increased effector function, including targeting to subsets of cells expressing FcR, increased capacity to ligate FcR and/or to bind complement components, while the amino terminal domain can deliver an additional signal to cells expressing FcγR.

Another aspect of the invention describes methods for preparing the polypeptides and fusion proteins of the invention as well as methods for the use of the polypeptides and fusion proteins of the invention. Methods include treating inflammatory diseases, altering immunity, killing neoplastic cells, and delivering therapeutic agents to a delivery site.

A. Antibody Structure

Antibodies comprise a large family of glycoproteins with common structural features. An antibody is comprised of four polypeptides that form a three dimensional structure which resembles the letter Y. Typically, an antibody is comprised of two different polypeptides, the heavy chain and the light chain.

An antibody molecule typically consists of three functional domains: the Fc, Fab, and antigen-binding site. The Fc domain is located at the base of the Y. The arms of the Y comprise the Fab domains. The antigen-binding site is located at the end of each arm of the Y. The area at the fulcrum of the arms of the Y is the hinge region.

There are five different types of heavy chain polypeptides designated as α, δ, ε, γ, and µ. There are two different types of light chain polypeptides designated κ and λ. An antibody typically contains only one type of heavy chain and only one type of light chain, although any light chain can associate with any heavy chain.

Antibody molecules are categorized into five classes, IgG, IgM, IgA, IgE and IgD. The IgG class is further divided into subclasses including IgG1, IgG2, IgG3 and IgG4 for human IgG. An antibody molecule is comprised of one or more Y-units, each Y comprising two heavy chains and two light chains. For example IgG consists of a single Y-unit IgM is comprised of 5 Y-like units.

The carboxyl terminal of each heavy chain polypeptide is known as the constant (Fc) region. The amino terminal of each heavy and light chain polypeptide is known as the variable (V) region. Within the variable regions of the chains are hypervariable regions known as complementarity determining regions (CDRs). The variable regions of one heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

The mature human IgG1 heavy (H) chain typically spans 447 amino acid residues. The Fc region of the H chain is essentially the same for all IgG1 heavy chain molecules. The Fc region is the portion of the IgG1 polypeptide that interacts with Fc receptors. The Fc region can be further subdivided into three consecutive regions, the hinge, the CH2, and the CH3 domains. The binding site for Fc receptors is found within the hinge and CH2 (HCH2) domains of human IgG1.

The HCH2 region encompasses amino acid residues 216 to 340 of the human IgG1 H chain (Eu numbering). The hinge region spans residues 216 to 237 whereas the CH2 domain encompasses residues 238 to 340.

B. Immunoglobulin Fusion Proteins

Recombinant immunoglobulin fusion proteins are well known in the art. For example, see Capon, et al., 1989; Traunecker, et al., 1989; Chamow, et al., 1996; Ashkenazi, et al., 1997. Typically, a recombinant immunoglobulin fusion protein has an amino-terminus composed of a ligand-binding domain fused to a carboxyl-terminus composed of the hinge, $C_H2$, and $C_H3$ regions of Ig. The Ig class most commonly used is IgG1. The hinge, $C_H2$, and $C_H3$ regions of IgG are collectively referred to as the Fc region of IgG. The hinge region provides a flexible linker between the Fc region and the ligand binding domain. It also is the site of inter-chain disulphide bond formation, ie., the covalent linking of one antibody chain to another to make the familiar dimeric structure. The hinge region (especially the part nearest to the CH2 domain known as the hinge proximal region) is necessary for molecular recognition and binding to Fcγ receptors and complement components. Thus recombinant immunoglobulin fusion proteins are similar to Ig but lack the variable regions and the CH1 domain, which have been replaced by the ligand-binding domain. Typically, the recombinant molecule is generated at the cDNA level using recombinant DNA techniques and expressed in cell culture. Most often the recombinant immunoglobulin fusion protein is a disulfide-linked homodimer. The variations on the above described typical fusion protein are considerable. For example, in addition to ligand-binding domains, many other fusion partners have been placed at the amino-terminus, such as ligands, enzymes, and peptide epitopes.

The polymers of the present invention contain an additional region composed of linear polymers of at least portions of the hinge and CH2 domain (HCH2 polymers), as described below. The length of the polymer is varied. The introduction of a polymer unit between the framework domain and the amino-terminal domain in an IgG fusion protein results in a molecule that is tripartite in function. The framework domain provides features common to IgG fusion proteins such as stability, covalent dimerization, single-step purification, and ease of detection (Chamow, et al., 1996). The intervening HCH2 polymer confers increased effector function, including targeting to subsets of cells expressing FcR, increased capacity to ligate FcR, and to bind complement components. The amino-terminal domain can deliver a second signal. Thus, multiple molecular signals can be integrated into a single molecule with the potential for synergistic interaction between the domains. The molecules described add a further dimension to IgG fusion protein platforms by permitting the introduction of additional functions.

The polymers of this invention are composed of multiple HCH2 repeat units. The polymers were developed using a cloning system that results in the rapid addition of HCH2 units into a human $IgG_1$ framework expression vector. The HCH2 repeat unit is composed of the hinge and $CH_2$ domain from an Ig such as $IgG_1$, which encompasses the region known to bind FcR and complement. To prevent inter-chain disulfide bond formation between the HCH2 units of the polymer, hinge region cysteines of the HCH2 monomer unit were mutated to serines. These mutations leave intact those hinge residues known to interact with FcR and complement. The hinge within the framework expression vector was not mutated thus retaining the dimeric structure of IgG. Several unique restriction sites on the 5' end allow for the directional cloning of amino-terminal domains into the polymer expression constructs.

In some embodiments of the invention, it is not necessary for the entirety of the HCH2 region to be employed in making the polymers. As described above, the entire human IgG1 HCH2 encompasses amino acid residues 216 to 340 of the human IgG1 H chain (Eu numbering), with the hinge region spaning residues 216 to 237 and the CH2 domain encompassing residues 238 to 340. The interactions between IgG and Fc receptors have been analyzed in biochemical and structural studies using wild type and mutated Fc. The consensus that has emerged from numerous studies is that the critical regions for binding to Fc receptors are located in the part of the hinge region closest to the CH2 domain and in the amino-terminus of the CH2 domain that is adjacent to the hinge. Of particular importance are residues 233-239 (Glu-Leu-Leu-Gly-Gly-Pro-Ser) (SEQ ID NO: 9). Mutations within this region result in substantially altered binding to Fc receptors. This region is also responsible for many of the direct interactions with Fc receptors as determined by crystallographic studies. Further into the CH2 domain, and away from the hinge, are other residues that may be, at least in some contexts, important for Fc receptor binding. Among them are Asn-297 and Pro-329. Pro-329 is involved in direct contact with Fc receptor. Asn-297 is the sole site for N-linked glycosylation within the Fc region. The presence of carbohydrate at this residue is crucial for binding to Fc receptors. It must be noted however that peptides spanning residues 233-239 of IgG1 Fc bind to FcγRIII poorly. Thus it may be argued that this region is most effective in engaging Fc receptor in the context of the overall structure of the HCH2 region.

In the examples presented below the polymers were constructed using the human IgG1 HCH2 region which encompasses amino acid residues 216 to 340 of the human IgG1 H chain. This region contains the sequences known to be vital for Fc receptor binding as well as additional flanking residues. The flanking residues provide structural stability and spacing between the HCH2 units. The inventors envisage that in some embodiments it can be advantageous to construct HCH2 polymers comprised of regions within the HCH2 instead of the entire HCH2 unit. This may be done for example to reduce the size of the HCH2 unit and hence the polymer. One way that this could be achieved is through the deletion of flanking residues on either side of the region known to be vital for Fc receptor binding. For instance the hinge could be truncated to span residues 233 to 237 instead of residues 216 to 237 as used in the examples presented herein. Similar considerations apply to the CH2 region which spans residues 238-340 and to the hinge and CH2 regions of other Ig's including IgA, IgD, IgG2, IgG3, IgG4, and IgE. Of course, those of skill in the art will, in view of the teachings of this specification, be able to make, test, and use any number of different configurations of portions of HCH2 regions in the context of the invention.

The polymers of this invention bind to low affinity FcR. In some instances the polymers will bind the high affinity FcR receptors, for instance the FcγRI receptor. This is a natural consequence of the high binding affinity of the high affinity FcR receptors for the HCH2 region.

In some instances it can be advantageous to construct HCH2 polymers that bind all forms of the low affinity FcγR receptors such as, for example, FcγRIIa, FcγRIIb, FcγRIIc, FcγRIIIa and FcγRIIIb. In other embodiments the number and spacing of HCH2 units comprising the polymer are varied to increase the binding to one type of FcR receptor or conversely to decrease binding to another type of FcR receptor. In yet other embodiments alterations to the HCH2 monomer unit can be made to increase specificity of the polymer for one type of FcγR receptor and/or to decrease specific binding to another type of FcγR receptor. Such alterations are achieved by mutating certain amino acid residues within the HCH2 sequence to other amino acid residues. The choice of residues to mutate within the HCH2 unit is determined by choice of target receptor specificity and are well known to those skilled in the art. For example see Shields, et al., 2001; Sondermann, et al., 2000; Morgan, et al., 1995; Hulett, et al., 1994. In other embodiments the specific binding of the HCH2 polymers to different FcγR receptors can be enhanced by the presence of- and type of glycosylation of the HCH2 polymer. Choice of expression system in which to produce the HCH2 polymers in part determines the extent and type of glycosylation.

In the examples presented herein the polymers were constructed using DNA sequences from human IgG1. In some instances it can be advantageous to construct HCH2 polymers comprised solely of human sequences to use as immunotherapeutic agents in humans. However in some embodiments the polymers are assembled from sequences of other Ig's including IgA, IgD, IgG, IgM, and IgE. In other embodiments the polymers are assembled from sequences of more than one type of Ig, for example a polymer containing HCH2 units derived from IgG sequences are linked to HCH2 units derived from IgE sequences. In other embodiments the HCH2 polymers are comprised of non-human sequences. The choice of sequences used to construct the polymers and polymer fusion proteins is determined by the target receptor and host identity (human or non-human). In yet other embodiments the hinge region cysteines are mutated to amino acid residues other than serine. In some embodiments the HCH2 unit may be altered and/or mutated to bind complement components and not to bind to FcR. In other embodiments the HCH2 unit may be altered and/or mutated to bind FcR and to not bind complement.

In the examples presented herein the polymers were constructed using DNA sequences from human IgG1. The expressed proteins have been evaluated for their interactions with low affinity FcγR receptors. However in some embodiments the polymers are assembled from sequences of other Ig's including IgA, IgD, IgG, IgM, and IgE and these polymers will bind to and interact with the FcR for other Ig's including FcαR, FcεR, FcμR, FcδR, and FcRn. In other embodiments the polymers are assembled from sequences of more than one type of Ig, for example a polymer protein containing HCH2 units derived from IgG sequences and IgE sequences will interact and bind with the FcR for more than one type of Ig.

In the examples presented herein the polymers are constructed from monomers consisting of full length HCH2 units. In some embodiments it may be advantageous to construct polymers that contain monomers that are smaller than full length HCH2 units. HCH2 polymer proteins derived from a smaller HCH2 unit would have a smaller size and mass yet still retain the ability to effectively bind to and activate FcR and/or complement. The reduction in the size of the HCH2 unit is achieved by the removal of sequences that are not involved in the binding to FcR and/or complement. The identity of the sequences that are not involved in the binding to FcR and/or complement are well known, as are the methods for their removal from the HCH2 monomer unit. The removal of these sequences would fail to affect the desired binding but yield a polymer of smaller mass.

Recombinant HCH2 polymer constructs can mimic the biological activity and functions of immune complexes (ICs), of aggregated IgG (AIG), and of aggregated Fc. The use of recombinant HCH2 polymer constructs offers several advantages over AIG or Fc aggregates. The number and spacing of HCH2 units can be altered to hone interaction with FcR's. Aggregates are by nature heterogeneous with considerable variation between batches whereas the recombinant HCH2 polymers are precisely defined. As shown herein HCH2 polymers are considerably more potent than AIG. Perhaps this result is achieved by expressing only those determinants necessary for FcR engagement and/or by presenting them in a particularly favorable configuration.

The receptors can be specifically activated with constructs containing different numbers of HCH2 units. As shown herein, the number of repeating HCH2 units available to bind receptor markedly influences cell function. Cell function changes with addition of a single HCH2 unit. The constructs of the present invention allow for the measurement of change in receptor function based on IC size. The number of repeating HCH2 units included within the polymer construct is variable and is selected in order to optimize biological activity. In one embodiment the HCH2 polymers are assembled as disulfide-linked homodimers. In some embodiments the HCH2 polymers are assembled as monomers (single chain polypeptide), or hetero- or homo-multimers, and particularly as dimers, tetramers, and pentamers.

The extracellular domain of a variety of proteins, including human CD8α and human serum albumin (HSA) can be expressed as HCH2 polymer fusion proteins. The biological activity of these recombinant CH2 polymers compares favorably to the activity of AIG and an anti-CD16 monoclonal antibody. The activity of the fusion proteins positively correlates to the number of HCH2 units. The largest polymer tested using either a CD8α extracellular domain or HSA domain was several times as potent as AIG at similar concentrations.

Many protein domains can be expressed as HCH2 polymer fusion proteins. A nonlimiting list of such proteins includes ligand-binding domains, extracellular domains of receptors, enzymes, adhesion molecules, cytokines, peptide hormones, immunoglobulin fragments (Fab'), ligands, and antigens. Sites at which the fusion of the protein domain are made are well known and may be selected to optimize biological activity, stability, secretion, avidity, and binding specificity. HCH2 polymer fusion proteins involving IgG1 were designed using sequence data from the human IgG1 constant region gene as a guide (accession #Z17370). Two amino terminal domains have been expressed fused to the HCH2 polymers: the extracellular domain of human CD8α (accession #M12824) and domain I of human serum albumin (accession #V00494). In some instances it may be advantageous to construct HCH2 polymers composed of the HCH2 polymer region unfused to additional protein domains or framework sequences.

In certain preferred embodiments the fusion proteins of the current invention are produced by the insertion of the HCH2 polymeric region into an existing antibody sequence or the sequence of a recombinant protein. This process is advantageous in that there is a large body of research on numerous antibodies that can be used to bind to a preferred therapeutic agent. Another advantage of this method is its simplicity. The HCH2 polymeric region is a discrete, modular DNA element designed for easy transfer from one cDNA construct to another. A modular DNA element is sometimes referred to as a 'cloning cassette'. The HCH2 polymeric region can be used as a cloning cassette and simply spliced into the existing cDNA for any protein, thus removing several steps from the formation process. In certain circumstances the precise site of insertion within a protein sequence will be determined by routine experimentation. However, the appropriate site of insertion for immunoglobulins and proteins derived therefrom is well known. Using this approach, existing monoclonal antibodies and recombinant immunoglobulin fusion proteins can be easily modified through the addition of the HCH2 polymer region.

C. The Immune System

The immune system can be divided into two arms known as the innate and adaptive immune systems. The innate immune system provides a first line of defense against invading microorganisms or other insults. Cell types involved in innate system defenses include natural killer (NK) cells, B cells responsible for natural antibody production, and monocytes/macrophages. The adaptive immune system is more finely honed, exhibits immunological memory and provides a second and more specific line of defense. Cell types involved in adaptive immunity include T cells, B cells involved in T cell-dependent antibody responses, and again monocytes/macrophages. Interactions between the innate and adaptive systems are complex with reinforcement under some circumstances and antagonism under others. Several of these interactions involve controls exerted by immune complexes and, by extension, by the present invention, inasmuch as the present invention provides a mimic for immune complexes.

1. NK Cells

NK cells are large granular lymphocytes that are generated in the bone marrow. They can be recognized by their distinct morphology and by surface marker molecules that they either express or fail to express. NK cells are $CD16^+$, $CD56^+$, and $CD3^-$. NK cells are found in the spleen, the blood, and the tissues, but not in lymph nodes. They have the capacity to kill some tumor cells, some virally infected cells, and to release cytokines, and in particular interferon gamma and tumor necrosis factor (TNF) both of which contribute to the initial control of viral infections and both of which additionally exert regulatory influences over the T and B cells involved in adaptive immunity and autoimmune diseases. The present invention activates NK cells causing them to proliferate and to secrete increased amounts of interferon gamma and TNF. The CD16 surface marker that NK cells express is the FcγRIIIa receptor to which the present invention binds. This binding is responsible for the activation of NK cells. NK cells themselves have a protective role in at least some autoimmune processes since their depletion augments the severity of experimental autoimmune encephalomyelitis, an animal model for multiple sclerosis, one of the major autoimmune diseases of man. Accordingly NK cell activation by the present invention offers the prospect of improved treatment for autoimmune processes.

It is one embodiment of the current invention that HCH2 polymer fusion proteins can be used to activate NK cells, drive them to expand in number both in vivo and in vitro, and to secrete cytokines with known anti-tumor and anti-viral activities for the purpose of targeting, eliminating, or otherwise destroying neoplastic cells, malignant cells that make up a tumor, cancer cells or virally infected cells. Culture of human peripheral blood lymphocytes (PBL) with high doses of IL-2 results in the generation of cytotoxic cells termed lymphokine-activated killer (LAK) cells (Rosenstein, M., et al., 1984). LAK cells are a mixture of NK cells and T cells. A characteristic of LAK cells is their ability to lyse a variety of tumor cells in a non-MHC-restricted fashion. Tumor cell recognition by NK cells is antigen independent. One approach to cancer therapy is to administer high doses of intravenous IL-2 to generate NK/LAK cells from PBL in vivo. However the substantial toxicity of therapeutic levels of intravenous IL-2 have limited its use as a cancer therapeutic. Consequently NK/LAK cells are cultured from patient PBL in vitro with high doses of IL-2 and, after several cycles of expansion in cell number, returned to the patient (Hayes, R., et al., 2001). A related approach involves the isolation of tumor infiltrating lymphocytes (TIL) from resected tumors which are also expanded in vitro with high doses of IL-2. Though they represent a small fraction of the total immunocyte population, activated NK cells are an important component of TIL (Brittenden, J., et al., 1996). The polypeptides of the current invention, in conjunction with IL-2, are potent activators of NK cells. NK cells are activated by HCH2 polymers to a much higher level than is possible with IL-2 alone (Example 13). HCH2 polymers offer two distinct advantages over IL-2 therapy alone. First, co-administration of HCH2 polymers and IL-2 may achieve NK cell activation at substantially lower levels of IL-2 than when IL-2 alone is employed thus avoiding many of the toxicities associated with high level IL-2 therapy in vivo. The HCH2 polymers of the current invention are anticipated to find application for the in vitro expansion of LAK/TIL cells as well. Secondly, the HCH2 polymers also potently induce the secretion of TNF-α and IFN-γ from NK cells (Example 16). Both TNF-α and IFN-γ have known anti-tumor and anti-viral effects (Fortis, C., et al., 1999).

2. Monocytes and Macrophages

Macrophages derive from monocytes and share many of their functions. For this reason the two will be considered together. Monocytes mature in the bone marrow. They are found in the blood and throughout the tissues. They function both in innate defenses and in adaptive defenses. At the onset of viral infections they release IL-12, a protein that activates NK cells for interferon gamma and TNF production, the importance of which in viral and tumor defenses has been discussed above. Monocytes function as antigen presenting cells and for this reason are critical for the activation of T cells and hence adaptive immunity. They, in turn, are activated for phagocytosis by products released by activated T cells and, once activated, clear both invading organisms, and cells and tissues damaged by invading organisms or by autoimmune processes.

Monocytes also exhibit regulatory properties exerted by products that they release. These products act to inhibit immune responses including autoimmune responses. Among the regulatory molecules released by monocytes are IL-10 and prostaglandin E2.

Monocytes express all three classes of Fc receptor. Binding of HCH2 polymers to FcR expressed on monocytes may result in the ligation of Fcγ RII, the ligation of FcγRIIIa or in the coaggregation of both FcγRII and FcγRIIIa receptors. Ligation of the FcγRIIIa receptor on monocytes is known to potently induce IL-10 and prostaglandin E2 production by monocytes (Passwell, et al., 1979; Ferreri, et al., 1986; Berger, et al., 1996) offering the prospect that the present invention may, via similar induction, contribute to the control of autoimmune processes.

3. B Cells

B cells produce antibody. Initial production of IgM class antibody is independent of T cell influence but the subsequent switch to IgG and other classes of antibody occurs under the direction of T cells. Both T cell-independent antibodies and T cell-dependent antibodies can participate in autoimmune responses. B cells express the FcγRIIb receptor (CD32). The FcγRIIb receptor delivers a negative signal mediated through a specialized signaling motif know as the immunoreceptor tyrosine-based inhibitor motif (ITIM) located within the cytoplasmic tail of the receptor. The ITIM motif is a unique feature of the FcγRIIb receptor and is not present in any other Fcγ receptor class. Ligation of this receptor provides a negative signal to B cells and hence an inhibitory signal for antibody production. The FcγRIIb receptor recognizes and responds to IgG-containing immune complexes and to IgG aggregates. Accordingly, it would be expected to respond to the present invention with, as a consequence, inhibition of production of both IgM class and IgG class immunoglobulin production.

Antibody production by B cells is also subject to down-regulatory controls exerted by products released by T cells and monocytes. Among such controls is that exerted by regulatory CD8 cells, sometimes referred to as suppressor cells. IgG aggregates, added to peripheral blood mononuclear cell preparations in vitro, activate CD8 cell-mediated inhibition of immunoglobulin production, even though CD8 cells do not express the Fcγ receptors to which IgG aggregates bind. The result is thought to depend on an induction of CD8 cell activity by products released by the NK cells and monocytes to which IgG aggregates do bind. Since the present invention mimics the activity of IgG aggregates, an indirectly mediated induction of CD8 cell-mediated regulatory activity, and hence a beneficial effect on autoimmunity was anticipated and in fact found.

4. T Cells

T cells are small lymphocytes that mature in the thymus, whence they make their way to the lymphoid organs. T cells can be divided into 2 major categories known as CD4 cells and CD8 cells. The two categories have different, albeit overlapping, functions. CD4 cells are responsible for cell-mediated immunity, sometimes referred to as delayed type hypersensitivity. Cell-mediated immunity is implicated in the pathogenesis of numerous autoimmune diseases. CD4 cells recognize antigens by means of T cell receptors expressed on the cell surface. Antigenic peptide fragments are presented to CD4 cells by MHC class II molecules expressed on the surface of antigen presenting cells such as monocytes. T cells are activated by this presentation but only if a second activating signal is provided by the antigen presenting cell. Activated CD4 cells release cytokines that are responsible for their biologic effects. CD4 cells can be divided into 2 subclasses known as Th1 cells and Th2 cells. Th1 cells are responsible for cell-mediated immunity while Th2 cells direct production of IgG and other classes of immunoglobulin by B cells.

CD4 cell responses are tightly regulated and the regulatory mechanisms can be exploited to treat autoimmune diseases. CD4 cells do not express Fcγ receptors but a control over CD4 cells can be exerted by cytokines such as IL10 produced by monocytes as a consequence of Fcγ receptor ligation. Cytokines released by NK cells as a sequelum of Fcγ receptor ligation can also contribute to CD4 cell inactivation. In addition, products released by CD8 cells (see below) can inhibit CD4 cells. CD8 cells are primed for regulatory activity by products released by NK cells and monocytes following ligation of the Fcγ receptors expressed on the surface of NK cells and monocytes. For all these reasons the present invention offers the prospect of inhibiting those activities of Th1 and Th2 cells that contribute to the pathogenesis of autoimmune processes.

CD8 cells comprise the second major category of T cells. They recognize peptides presented to them by MHC class I molecules expressed on the surface of antigen presenting cells. As with CD4 cells a co-stimulatory signal is required for CD8 cell activation. The vast majority of CD8 cells do not express Fcγ receptors. CD8 cells have 2 established major functions. The first is cytotoxicity, a critical component in the control of infections by viruses and other organisms that reside intracellularly. The second major function is the regulatory function already discussed.

The brief synopsis of immune system function given above is cursory. Its purpose is to highlight some of the mechanisms by which the present invention can be expected to have a favorable impact on autoimmune processes.

D. Fc Receptors and the Complement System

There are three classes of Fc receptor (Gessner et al., 1998; Raghavan et al., 1996). FcγRI (CD64) binds monomeric IgG with high affinity whereas AIG and IC bind preferentially to FcγRII (CD32) and FcγRIII (CD16), the low affinity receptors for Fc. FcγRII and FcγRIII are closely related in the structure of their ligand-binding domains. In humans three separate genes, FcγRIIA, FcγRIIB, and FcγRIIC, two of which give rise to alternatively spliced variants, code for FcγRII. FcγRIIa delivers activating signals whereas FcγRIIb delivers inhibitory signals. The functional basis for the divergent signals arises from signaling motifs located within the cytoplasmic tails of the receptors. An immunoreceptor tyrosine-based inhibitor motif (ITIM) located in the cytoplasmic tail of the FcγRIIb is critical for negative receptor signaling. The ITIM motif is a unique feature of the FcγRIIb receptor and is not present in any other Fcγ receptor class. In contrast, an activatory immunoreceptor tyrosine-based activation motif or ITAM is located in the cytoplasmic tail of FcγRIIa. ITAM motifs transduce activating signals They are also found in the FcR γ-chains, which are identical to the γ-chains of the high affinity IgE receptor (FcεRI). While FcγRIIa and FcγRIIb are widely expressed on myeloid cells and some T-cell subsets they are notably absent from NK cells.

Human FcγRIII is also present in multiple isoforms derived from two distinct genes (FcγRIIIA and FcγRIIIB). FcγRIIIb is unique in its attachment to the cell membrane via a glycosylphosphatidyl anchor. FcγRIIIb expression is restricted to neutrophils while FcγRIIIa is expressed by macrophages, and NK cells (both FcγRIIIa). FcγRIIIa is also expressed by some γδ T-cell subsets and certain monocytes. FcγRIIIa requires the presence of the FcR γ-chain and/or the CD3 ζ-chain for cell surface expression and signal transduction. The FcR γ-chain and the CD3 ζ-chain are dimeric and possess ITAM motifs. FcγRIIIa forms a multimeric complex with these subunits and signaling is transduced through them. Thus, there is considerable FcγR receptor heterogeneity and diverse expression profiles.

AIG and IC have been used to target FcRIIIa on immune cells, but as noted earlier production of defined AIG and IC was seen to be problematic. Assembly of complexes by physical or chemical methods is difficult to control with precision resulting in heterogeneity within complexes of similar molecular weight in addition to variations between preparations and changes in composition upon storage. Molecular cloning has been used in the present invention to create molecules that can mimic or approximate AIG and IC function with respect to their interactions with FςcR and which allow for the inclusion and targeting of a second protein domain to cells expressing FςcR.

The binding sites for FcγRII and FcγRIII map to the hinge and proximal region of the CH2 domain of IgG, the same region originally identified for FcγRI (Duncan et al., 1988; Morgan et al., 1995; Lund et al., 1991). White et al. (2001) describe the cloning and expression of linear polymers of the hinge and CH2 (HCH2) fused to the Fc region of $IgG_1$ and demonstrate their biological activity. Legge et al. (2000) have recently shown that an aggregated PLP1 immunoadhesin, unlike the monomeric form, moderates disease severity in experimental autoimmune encephalomyelitis, the rodent model for multiple sclerosis. This change is due to the dual functionality of the aggregated Fc and PLP moieties within the complex.

In the later phase of a primary immune response or in chronic responses, large ICS form. These complexes signal through the low affinity IgG receptors that recognize ICS or IgG aggregates preferentially. The low affinity receptors are of two classes FcγRII (CD32) and FcγRIII (CD16). FcγRIIb provides an inhibitory signal for secretion of cytokines that augment immunoglobulin secretion including IgG secretion. FcγRIIIa (found on NK cells, monocytes and γδ T cells) preferentially recognizes IgG1. One thrust of this invention is directed towards activation of FcγRIIIa.

The ability of FcγR to bind IgG and transmit a signal into the cell depends upon the FcγRs alleles expressed, upon glycosylation, and how the receptor is associated with the signaling subunit. In addition, glycosylation patterns differ between cell types and this too can affect ligand binding to FcγRIIIa. FcγRIIIa on NK cells is glycosylated with high mannose oligosaccharides, whereas monocyte/macrophage FcγRIIIa is not. Perhaps this imparts lower receptor affinity to monocyte/macrophage FcγRIIIa relative to NK cell FcγRIIIa, adding yet another level of modification to receptor function (Galon et al., 1997; Edberg et al., 1997). Thus, FcγR function is regulated at several levels, which can have an impact on ligand binding and receptor signaling.

Recently, the inventors have initiated studies into the potential immunomodulatory role of immune complexes (IC) in human autoimmune syndromes. Central to these studies are the interactions between IC and FçcR. However, production of defined IC is difficult to control with precision. Molecular cloning is used to create molecules that can mimic or approximate IC function with respect to their interactions with FçcR and which allow for the inclusion and targeting of a second protein domain to cells expressing FçcR. The strategy pursued is to express multiple linear copies of the region of the IgG framework that binds FçcR. Expressing only those determinants necessary for FcR engagement and presenting them in a particularly favorable configuration results in novel proteins that are considerably more potent than IC. Thus recombinant IC mimetic proteins described herein will provide both a valuable tool for the examination of IC deposition and in the therapeutic targeting of FcR in autoimmune disorders.

1. FcγRIIIa and NK Cells

NK cells express only one type of FcγR, FcγRIIIa, which upon ligation results in lymphokine expression and up-regulation of the constitutively expressed low affinity IL-2 receptor, IL-2R (p75) (Anegon, et al., 1988). Exposure to high dose IL-2 alone results in lymphokine expression, increased IL-2R expression, enhanced cytotoxic function, but only modest proliferative responses by NK cells (Nagler, et al., 1990). Co-stimulation with high doses of IL-2 together with FcγRIIIa ligation results in greater NK-cell activation including brisker proliferation than is achieved with IL-2 alone (Harris, et al., 1989). The proliferative response of NK cells is used as a biological read-out for FcγR-ligand interactions. For example four HCH2 polymer constructs were tested on PBMC at 2.5 μg/mL and results were compared to those obtained with anti-CD16 mAb and AIG. As expected anti-CD16 mAb and AIG induced a proliferative response in the presence of IL-2. Proliferative response driven by the HCH2 polymer constructs correlated with the number of repeat units, CD8R0 gave a 7.5 fold induction over IL-2 alone whereas CD8R4 gave a 15-fold induction. CD8R4 induced the highest level of activation, but the level of induction by CD8R3 approached that for CD8R4 and the difference between them was not statistically significant. Both constructs may be at or near the number of HCH2 units necessary to optimally engage FcγR. Direct comparison between CD8R4 and AIG reveals that CD8R4 is considerably more potent that AIG: CD8R4 produces a 18-fold induction at 5 μg/μL while 125 μg/μL of AIG is necessary to produce similar levels of induction.

The availability of a recombinant protein that approximates the functions of aggregated IgG and at the same time delivers a second signal may permit dissection of the relative importance of the various mechanisms that have been postulated to explain the immunomodulatory role of AIG. Blockade of FcγR probably does not suffice to explain the multiple effects of AIG on immune cells. Other potential mechanisms involve the inhibition of antigen recognition by T-cells, activation of FcγRIII on NK-cells, and altered cytokine synthesis and secretion. HCH2 polymers may also provide a valuable tool for the examination of IC deposition.

Binding of ligands to FcγRIIIa on NK cells induces IFN-γ and TNFα secretion, antibody dependent cellular cytotoxicity (ADCC), proliferation, and under some circumstances, but not all, apoptosis. Some functions require a second signal, which can be provided by IL-2. FcγRIIIa on NK cells can associate with either the γ chain of the high affinity IgE receptor (FcεRI) or with the ζ chain of the T cell receptor (Lanier, et al., 1989; Lanier, et al., 1991; Kurosaki, et al., 1991). Either chain may transmit intracellular signals following ligand binding to FcγRIIIa.

Signaling through the CD2 receptor on NK cells also occurs through the ζ chain (Vivier, et al., 1991; Moingeon, et al., 1992) and anti-CD2 antibodies have been effectively employed to study NK cell function and suppressor mechanisms. Thus, activation of NK cells through CD2 or CD16 induces overlapping effector functions, including secretion of IFN-γ and TNFα, and proliferation. Activation of NK cells through CD2 induces secretion of TGFβ, which acts upon CD8 T cells that then inhibit Ig secretion by B cells (Gray, et al., 1994; Ohtsuka, et al., 1998). Release of soluble CD16, a powerful inhibitor of Ig secretion in vitro, by activated NK cells provides a potential second mechanism of Ig regulation by NK cell activation.

2. The Complement System

Signaling through the CD2 receptor on NK cells also occurs through the ζ chain (Vivier, et al., 1991; Moingeon, et al., 1992) and anti-CD2 antibodies have been effectively employed to study NK cell function and suppressor mechanisms. Thus, activation of NK cells through CD2 or CD16 induces overlapping effector functions, including secretion of IFN-γ and TNFα, and proliferation. Activation of NK cells through CD2 induces secretion of TGFβ, which acts upon CD8 T cells that then inhibit Ig secretion by B cells (Gray, et al., 1994; Ohtsuka, et al., 1998). Release of soluble CD16, a powerful inhibitor of Ig secretion in vitro, by activated NK cells provides a potential second mechanism of Ig regulation by NK cell activation.

The classical activation pathway and CDCC are the complement-mediated mechanisms most relevant to the fusion protein of the current invention. The complement binding site on the Fc portion of IgG1 encompasses the hinge and CH2 regions. The inventors envisage the use of the HCH2 polymers of the current invention to greatly facilitate classical pathway and CDCC mediated removal of target cells. In other circumstances complement activation may pose unwanted and problematic side reactions. In these cases the inventors envisage the alteration of HCH2 polymer-C1q interactions so as to lessen or eliminate complement activation.

E. Use of HCH2 Polymeric Fusion Proteins as in vivo and in vitro Immunological Agents 1. Clinical Use of Antibodies The advent of monoclonal antibody (mAb) technology provided the basis for developing potentially therapeutic reagents that react with specific cell surface antigens involved in cell function. Therapeutic reagents of this type can be incorporated into the fusion proteins of the current invention.

One of the clinically successful uses of monoclonal antibodies is to suppress the immune system, thus enhancing the efficacy of organ or tissue transplantation. U.S. Pat. No. 4,658,019 describes a novel hybridoma (designated OKT3), which is capable of producing a monoclonal antibody against an antigen found on essentially all normal human peripheral T cells. This antibody is said to be monospecific for a single determinant on these T cells, and does not react with other normal peripheral blood lymphoid cells. The OKT3 mAb described in that patent is currently employed to prevent renal transplant rejection (Goldstein, 1987).

Monoclonal antibodies are an emerging class of powerful therapeutic agents. Several have been approved for the treatment of malignancies including cancer and many more are in the process of clinical development. For example Rituximab (Rituxan, Mabthera) is a mAb which targets the CD20 molecule expressed on the surface of B cells. Rituximab was the first therapeutic mAb approved for the treatment of a malignancy, in this case non-Hodgkin's lymphoma. Rituximab is a chimeric IgG1 mAb composed of murine variable domains and human constant regions. Rituximab exerts its effects through several mechanisms: Induction of apoptosis in B cells, direct complement killing (CDC) and cellular effector mechanisms such as antibody-dependent cell-mediated cytotoxicity (ADCC) and the related pathway of complement-dependent cellular cytotoxicity (CDCC) (Johnson, et al., 2001). CDC and cellular effector mechanisms are mediated through the Fc region of mAb, in addition ADCC relies on Fc-FcR receptor interactions. Two lines of evidence strongly implicate interactions between Rituximab and the FcγRIIIa receptor as crucial to the therapeutic effectiveness of Rituximab. First, patients with the FcRγIIIa receptor 158V allotype have subtantially greater clinical responses to Rituximab therapy, including complete clearance of malignant cells, than patients with the FcγRIIIa receptor 158F allotype. The FcγRIIIa receptor 158V allotype has higher affinity for human IgG1 than the FcγRIIIa receptor 158F allotype. It also promotes increased ADCC (Cartron, et al., 2002). Secondly, mice with gene knock-outs that result in the loss of FcγRIIIa and FcγRI receptor expression have deficient responses to anti-CD20 mAb therapies, including Rituximab (Clynes, et al., 2000).

a. Modification of Recombinant Monoclonal Antibodies by the Introduction of a HCH2 Polymer It is an embodiment of the current invention that recombinant monoclonal antibodies (mAb) can be modified by the introduction of one or more HCH2 units into the Fc region to create a HCH2 polymer of appropriate length within a monoclonal antibody. Monoclonal antibodies modified in this manner will retain their target specificity while acquiring improved and/or more selective effector function. HCH2 polymers greatly enhance Fc-FcR receptor interactions. More specifically HCH2 polymers of the current invention have greatly improved binding to and enhanced activation of FcγRIIIa receptors over that seen with the Fc portion of mAb in current therapeutic use. As enhanced interaction of mAB with FcγRIIIa has been documented to have therapeutic benefit in the treatment of malignancies the inventors envisage modifying existing mAb with the introduction of an HCH2 polymer into the Fc region of the mAb. Monoclonal antibodies with this modification will have enhanced interaction with FcγRIIIa receptors.

Functional IgG genes, those that direct expression of a mAb, are composed of heavy and light chain genes segments. Light chain (L) genes consist of three exons, containing the hydrophobic leader sequence, the variable regions and the L constant region ($C_L$). Separating the exons are the intervening sequences or introns. Similarly, the variable region of a functional Ig heavy chain (H) gene has a separate exon for each of the leader sequence, the variable region, and H chain constant region (CH1). The H gene also contains the Fc region which is composed of separate exons for the hinge, the CH2 region and CH3 regions. Once again the exons are separated by introns. The expression of mAb in mammalian cells typically involves cloning both the H and L gene segments from functional Ig genes into either a single expression vector or separate expression vectors (one for L, one for H genes) that posses the Ig promoter region. Once subcloned the expression vectors possessing the L and H genes are transfected into an appropriate cell line for expression. The use of gene segments insures the presence of intronic sequences, which contain enhancer and other elements that collectively allow for high levels of Ig expression in B cells and myeloma cells. Ig expression systems utilizing the Ig promoter and intronic genetic elements limit protein expression to cells of lymphoid derivation however.

More recently, Ig expression systems have been developed that use viral promoters and enhancer combinations, such as CMV. The use of viral promoter/enhancer combinations permits strong expression in both lymphoid and non-lymphoid cells lines such as CHO and COS (Norderhaug, et al., 1997). Inclusion of the intronic enhancer from the Ig H gene also directs high level expression in lymphoid cells. Additionally, H and L gene segments are no longer necessary for efficient expression and can be replaced by their corresponding cDNA's (McLean, et al., 2000).

The introduction of HCH2 polymers into mAb can be achieved by any of several approaches. In one method, using molecular cloning techniques well known to those skilled in the art, H chain gene segments within expression vectors are modified by the insertion of the HCH2 polymer cloning cassette into the 5' end of the hinge exon. The modified hinge exon now consists of the HCH2 polymer fused in frame to the hinge sequences. The vector containing the modified H gene is introduced in conjunction with a L gene into an appropriate cell line for mAb expression. A more preferable method is to replace the Fc gene segment with a cDNA segment comprising a splice acceptor signal, the HCH2 polymer fused to an Ig Fc cDNA and a polyA signal. The modified H gene is then transferred into an Ig expression vector capable of directing Ig expression without Ig gene intronic sequences. The vector containing the modified H gene is introduced in conjunction with an L gene into an appropriate cell line for expression.

The insertion of HCH2 polymers into mAb expressed from cloned cDNA within expression vectors can also be achieved using similar techniques. For instance, the cDNA encoding the Fc region can be removed from the H chain cDNA and replaced with a DNA segment encoding the HCH2 polymer fused to a Fc cDNA. Conversely, the cDNA encoding the H chain leader, variable and CH1 region can be excised and transferred to vectors containing the HCH2 polymer region genetically fused to a Fc cDNA. Alternatively, the HCH2 polymer cassette can be introduced into the H chain cDNA at the appropriate site. This site would most commonly be the junction between the CH1 region and the hinge. The method of introduction is well known to those skilled in the art.

Subsequently, the modified H chain cDNA is then transferred into an Ig expression vector capable of directing Ig expression without Ig gene intronic sequences. The vector containing the modified H chain cDNA is introduced in conjunction with an L chain expression vector into an appropriate cell line for expression.

While interaction with FcγRIIIa receptors is important for the efficacy of several mAb in clinical use, the methods of modification described above are general. In other applications, HCH2 polymers can be introduced into mAb to enhance specificity for other individual FcR receptors, classes of FcR receptors, as blocking reagents for FcR receptors, or for binding to complement factors.

2. Preparation of Monoclonal and Polyclonal Antibodies

The methods for generating monoclonal antibodies (MAbs) generally begin along the same lines as those for preparing polyclonal antibodies. Briefly, one begins by immunizing an animal with an immunogen, and collecting antisera from that immunized animal to prepare a polyclonal antibody. A wide range of animal species can be used for the production of antisera. Typically an animal used for production of antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvant and aluminum hydroxide adjuvant.

The amount of immunogen used for the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal). Blood of the immunized animal is sampled at various time points following immunization to monitor the production of polyclonal antibodies. When a desired level of immunogenicity has been obtained, the immunized animal can be bled and the serum isolated and stored.

A monoclonal antibody can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides. Where azaserine is used, the medium is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with antigen-polypeptides. The selected clones can then be propagated indefinitely to provide the monoclonal antibody.

By way of specific example, to produce a monoclonal antibody, mice are injected intraperitoneally with between about 1-200 μg of an antigen comprising a polypeptide. B lymphocytes are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT medium (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection medium.

Each of the surviving hybridoma cells produces a single antibody. These cells are then screened for the production of the specific antibody immunoreactive with an antigen/polypeptide. Limiting dilution of the hybridomas isolates single cell hybridomas. The hybridomas are serially diluted many times and, after the dilutions are allowed to grow, the supernatant is tested for the presence of the monoclonal antibody. The clones producing that antibody are then cultured in large amounts to produce an antibody in convenient quantity.

3. In Vitro Uses of HCH2 Polymeric Fusion Proteins

In addition to the above-described uses, the claimed peptides will have a variety of in vitro uses. Some of these are described below, those of skill in the art will understand others.

a. Immunoassays

The success of immunoassays that accurately quantitate the amount of a desired agent is based in large part on either capturing the agent in a specific manner, detecting the agent in a specific manner, or both. The inventors envisage that the fusion protein of the current invention may find utility in the specific detection of, or capturing of, Fc receptors. The binding of the fusion proteins of the current invention to Fc receptors allows for their use in the specific capturing or detecting of these receptors. The fusion proteins of the current invention may be immobilized onto a suitable surface and used to capture Fc receptors. Subsequently, the captured Fc receptors may be detected using other agents such as antibodies directed against a noncompeting site of the receptor. Alternatively, the fusion proteins may be used to detect Fc receptors that are either nonspecifically or specifically captured onto a suitable surface. By varying the immunoassay procedure the fusion proteins of the current invention may be utilized for the detection of CD16 and CD32 in a variety of manners.

The inventors further envisage that the fusion proteins of the current invention will find utility in the detecting or capturing of a wide range of agents. Immunoassays allow for the detection and quantitation of an agent, and in particular the presence and quantitation of a small amount of agent, by including a step in the procedure that amplifies the signal to noise ratio. The fusion proteins of the current invention can be used to amplify the signal to noise ratio in a wide variety of immunoassays by virtue of their repetitive HCH2 regions. In this embodiment of the current invention, a fusion protein would coexpress a ligand binding domain able to bind specifically to the agent of interest giving specificity to the fusion protein. The repetitive HCH2 region allows for an amplification step as it contains numerous repeating units that can be targeted by a wide variety of agents known to those familiar in the art. For example, polyclonal sera, conjugated to an enzyme or other suitable signal generating agent, reactive with the HCH2 region may be used in the detecting procedure. The repeating HCH2 region would allow for the binding of numerous Ig present in the polyclonal sera that are reactive with the HCH2 region. The fusion proteins of the current invention may find utility in the detection of agents in a wide variety of immunoassays by varying the ligand binding proteins coexpressed in the fusion proteins. A non-limiting list of agents that may be detected with the aid of the fusion proteins of the current invention include, cytokines, soluble receptors, steroids, soluble proteins, and hormones. Variations of immunoassay procedure are envisaged by the inventors and should be known to those familiar in the art. Although the above mentioned uses of the fusion proteins of the current invention are discussed in the context of immunoassays, the authors envisage that they are readily applicable to numerous in vitro uses where the detection of a specific agent is desired. A nonlimiting list of such in vitro uses include their use in fluorescence activated cell sorting, immunohistochemistry, and immunoprecipitation.

The fusion proteins of the invention will find utility in immunoassays for the detection of CD16. Turning first to immunoassays, in their most simple and direct sense, preferred immunoassays of the invention include the various types of enzyme linked immunosorbent assays (ELISAs) known to the art. However, it will be readily appreciated that the utility of antibodies is not limited to such assays, and that other useful embodiments include RIAs and other non-enzyme linked antibody binding assays or procedures.

In the preferred ELISA assay, samples to be tested for CD16 are immobilized onto a selected surface, preferably a surface exhibiting a protein affinity such as the wells of a polystyrene microtiter plate. After washing to remove incompletely adsorbed material, one will desire to bind or coat onto the well a nonspecific protein such as bovine serum albumin (BSA), casein or solutions of milk powder that is known to be antigenically neutral with regard to the fusion protein. This allows for blocking of nonspecific adsorption sites on the immobilizing surface and thus reduces the background caused by nonspecific binding of the antibody onto the surface.

After binding of antigenic material to the well, coating with a non-reactive material to reduce background, and washing to remove unbound material, the immobilizing surface is contacted with a fusion protein of the current invention in a manner conducive to immune complex (antigen/antibody) formation. Such conditions preferably include diluting with diluents such as BSA, bovine gamma globulin (BGG) and phosphate buffered saline (PBS)/Tween. These added agents also tend to assist in the reduction of nonspecific background. The layered antibody is then allowed to incubate for from 2 to 4 hours, at temperatures preferably on the order of 22° to 25° C. Following incubation, the antibody-contacted surface is washed so as to remove non-immunocomplexed material. A preferred washing procedure includes washing with a solution such as PBS/Tween, or borate buffer.

Following formation of specific immunocomplexes between the fusion protein and the bound antigen, and subsequent washing, the occurrence and amount of immunocomplex formation may be determined by subjecting same to a second antibody having specificity for the fusion protein of the current invention. Of course, in that the fusion protein will typically have a human IgG region, the second antibody will preferably be an antibody having specificity in general for human IgG. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectrum spectrophotometer.

b. Fluorescence Activated Cell Sorting (FACS)

Fluorescent activated cell sorting; flow cytometry or flow microfluorometry provides a means for scanning of individual cells for the presence of an antigen. The method employs instrumentation that is capable of activating, and detecting, the excitation emissions of labeled cells in a liquid medium.

FACS is unique in its ability to provide a rapid, reliable, quantitative, and multiparameter analysis of either living or fixed cells. The peptides of the current invention provide a useful tool for the analysis and quantitation of antigenic, biophysical, and biochemical characteristics of individual cells. When used with electrostatic deflection technology, the fusion proteins of the present invention can be used for the specific isolation of subpopulations of cells.

c. Immunohistochemistry

The fusion proteins of the present invention may also be used in conjunction with both fresh-frozen and formalin-fixed, paraffin-embedded, or otherwise fixed, tissue blocks prepared for study by immunohistochemisty.

d. Immunoprecipitation

The fusion proteins of the present invention are particularly useful for the isolation of CD16 and CD32 by immunoprecipitation. Immunoprecipitation involves the separation of the target antigen component from a complex mixture, and is used to discriminate or isolate minute amounts of protein. For the isolation of membrane proteins, cells must be solubilized into detergent micelles. Nonionic salts are preferred, since other agents such as bile salts, precipitate at acid pH or in the presence of bivalent cations.

F. Autoimmune Diseases

Autoimmune diseases are processes in which the immune system mounts an attack against body tissue components. This attack may be mediated by anti-tissue component antibodies produced by B lymphocytes or by cell-mediated tissue destructive processes mediated by T cells, by NK cells, and by monocytes/macrophages. In some autoimmune diseases several tissue damaging mechanisms may operate either concurrently or sequentially. The fusion proteins of the current invention can be used in the treatment of autoimmune diseases. They can be used to alter immunity and to deliver therapeutic agents to a delivery site in a patient where the therapeutic agent is effective.

The number of autoimmune diseases is considerable and some persons may have more than one autoimmune disease. Similarly, signs and symptoms may cover a wide spectrum and severity may also vary widely between afflicted individuals and over time. The reasons why some persons develop autoimmunity while others do not are imperfectly understood but certain recurring themes can be signaled. In many autoimmune processes there is a genetically determined propensity to develop disease. Among the genes that have been linked to propensity to develop autoimmunity are those of the major histocompatibility complex. In addition, environmental factors are thought to play a role. During embryonic development many of those immune system cells that are capable of reacting against self-components are eliminated but some remain so that essentially everyone is at least theoretically capable of mounting an autoimmune response. This observation implies that under normal circumstances potentially auto-aggressive cells are held in check by physiologic restraint mechanisms and that a contributor to the pathogenesis of autoimmunity is a failure of normal restraint mechanisms.

Examples of commonly encountered autoimmune disorders include but are not limited to: systemic lupus erythematosus, rheumatoid arthritis, type 1 diabetes, Guillain-Barré syndrome, other immune mediated neuropathies including chronic inflammatory demyelinating polyneuropathy, multiple sclerosis and other immune-mediated central nervous system demyelinating diseases, rheumatoid arthritis, Crohn's disease, ulcerative colitis, myasthenia gravis, scleroderma/systemic sclerosis, and dermatomyositis/polymyositis to name some of the more commonly encountered entities. Additional autoimmune diseases include acute glomerulonephritis, nephrotic syndrome, and idiopathic IgA nephropathy among autoimmune processes that affect the kidneys.

Examples of autoimmune processes that affect the formed elements of the blood are autoimmune aplastic anemia, autoimmune hemolytic anemia, and idiopathic thrombocytopenic purpura.

Autoimmune diseases that affect the endocrine organs include Addison's disease, idiopathic hypoparathyroidism, Grave's disease, Hashimoto's thyroiditis, lymphocytic hypophysitis, autoimmune oophoritis, and immunologic infertility in the male.

The liver may also be the target of autoimmune processes. Examples include autoimmune hepatitis, hepatitis C virus-associated autoimmunity, immunoallergic reaction drug-induced hepatitis, primary biliary cirrhosis, and primary sclerosing cholangitis.

Autoimmune processes of the intestinal tract include pernicious anemia, autoimmune gastritis, celiac disease, Crohn's disease, and ulcerative colitis.

Cutaneous autoimmune diseases include dermatitis herpetiformis, epidermolysis bullosa acquisita, alopecia totalis, alopecia areata, vitiligo, linear IgA dermatosis, pemphigus, pemphigoid, psoriasis, herpes gestationis, and cutaneous lupus including neonatal lupus erythematosus.

Additional autoimmune diseases with rheumatological features include CREST syndrome, ankylosing spondylitis, Behçet's disease, juvenile rheumatoid arthritis, Sjögren's syndrome, and eosinophilia-myalgia syndrome.

Autoimmune diseases can affect the heart. Examples include myocarditis and idiopathic dilated cardiomyopathy, rheumatic fever, Chaga's disease and possibly some components of atherosclerosis.

There can be an autoimmune component to inflammatory diseases of the blood vessels. Examples include giant cell arteritis, Kawasaki's disease, Henoch-Schonlein purpura, polyarteritis nodosa, Goodpasture's syndrome, immune complex vasculitis, Wegener's granulomatosis, Churg-Strauss syndrome, Takayasu arteritis, necrotizing vasculitis, and anti-phospholipid antibody syndrome.

Autoimmune diseases of the central and peripheral nervous systems can occur as a remote effect of malignant tumors. Rarely these same entities occur in the absence of a tumor. Examples include the Lambert-Eaton syndrome, paraneoplastic myelopathy, paraneoplastic cerebellar degeneration, limbic encephalitis, opsoclonus myoclonus, stiff man syndrome, paraneoplastic sensory neuropathy, the POEMS syndrome, dorsal root ganglionitis, and acute panautonomic neuropathy.

Autoimmune diseases may affect the visual system. Examples include Mooren's ulcer, uveitis, and Vogt-Koyanagi-Harada syndrome.

Other autoimmune processes, or ones in which autoimmunity may contribute to disability, include interstitial cystitis, diabetes insipidus, relapsing polychondritis, urticaria, reflex sympathetic dystrophy, and cochleolabyrinthitis.

The list of autoimmune processes given above, while extensive, is not intended to be exhaustive. Rather it is intended to document that autoimmunity is a wide-ranging clinical phenomenon. Exemplary diseases in this field such as systemic lupus erythematosus, multiple sclerosis, the Guillain-Barré syndrome, and autoimmune thrombocytopenic purpura are discussed in further detail below, with a view to providing some understanding of the problems involved in the diagnosis and treatment of these debilitating and potentially fatal disorders.

1. Systemic Lupus Erythematosus (SLE)

Multiple organ systems are involved in SLE and the manifestations of the illness are protean. Non-erosive and generally non-deforming arthritis and photosensitive rashes occur cumulatively in more than 75% of cases while serositis, central nervous system (CNS) involvement, and renal involvement occur in about 50% of cases. Lymphopenia occurs in the great majority of unselected cases and is almost invariably present in active disease. Hemolytic anemia and thrombocytopenia occur in about 50% of cases. SLE may involve any organ in the body. Commonly affected organs include the skin, kidneys, serosal membranes, joints, heart, and the CNS. Pathologically, immune complexes are deposited in the glomeruli of the kidneys, and immunoglobulin deposits in the skin at dermal epidermal junctions are the rule. SLE is characterized by numerous autoantibodies of varying specificities of which antinuclear antibodies (ANA) are almost invariably present as are antibodies to native double stranded DNA and to denatured single stranded DNA. Such antibodies are useful in diagnosis. Fibrinoid deposits within blood vessels and on serosal surfaces are another pathologic feature.

The clinical manifestations of SLE are so varied that a list of diagnostic criteria to be fulfilled before a definitive diagnosis of the disease can be made has been developed. 14 criteria are listed, 4 or more of which must be satisfied for a diagnosis (Cohen et al. 1971). The criteria include facial erythema, discoid lupus rash, Raynaud's phenomenon, alopecia, photosensitivity, oral nasal or pharyngeal ulceration, arthritis without deformity, LE cells, false positive test for syphilis, proteinuria (>3.5 g./day), pleuritis, pericarditis, psychosis, convulsions, hemolytic anemia, leukopenia, and thrombocytopenia.

SLE is thought to be primarily an antibody-mediated disease. ANA and DNA antibodies are directed against nucleoproteins but there may be numerous additional autoantibodies directed against mitochondria, ribosomes, lysosomes, soluble cytoplasmic constituents, red cells, white cells, platelets, and clotting factors to name but some. Why these antibodies emerge remains unclear but a major thrust of treatment attempts in SLE is to lower autoantibody titers.

There is no specific treatment for SLE but several drugs are known to favorably alter the natural history of the disease (Lieberman et al. 1988; Steinberg and Steinberg, 1991; Vyse and Walport, 1993; Wilke et al. 1991; Miller, 1992; Lubbe et al. 1983; Silman et al. 1988). Accepted treatments include non-steroidal anti-inflammatory drugs (NSAIDs; Kimberly, 1988), analgesics, glucocorticoids, (Lube et al. 1983; Edwards et al., 1987), hydroxychloroquine, azathioprine (Silman et al. 1988), cyclophosphamide (Steinberg and Steinberg, 1991), plaquenil (Wallace, 1993) and atabrine. Nonetheless treatment remains less than optimal and the agents mentioned have numerous potentially deleterious side effects. Ultraviolet light is known to exacerbate symptoms of SLE. For this reason barrier creams are sometimes prescribed. It has been conceded by those of skill in the art that little has changed in the management of SLE in recent years (Venables, 1993). The present invention offers the prospect of better management of this disease.

The treatment and study of Ab regulation in SLE with immunoglobulin fusion proteins is contemplated in this invention. The fusion proteins of the instant invention offer several potential advantages for the study of Ab regulation in SLE. They more closely approximate the physiologic situation in vivo than cell activation via FcγR Abs such as anti-CD16. Previously, functional studies of the low affinity FcγR have utilized mAb directed at CD16, mAb directed against CD2 which uses the same pathway in NK cells as CD16, or heat aggregated Ig. Though these reagents activate the FcγR, there are limitations in their application to the study of receptor function. Anti-CD16 mAbs bind specific epitopes of CD16 and crosslink the receptor but there are problems with mAbs for long term therapy. Abs to CD16 exert different effects on NK cell function depending on their binding site. This suggests that their mechanism of action is far from physiologic. mAb bind small regions of the receptor while the natural ligand binds numerous sites on the receptor that act coordinately to regulate receptor function.

2. Multiple Sclerosis

This disease is characterized by destruction of CNS myelin and of the axons which myelin ensheathes. The illness most commonly begins with focal attacks of tissue destruction in the white matter of the CNS which cause loss of neuronal function and as one attack follows another progressively accumulating disability. After a time most multiple sclerosis patients experience a decline in the frequency of their attacks but this decline is accompanied by a shift in the natural history of the illness to a slow but inexorable worsening of their neurological disabilities. The switch from a relapsing-remitting course to a progressive one ultimately occurs in better than 80% of multiple sclerosis victims.

Multiple sclerosis is an inflammatory disease. Lymphocytes and macrophages move from the blood into the CNS and attack and destroy myelin and ultimately the myelin forming cells known as oligodendrocytes. The process is one of autoimmunity but the precise target within the CNS against which the immune response is directed remains unknown. There is a genetically determined predisposition to develop multiple sclerosis but there is compelling evidence that environmental factors have a role as well, though the nature of the environmental factors in cause remains unknown.

There have been advances in the treatment of multiple sclerosis in recent years. Three agents are approved for the treatment of MS. These are interferon beta1a, interferon beta1b, and glatiramer acetate. All three modulate immune responses in a manner that favorably alters the hitherto bleak natural history of MS. Unfortunately all three are only modestly effective and each has side effects that are often troublesome. The present invention offers the prospect of a more efficient and effective therapy for MS.

Experimental autoimmune encephalomyelitis (EAE) is a widely used animal model for MS and serves as a useful model for the study of autoimmune diseases. EAE is a disease of the central nervous system and may be induced in susceptible animals by immunization with neuroantigens. EAE may also be adoptively transferred from one animal to the next by the serial transfer of T cells reactive against encephalitogenic determinants of myelin proteins or by the injection of T cell clones reactive against encephalitogenic determinants of myelin proteins. Myelin proteins that may be targets of the autoreactive response include proteolipid apoprotein (PLP), myelin basic protein (MBP), and myelin oligodendrocyte protein (MOG). Depending on the type and strain of animal used, the mode of induction, and the neuroantigen administered, the disease may be acute and monophasic in nature, or alternatively chronic, or relapsing-remitting.

Affected animals develop flaccid tails, paralysis of the hindlimbs, and incontinence. In severe disease, movement of the forelimbs may also become impaired and animals may become moribund. Histological analysis of the CNS reveals an inflammatory cell infiltrate during the acute stages of disease which may be accompanied by demyelination of the neurons during chronic phases of the disease. EAE is widely used for the study of autoimmune disease and serves as a model for testing potential efficacy of experimental drugs for the treatment of MS and for the treatment of autoimmune diseases in general.

The proteins of the current invention were tested for their effect on disease activity in a mouse model of EAE to gain insight into their potential use as therapeutics for the treatment of MS and other autoimmune diseases. As shown in Example 18, products of the current invention inhibited EAE in the SJL/J mouse. Administration of construct HSAR0 and in particular of HSAR4 decreased clinical disease activity during the early acute stages of disease and decreased the frequency of and severity of relapses at later time points as compared to saline-treated controls. Decreased inflammatory cell infiltrates were observed in the CNS of construct-treated animals compared to saline treated-controls.

3. Guillain-Barré Syndrome

The Guillain-Barré syndrome (GBS) comprises a group of autoimmune neuropathies of subacute onset in which the motor function of peripheral nerves is lost to a variable degree ranging from barely detectable weakness to total motor paralysis requiring ventilatory support. The most common form of the GBS syndrome in the occident follows, in most instances, an infectious illness that is usually respiratory or gastrointestinal. The peripheral nerves are invaded by T cells and macrophages which attack and destroy the myelin that ensheathes the nerve fibers. Loss of myelin impedes nerve impulse conduction and this causes weakness and, in extreme instances, paralysis. The process is ordinarily self-limited and myelin loss is followed by repair with restoration of function to variable degree. Treatment of the GBS syndrome is imperfect. Some benefit is obtained from plasmapheresis or the intravenous infusion of immunoglobulin but morbidity remains considerable and there is a need for better treatments. The present invention offers the prospect for improved therapy of the GBS syndrome.

A second form of the GBS syndrome is also recognized. This form occurs primarily in the orient. In this form motor weakness or paralysis are again seen but the autoimmune process is mediated by autoantibodies directed against glycolipids expressed on the surface of the nerve fibers themselves. In this form, as in the more commonly encountered form, favorable response to plasmapheresis or to intravenously administered immunoglobulin is sometimes seen.

4. Autoimmune (Idiopathic) Thrombocytopenic Purpura (ATP)

In this autoimmune disease platelets are destroyed by autoantibodies directed against antigens present on the individual's own platelet membrane. The disease may present as an acute process or as a chronic one. The acute process primarily affects young children without a sex preference. The chronic process usually affects adults in the third to fifth decades and shows a 3:1 female preponderance. Common clinical features observed when the platelet count falls below 10,000 include petechiae, purpura, gingival bleeding, epistaxis, and menorrhagia. Autoantibodies directed against glycoproteins expressed on the surface of platelets and their predecessors are demonstrable in the majority of patients. Platelets with surface bound IgG are largely cleared in the spleen by phagocytic macrophages that recognize damaged platelets via binding of IgG to the FcγRIIIa receptor expressed on macrophages. Resolution of thrombocytopenia has been reported following infusion of monoclonal antibody directed against the FcγRIIIa receptor (Clarkson et al. 1986). NK cell activity is reported as decreased in autoimmune thrombocytopenic purpura (Semple et al. 1991). The present invention binds to the FcγRIIIa receptor and activates NK cells and accordingly offers the prospect of more effective treatment for this autoimmune disease. Currently accepted treatments for ATP include glucocorticoids, and intravenous immunoglobulin, and when these fail to control the disease, as is unfortunately often the case, immunosuppresive and cytoxic agents may have to be administered despite their risks.

5. Diseases Favorably Effected by IgG Therapy

The inventors contemplate the therapeutic use of the fusion proteins of the current invention in any disease in which intravenous immunoglobulin has been previously used. Intravenous immunoglobulin has FDA approval for the treatment of ATP. The agent has been proven to be efficacious, based on double-blind controlled trials, in the treatment of the Guillain-Barré syndrome, myasthenia gravis and dermatomyositis. Intravenous immunoglobulin has been reported to be beneficial in more than 30 immunological diseases. The mechanisms for the beneficial effects in these diseases are currently unknown but may be mediated by various immunomodulating properties of intravenous immunoglobulin (Asghar et al., 1996; Dwyer et al., 1992; Geha et al., 1996; Yu et al., 1999). Some diseases in which immunoglobulins have been used for treatment are shown in Table 1 (http://www-.bioscience.org/2000/v5/e/asghar/fulltext.htm).

TABLE 1

Diseases in which beneficial effects of intravenous immunoglobulin have been demonstrated in small numbers (or groups) of patients

| Disease | References |
| --- | --- |
| Anemias of different types | Bjorkholm M.: Intravenous immunoglobulin treatment in cytopenic haematological disorders. J. Intern. Medicine. 234, 119-26 (1993).; Ballester O.F., H.I. Saba, L.C. Moscinski, R. Nelson & P. Foulis P: Pure red cell aplasia: treatment with intravenous immunoglobulin concentrate. Semin. Hematol. 29(Suppl 2),106-8 (1992) |
| Neutropenias of different types | Bjorkholm M.: Intravenous immunoglobulin treatment in cytopenic haematological disorders. J. Intern. Medicine. 234, 119-26 (1993).; Dunkel I.J. & J.B. Bussel: New |

TABLE 1-continued

Diseases in which beneficial effects of intravenous immunoglobulin have been demonstrated in small numbers (or groups) of patients

| Disease | References |
| --- | --- |
| | developments in the treatment of neutropenia. Am. J. Dis. Children 147,994-1000 (1993) |
| Multiple sclerosis | Lisak R.P.: Intravenous immunoglobulin in multiple sclerosis. Neurology 51 (Suppl 5), S25-29 (1998) |
| Sjögren's syndrome | Dupond JL., H. Gil, B. de Wazieres: Five-year efficacy of intravenous gamma globulin to treat dysautonomia in Sjögren's syndrome. Am. J. Medicine. 106,125, 1999; Durez P., L. Tourne, W. Feremans, F. Mascart-Lemone, M. Heenen & T. Appelboom: Dramatic response to intravenous high dose gamma-globulin in refractory vasculitis of the skin associated with Sjogren's syndrome J. Rheumatology 25, 1032-1033, 1998 |
| Cystic fibrosis | Rubin B.K: Emerging therapies for cystic fibrosis lung disease. Chest 115, 1120-6 (1999) |
| Thyroid related eye disease | Baschieri L., A. Antonelli, S. Nardi, B. Alberti, A. Lepri, R. Canapicchi & P. Fallahi: Intravenous immunoglobulin versus corticosteroid in treatment of Graves' ophthalmopathy. Thyroid 7, 579-85, (1997) |
| Uveitis | Rosebaum J.T., R.K. George & C. Gordon: The treatment of refractory uveitis with intravenous immunoglobulin. Am. J. Ophthalmol. 127, 545-9 (1999) |
| Asthma | Kon O.M & N. Barnes: Immunosuppressive treatment in asthma. Br. J. Hospital. Med. 57, 383-386 (1997); Balfour-Lynn I.: Difficult asthma. Beyond the guidelines. Arch. Dis. Childhood 80, 201-206 (1999) |
| Ulcerative and Crohn's disease | Levine D.S., S.H. Fischer, D.L. Christie, R.C. Haggitt & H.D. Ochs: Intravenous immunoglobulin therapy for active, extensive, and medically refractory idiopathic ulcerative or Crohn's colitis. Am. J. Gastroenterol. 87, 91-100 (1992) |
| Pyoderma gangrenosum | Gupta A.K., N.H. Shear & D.N. Sauder: Efficacy of human intravenous immune globulin in pyoderma gangrenosum. J. Am. Acad. Dermatol. 32, 140-142 (1995) |

G. Biological Functional Equivalents

As modifications and/or changes may be made in the structure of the polynucleotides and and/or proteins of the present invention, while obtaining molecules having similar or improved characteristics, such biologically functional equivalents are also encompassed within the present invention.

1. Modified Polynucleotides and Polypeptides

The biological functional equivalent may comprise a polynucleotide that has been engineered to contain distinct sequences while at the same time retaining the capacity to encode the "wild-type" or standard protein. This can be accomplished owing to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide can be engineered to contain certain sequences that result in (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges on the protein's ability to carry out its designated function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity, such as binding to FcγRs. Biologically functional equivalents are thus defined herein as those proteins (and polynucleotides) in which selected amino acids (or codons) may be substituted.

In general, the shorter the length of the molecule, the fewer the changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all of similar size; and/or that phenylalanine, tryptophan and/or tyrosine all have a generally similar shape. Therefore, based upon these considerations, arginine, lysine and/or histidine; alanine, glycine and/ or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

2. Codons

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

TABLE 2

CODON TABLE

| Amino Acids | | | Codons |
|---|---|---|---|
| Alanine | Ala | A | GCA GCC GCG GCU |
| Cysteine | Cys | C | UGC UGU |

TABLE 2-continued

CODON TABLE

| Amino Acids | | | Codons |
|---|---|---|---|
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The term "functionally equivalent codon" is used herein to refer to codons that encode the same amino acid, such as the six codons for arginine or serine, and also refers to codons that encode biologically equivalent amino acids (see Codon Table, above).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table of exemplary, but not limiting, modified and/or unusual amino acids is provided herein below.

TABLE 3

Modified and/or Unusual Amino Acids

| Abbr. | Amino Acid |
|---|---|
| Aad | 2-Aminoadipic acid |
| BAad | 3- Aminoadipic acid |
| BAla | beta-alanine, beta-Amino-propionic acid |
| Abu | 2-Aminobutyric acid |
| 4Abu | 4- Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| HyL | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

4. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and highly permissive for mutation. This motif is composed of a beta sheet and an alpha helix bridged in the interior core by three disulfides.

Beta II turns have been mimicked successfully using cyclic L-pentapeptides and those with D-amino acids. (Weisshoff et al.,1999). Also, Johannesson et al. (1999) report on bicyclic tripeptides with reverse turn-inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

H. Proteinaceous Compositions

In certain embodiments, the present invention concerns novel compositions comprising at least one proteinaceous molecule, such as a fusion protein with multiple HCH2 regions. As used herein, a "proteinaceous molecule", "proteinaceous composition", "proteinaceous compound", "proteinaceous chain" or "proteinaceous material" generally refers to, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative, or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown in Table 3.

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Organisms include, but are not limited to, a bovine, a reptilian, an amphibian, a piscine, a rodent, an avian, a canine, a feline, a fungus, a plant, an archebacteria, or a prokaryotic organism, with a selected animal or human subject being preferred. Such untoward or undesirable effects are those such as significant toxicity or adverse immunological reactions. In preferred embodiments, biocompatible protein, polypeptide or peptide containing compositions will generally be mammalian proteins or peptides, or synthetic proteins or peptides, each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

In certain embodiments a proteinaceous compound may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Polypeptide regions of proteinaceous compounds may be linked via a linker group. A linker group is able to join the compound of interest via a biologically-releasable bond, such as a selectively-cleavable linker or amino acid sequence.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived from or obtained from an organism. Organisms that may be used include, but are not limited to, a bovine, a reptilian, an amphibian, a piscine, a rodent, an avian, a canine, a feline, a fungus, a plant, or a prokaryotic organism, with a selected animal or human subject being preferred. The "autologous protein, polypeptide or peptide" may then be used as a component of a composition intended for application to the selected animal or human subject. Preferably it is biocompatible (i.e. from mammalian origin for mammals, preferably from human origin for humans, from canine origin for canines, etc.; it is autologous; it is non-allergenic, and/or it is non-immunogenic).

I. Mechanisms of Action and Applications

Autoimmune disease often involves both T-cell and B-cell mediated components that may act dependently or independently of one another, simultaneously or sequentially, resulting in a host-damaging disease often characterized by tissue or cell compromise and a loss of one or more bodily functions. Fc receptors and proteins of the complement cascade are often intimately associated with the generation of the autoimmune response, the regulation of the ongoing immune response, and the effector phase of the immune response (i.e. those mechanisms that lead to tissue or cell destruction or damage). The fusion proteins of the current invention, through their ability to bind Fc receptors and/or complement, may influence disease outcome by their impact upon one or more of these areas.

The fusions proteins of the current invention may favorably alter disease activity by multiple pathways depending on the fusion protein design and type of disease treated. Fusion proteins of the current invention may be designed to contain; multiple units of HCH2 regions, or portions thereof, able to bind Fc receptors, multiple units of HCH2 regions able to bind complement components, or both. It is contemplated that the fusion protein design can be modified to maximize potential benefits achieved from its use in treating a specific disease and its composition may vary from one disease to the next. For example, for the treatment of some diseases it may be preferable to retain the Fc receptor binding ability of the fusion proteins but exclude or diminish binding of components of the complement cascade. The obverse may be preferred for the treatment of other diseases.

The effect of the fusion proteins on disease outcome will depend not only on whether they contain multiple units able to bind Fc receptors, multiple units able to bind complement components, or both, but also on other protein domains that may be coexpressed in the fusion proteins to give them an additional function, binding capability, or other added feature. An additional modification to the fusion proteins of the current invention includes the binding of additional proteins, protein domains, or peptides to the fusion proteins that give them an additional function, binding capacity, or other added feature. The flexibility in the fusion protein design enables the inventors to, depending on disease type, modify the fusion proteins of the current invention to maximize their therapeutic potential. It is an embodiment of the current invention that in addition to the treatment of autoimmunity, modifications of the fusion proteins as described above are applicable to their use in the treatment of neoplasms, the treatment of infections by viruses or other pathogens, the treatment of warts, and the purposeful induction of an immune response directed against a particular antigen or antigens.

Fusion proteins able to bind Fc receptors may influence disease outcome through multiple mechanisms including but not limited to blocking Fc receptor accessibility to endogenously produced Ig and immune complexes. Such blockade would be expected to limit self-antigen presentation by antigen presenting cells and to, as a consequence, diminish autoimmune responses. Blockade of Fc receptors may also limit or diminish tissue and cell destruction. Tissue and cell destruction in autoimmune disease is often mediated by Fc receptor-expressing effector cells (monocytes, neutrophils, macrophages, microglia, NK cells, as well as other cell types) that bind self-antigen reactive Ig bound to tissue or cells. For example, in ATP, the fusion proteins of the current invention could limit platelet destruction and clearance by the body by decreasing their uptake by Kupffer cells in the liver and spleen via Fc receptor-mediated mechanisms. Similarly fusion proteins might limit demyelination in the CNS in multiple sclerosis or acetylcholine receptor destruction of motor neural endplates in myasthenia gravis by decreasing macrophage accessibility to Ig bound to self Ag in target tissues. The fusion proteins may favorably alter numerous autoimmune diseases via similar mechanisms.

The fusion proteins of the current invention may modify autoimmune disease by activating cells through Fc receptors and thereby altering the secretion of immunomodulators, the expression of specific cell surface markers, or the type or magnitude of specific cell functions. Modulation of protein secretion might include the decreased or increased production of interleukins including but not limited to IL-2, IL-4, IL-10, IL-12, IL-18; cytokines including but not limited to TGFβ, TNFα, TNFβ; interferons γ, β, and α; growth factors, and products of the arachidonate cascade. Cellular functions that may be altered include cellular cytotoxicity, cell division, and activation state.

The fusion protein(s) of the current invention may also be used to suppress or amplify immunity to a specific antigen. Autoimmune disease may be treated by inducing tolerance to a specific antigen or by deviating the autoimmune response to a specific antigen from a harmful pathogenic one to a less harmful type. For example, in multiple sclerosis the elaboration of type 1 cytokines (IL-12, IL-2) in response to autoantigen is generally thought to be deleterious to the host while induction of a type 2 response (IL-4, IL-10) is thought to be protective. The purposeful deviation of the immune response from a Th1 type to a Th2 type would likely be beneficial in the treatment of multiple sclerosis. In contrast, a Th2 type response is thought to be harmful in other autoimmune diseases such as lupus erythematosus, and consequently the purposeful deviation of the response to autoantigen in this disease from a Th2 type response to a Th1 type response would likely be beneficial. Thus, modification of the fusion proteins of the current invention would vary depending on the disease type and the mechanisms involved.

It is an embodiment of the current invention to coexpress one or more protein domains of a specific antigen or bind one or more specific antigens or antigenic determinants to the fusion protein that would induce a protective immune response, deviate a harmful immune response to a less harmful one, or induce a state of nonresponsiveness to antigen (Lasalle et al., 1994). For example, the inventors contemplate, in the treatment of multiple sclerosis, to coexpress a neuroantigen peptide in the fusion protein that induces a protective Th2 type response or an unresponsive state. A nonlimiting list of potential neuroantigens that might be used for the treatment of multiple sclerosis include proteolipid protein, myelin basic protein and myelin oligodendrocyte glycoprotein. Similarly, a T cell receptor or Ig domain may be expressed in the fusion protein that would induce a protective anti-T cell receptor or anti-idiotype response. The inventors contemplate that varying the protein coexpressed based upon disease type should allow the fusion protein of the current invention to be used for the treatment of numerous autoimmune diseases.

As mentioned earlier, the adaptive immune system is often referred to as having two components, cellular immunity (or Th1 type response) and humoral immunity (or Th2 type response). Response to an antigen evokes one or both of these components. Immunomodulators such as lymphokines and monokines that promote one component often inhibit the other. Thus a strong cellular response will often occur in the presence of a blunted humoral response and vice versa. Factors important to the development of one or the other response include the presence or absence of cytokines, costimulatory factors, as well as other factors that are known to those familiar in the art (Lasalle et al., 1994). For example the presence of IL-4 has been shown to enhance a Th2 type response while the presence of interferon gamma induces a Th1 type response (Swain et al,. 1988). In the treatment of autoimmune disease, neoplasms, or viral infections, or in the induction of immunity to pathogens by vaccine based therapies, it may be preferable to selectively modulate one or both of these components. The coadministration of cytokines, steroids, or other immunomodulators may be preferred in the treatment of varying diseases or when attempting to induce immunity to an antigen or antigens based upon the type of response desired.

J. Recombinant HCH2 Polymer Constructs in Immune Therapy for Cancer and Infection.

In another embodiment of the invention, a HCH2 polymer fusion protein can be constructed to specifically target cells. In one embodiment, the fusion protein of this invention can be constructed to target neoplastic cells, malignant cells that make up the tumor, or cancer cells. Neoplastic cells, cancer cells, or the malignant cells that make up the tumor may be targeted using a ligand or bispecific ligand that has a region capable of binding to a relatively specific marker of the tumor cell. In a specific embodiment, the fusion protein of this invention binds the target cell directly using a Fab' fragment or Fab' fragments covalently attached to the polymer by genetic or chemical means. Another aspect of the invention includes using a HCH2 fusion protein to target a delivery site comprising neoplastic cells for the delivery of a toxin. Toxins kill the neoplastic cells. Another aspect of the invention includes using a HCH2 fusion protein to target a delivery site comprising neoplastic cells for the delivery of a therapeutic agent. Similarly the HCH2 fusion proteins of the invention can be used to target cells for the treatment of pathogenic conditions resulting from infections from bacterial, protozoan, fungal, mycoplasma, rickettsia, and viral agents.

HCH2 polymers are polyvalent resulting in high functional affinity for the binding to and activation of Fc receptors. Additionally, certain preparations of HCH2 polymers can bind multiple complement components, thus triggering complement activation cascades. Using alterations to the HCH2 monomer unit that are well known in the art, HCH2 polymers can be produced for the specific binding to Fc receptors, for the specific binding to complement factors, or for binding to both Fc receptors and complement factors simultaneously. HCH2 polymers fused to mono- or bi-specific Fab fragments or other binding domains described herein result in molecules with multispecific binding determinants. Based on their ability to engage complement and/or FcR on immune cells as well as to bind one or more antigens expressed on target cells, a particular embodiment of the HCH2 polymers can be used to treat or prevent the reoccurrence of neoplastic diseases including cancer. Similarly the HCH2 polymers of the invention can be used to treat pathologic conditions resulting from infections from bacterial, protozoan, fungal, rickettsial, and viral agents.

HCH2 polymers can direct destruction or removal of target cells by any one or combination of antibody-mediated cellular effector mechanisms. HCH2 polymers can induce target cell killing through antibody-dependent cell-mediated cytotoxicity (ADCC). ADCC is triggered when HCH2 polymers, bound to target cells, cross-link and aggregate FcγR expressed on immune cells such as NK cells. Once the FcγR on NK cells are engaged, for example, they trigger a series of events that result in the perforin mediated lysis of target cell membranes, lysosomal enzyme release and cytotoxic superoxide generation. Activation of FcγR on monocytes/macrophages, which express all three classes of FcγR, can lead to phagocytosis of intact cells as well as release of soluble cytotoxic factors. For example, bispecific antibodies that target FcγR and erbB-2 protein are known in the art. The erbB-2 protein is over-expressed in cancers of the breast, ovary and other cancers. MDX-H210 is a bispecific antibody constructed through the chemical cross-linking of a F(ab') fragment that recognizes FcγRI (high affinity Fc receptor) to a fragment that recognizes the erbB-2 protein. ADCC mediated tumor cell killing is postulated to proceed as a result of ligation of tumor cell-bound antibody to FcγRI receptors expressed on macrophages (Cumow, 1997).

Complement activation is the other major antibody-mediated pathway for clearance of target cells. HCH2 polymers can induce target cell killing through complement-dependent cytotoxicity (CDC). CDC begins with the binding of C1q to HCH2 regions (Fc regions) bound to target cell antigens. Binding of C1q leads to classical complement pathway activation ultimately resulting in the formation of the membrane attack complex (factors C5b-9) and disruption of the cell membrane. Classical pathway activation is not cell-mediated, depending only on circulating complement factors. In addition to CDC, target cell killing can be induced through complement-dependent cellular cytotoxicity (CDCC). CDCC begins with the binding of C1q to the complement binding site within the HCH2 region. Other complement factors, such as C3b and C4b, are subsequently deposited and these trigger enhanced phagocytosis and cytotoxic killing by macrophages, polymorphonulear leukocytes and NK cells. CDC has been identified as a major effector mechanism by which the therapeutically administered monoclonal antibody Rituximab exerts its effects in the treatment of low grade non-Hodgkin's lymphoma (Harjunpää et al.,2000).

The fusion proteins of the current invention offer several potential advantages for Fc receptor-mediated killing of target cells in addition to those already discussed for monoclonal antibodies or fragments of monoclonal antibodies in current use. The number of HCH2 units contained in the polymer region can be altered to hone interaction with FcR and/or with complement. Secondly, use of the Fc region of the antibody to target FcR opens up the F(ab)2 region for targeting to two additional epitopes, resulting in a molecule that is trispecific. The additional specificity allows for precise targeting to cells of interest. Thirdly, alteration of the HCH2 unit within the polymer region permits specific engagement of FcR only, complement only, or both. In addition, the HCH2 polymer interacts with FcR in a manner identical to that of immune complexes. This may provide a qualitatively different signal to cytotoxic effector cells than results from binding of monoclonal antibody to epitopes outside the ligand binding site on FcR.

As described herein, HCH2 fusion proteins can be constructed to specifically target cells expressing tumor antigens. Neoplastic cells or the malignant cells that make up a tumor may be targeted using a ligand or bispecific ligand that has a region capable of binding to a relatively specific marker of the tumor cell. The fusion proteins of this invention can be constructed to target neoplastic cells. Another aspect of the invention includes using HCH2 fusion proteins to target a delivery site comprising neoplastic cells for the delivery of a therapeutic agent.

1. Neoplastic Cell Targets

Many so-called "tumor antigens" have been described, any one of which could be employed as a target in connection with the combined aspects of the present invention. A large number of exemplary solid tumor-associated antigens are listed herein below. The preparation and use of antibodies against such antigens is well within the skill of the art, and exemplary antibodies include from gynecological tumor sites: OC 125; OC 133; OMI; Mo v1; Mo v2; 3C2; 4C7; $ID_3$; DU-PAN-2; F 36/22; $4F_7/7A_{10}$; OV-TL3; B72.3; $DF_3$; $2C_8/2F_7$; MF 116; Mov18; CEA 11-H5; CA 19-9 (1116NS 19-9); H17-E2; 791T/36; $NDOG_2$; H317; 4D5, 3H4, 7C2, 6E9, 2C4, 7F3, 2H11, 3E8, 5B8, 7D3, SB8; HMFG2; 3.14.A3; from breast tumor sites: DF3; NCRC-11; 3C6F9; MBE6; CLNH5; MAC 40/43; EMA; HMFG1 HFMG2; 3.15.C3; M3, M8, M24; M18; 67-D-11; D547Sp, D75P3, H222; Anti-EGF; LR-3; TA1; H59; 10-3D-2; HmAB1,2; MBR 1,2,3; 24.17.1; 24.17.2 (3E1.2); F36/22.M7/105; C11, G3, H7; B6.2; B1.1; Cam 17.1; SM3; SM4; C-Mul (566); 4D5 3H4, 7C2, 6E9, 2C4, 7F3, 2H11, 3E8, 5B8, 7D3, 5B8; OC 125; MO v2; DU-PAN-2; $4F_7/7A_{10}$; $DF_3$; B72.3; cccccCEA 11; H17-E2; 3.14.A3; FO23C5; from colorectal tumor sites: B72.3; (17-1A) 1083-17-1A; CO17-1A; ZCE-025; AB2; HT-29-15; 250-30.6; 44X14; A7; GA73.3; 791T/36; 28A32; 28.19.8; X MMCO-791; DU-PAN-2; $ID_3$; CEA 11-H5; $2C_8/2F_7$; CA-19-9 (1116NS 19-9); PR5C5; PR4D2; PR4D1; from melanoma sites 4.1; 8.2 $M_{17}$; 96.5; 118.1, 133.2, (113.2); $L_1$, $L_{10}$, $R_{10}$ ($R_{19}$); $I_{12}$; $K_5$; 6.1; R24; 5.1; 225.28S; 465.12S; 9.2.27; F11; 376.96S; 465.12S; 15.75; 15.95; Me1-14; Me1-12; Me3-TB7; 225.28SD; 763.24TS; 705F6; 436910; M148; from gastrointestinal tumors: ID3; DU-PAN-2; OV-TL3; B72.3; CEA 11-H5; 3.14.A3; C COLI; CA-19-9 (1116NS 19-9) and CA50; OC125; from lung tumors: 4D5 3H4, 7C2, 6E9, 2C4, 7F3, 2H11, 3E8, 5B8, 7D3, SB8; MO v2; B72.3; DU-PAN-2; CEA 11-H5; MUC 8-22; MUC 2-63; MUC 2-39; MUC 7-39; and from miscellaneous tumors: PAb 240; PAb 246; PAb 1801; ERIC.1; M148; FMH25; 6.1; CA1; 3F8; $4F_7/7A_{10}$; $2C_8/2F_7$; CEA 11-H5.

Another means of defining a targetable tumor is in terms of the characteristics of a tumor cell itself, rather than describing the biochemical properties of an antigen expressed by the cell. Accordingly, the skilled artisan is referred to the ATCC catalogue for the purpose of exemplifying human tumor cell lines that are publicly available (from ATCC Catalogue). Exemplary cell lines include J82; RT4; ScaBER; T24; TCCSUP; 5637; SK-N-MC; SK-N-SH; SW 1088; SW 1783; U-87 MG; U-118 MG; U-138 MG; U-373 MG; Y79; BT-20; BT-474; MCF7; MDA-MB-134-VI; MDA-MD-157; MDA-MB-175-VII; MDA-MB-361; SK-BR-3; C-33 A; HT-3; ME-180; MS751; SiHa; JEG-3; Caco-2; HT-29; SK-CO-1; HuTu 80; A-253; FaDu; A-498; A-704; Caki-1; Caki-2; SK-NEP-1; SW 839; SK-HEP-1; A-427; Calu-1; Calu-3; Calu-6; SK-LU-1; SK-MES-1; SW 900; EB1; EB2; P3HR-1; HT-144; Malme-3M; RPMI-7951; SK-MEL-1; SK-MEL-2; SK-MEL-3; SK-MEL-5; SK-MEL-24; SK-MEL-28; SK-MEL-31; Caov-3; Caov-4; SK-OV-3; SW 626; Capan-1; Capan-2; DU 145; A-204; Saos-2; SK-ES-1; SK-LMS-1; SW 684; SW 872; SW 982; SW 1353; U-2 OS; Malme-3; KATO III; Cate-1B; Tera-1; Tera-2; SW579; AN3 CA; HEC-1-A; HEC-1-B; SK-UT-1; SK-UT-1B; SW 954; SW 962; NCI-H69; NCI-H128; BT-483; BT-549; DU4475; HBL-100; Hs 578Bst; Hs 578T; MDA-MB-330; MDA-MB-415; MDA-MB-435S; MDA-MB-436; MDA-MB-453; MDA-MB-468; T-47D; Hs 766T; Hs 746T; Hs 695T; Hs 683; Hs 294T; Hs 602; JAR; Hs 445; Hs 700T; H4; Hs 696; Hs 913T; Hs 729; FHs 738Lu; FHs 173We; FHs 738B1; NIH:0VCAR-3; Hs 67; RD-ES; ChaGo K-1; WERI-Rb-1; NCI-H446; NCI-H209; NCI-H146; NCI-H441; NCI-H82; H9; NCI-H460; NCI-H596; NCI-H676B; NCI-H345; NCI-H820; NCI-H520; NCI-H661; NCI-H510A; D283 Med; Daoy; D341 Med; AML-193 and MV4-11.

One may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature will thus readily reveal an appropriate choice of cell for any tumor cell type desired to be targeted.

Recent technological advances enable those familiar in the art to rapidly and efficiently compare gene expression in neoplastic tissue to that of normal tissue. These technological advances include but are not limited to differential gene analysis using gene chip arrays and protein arrays. Using these technologies one is able to compare mRNA species and proteins expressed in neoplastic tissue to that found in normal tissue. Those mRNA species or proteins that are differentially expressed in neoplastic tissue compared to normal tissue may be readily discerned. Proteins found to be preferentially expressed in neoplastic tissue or in neoplastic cells using these screening technologies serve as likely candidates for the further development of cancer or tumor specific therapies. It is an embodiment of the current invention that tumor associated proteins or tumor specific proteins discovered using these technologies may be employed as targets in connection with the combined aspects of the present invention.

2. Anti-Tumor Cell Antibodies

A straightforward means of recognizing a tumor antigen target is through the use of an antibody that has binding affinity for the particular antigen. An extensive number of antibodies are known that are directed against solid tumor antigens. Certain useful anti-tumor antibodies are listed above. However, as will be instantly known to those of skill in the art, certain of the antibodies listed will not have the appropriate biochemical properties, or may not be of sufficient tumor specificity, to be of use therapeutically. An example is MUC8-22 that recognizes a cytoplasmic antigen. Antibodies such as these will generally be of use only in investigational embodiments, such as in model systems or screening assays.

Generally speaking, antibodies for use in these aspects of the present invention will preferably recognize antigens that are accessible on the cell-surface and that are preferentially, or specifically, expressed by tumor cells. Such antibodies will also preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity", as used herein, refers to an antibody or antibody fragment, that, when applied to the particular tissue under conditions suitable for immunohistochemistry, will elicit either no staining or negligible staining with only a few positive cells scattered among a field of negative cells.

Another means of defining a tumor-associated target is in terms of the characteristics of the tumor cell, rather than describing the biochemical properties of an antigen expressed by the cell. Accordingly, the inventors contemplate that any antibody that preferentially binds to a tumor cell may be used as the targeting component of an immunotoxin or coaguligand. The preferential tumor cell binding is again based upon the antibody exhibiting high affinity for the tumor cell and not having significant reactivity with life-sustaining normal cells or tissues, as defined above.

To generate a tumor cell-specific antibody, one would immunize an animal with a composition comprising a tumor cell antigen and, as described more fully below, select a resultant antibody with appropriate specificity. The immunizing composition may contain a purified, or partially purified, preparation of any of the antigens listed above; a composition, such as a membrane preparation, enriched for any of the antigens listed above; any of the cells listed above; or a mixture or population of cells that include any of the cell types listed above.

Of course, regardless of the source of the antibody, in the practice of the invention in human treatment, one will prefer to ensure in advance that the clinically-targeted tumor expresses the antigen ultimately selected. This is achieved by means of a fairly straightforward assay involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinities of antibodies from a "bank" of hybridomas are tested for reactivity against the tumor. Antibodies demonstrating appropriate tumor selectivity and affinity are then selected for the preparation of bispecific antibodies of the present invention.

Due to the well-known phenomenon of cross-reactivity, it is contemplated that useful antibodies may result from immunization protocols in which the antigens originally employed were derived from an animal, such as a mouse or a primate, in addition to those in which the original antigens were obtained from a human cell. Where antigens of human origin are used, they may be obtained from a human tumor cell line, or may be prepared by obtaining a biological sample from a particular patient in question. Indeed, methods for the development of antibodies that are "custom-tailored" to the patient's tumor are known (Stevenson et al., 1990) and are contemplated for use in the fusion proteins of this invention.

3. Further Tumor Cell Targets and Binding Ligands

In addition to the use of antibodies, other ligands could be employed to direct a HCH2 fusion protein to a tumor site by binding to a tumor cell antigen. For tumor antigens that are over-expressed receptors (e.g. estrogen receptor, EGF receptor), or mutant receptors, the corresponding ligands could be used as targeting agents.

K. HCH2 Polymers in Antigen Presentation to Antigen Presenting Cells (APC).

In another embodiment of the invention, the polymers of this invention will be linked to an antigen. As used herein, the term "antigen" means any natural or synthetic immunogenic substance, a fragment or portion of an immunogenic substance, a peptide epitope, or a hapten (as defined in U.S. Pat. No. 5,922,845, p 13). In one embodiment, the polymers of the invention are used to target an antigen to the cell to enhance the process of internalization and presentation of the antigen by these cells, and ultimately to stimulate an immune response. In another embodiment, the polymers of the invention specifically bind the antigen directly or bind to epitopes attached to the antigen, e.g., a cloned Fab' fragment covalently attached to the polymer by genetic or chemical means which recognizes the antigen or epitopes attached to the antigen, and targets the bound antigen to antigen presenting cells (APC) for internalization, processing, and presentation. In another embodiment, the antigen is linked to the polymers of the invention and at the same time binds a surface receptor of an antigen-presenting cell. In a preferred embodiment the antigen is covalently attached to the polymers of the invention by genetic or chemical means.

More broadly, the polymers of this invention will be linked to a cell surface marker. A cell surface marker is a protein, carbohydrate, glycolipid, etc. but most commonly comprises a protein localized to the plasma membrane of a cell having a portion exposed to the extracellular region (e.g. an integral membrane protein or a transmembrane glycoprotein), such that the extracellular portion can be specifically bound by an antibody or other ligand. The term cell surface marker also refers to a polynucleotide sequence encoding such a cell surface protein. Numerous cell surface proteins can be used as cell surface markers, such as, for example, a CD (cluster of differentiation) antigen present on cells of hematopoietic lineage (CD2, CD4, CD8, CD21), Gamma-glutamyltranspeptidase, an adhesion protein (ICAM-1, ICAM-2, ELAM-1, VCAM-1), a hormone, a growth factor, a cytokine receptor, ion channels, and the membrane-bound form of an immunoglobulin chain.

1. HCH2 Polymers for Use in Vaccines.

Traditional vaccines consist of killed or attenuated pathogenic organisms or their products administered to develop an immune response. Drawbacks to the traditional approach include unwanted harmful immune responses, inoculation with potentially infectious pathogens, and poor immune responses. Typically these vaccines require co-administration of potent adjuvants to elicit effective antibody responses. Vaccines can be made more effective by delivering those antigenic determinants that are most likely to confer protective immunity. Early attempts to develop peptide based vaccines resulted in poor immune responses due in part to an inefficient presentation of antigen by APCs.

APCs capture, internalize and present antigen. In addition they provide important costimulatory signals to T-cells. T-cells, thus activated, are capable of stimulating the production of antibody-forming B cells. Monocytes, especially macrophages and dendritic cells, function as APC. Macrophages express all three classes of FcγR constitutively whereas dendritic cells express FcγRI and FcγRII.

Dendritic cells (DCs) are highly specialized and are potent APCs for T-cells. As a result of this capacity DCs are often referred to as 'professional APCs'. DCs present antigen efficiently on both MHC I and HMC II resulting in the initiation of CD8+ and CD4+ responses respectively. DCs can prime naive T-cells. Subsequent to activation by DCs, T-cells can interact with other APC. DCs have a proliferative immature stage followed by terminal differentiation into a non-proliferative mature stage. Immature DCs express FcγRI and FcγRII, are capable of internalizing and presenting antigen, and synthesize large amounts of MHC II. In contrast mature DCs no longer express FcγRs, become fully active APCs, activate T-cells, and secrete large amounts of IL-12 (which spurs differentiation of T-cells). DCs are a more potent APC than macrophages though much less numerous.

There has been great interest in the enhancement of antigen presentation by targeting antigen to FcγR expressed on APCs. Known in the art are peptide vaccines wherein antigenic determinants are grafted into the variable region of IgG. These 'antigenized-antibodies' increased the half-life of antigen and facilitated uptake of antigen by APCs via the FcγRI receptor (Zaghouani et al., 1993; Zanetti et al., 1992). Use of antigenized-antibodies have been shown to be more effective at priming antigen specific T-cell responses than peptide alone. Antigenized-antibodies have several limiting features: Since they are directed towards FcγRI alone, they can be effectively competed against by monomeric serum IgG. Secondly, the design of the molecule limits the size of the antigenizing determinant to a small peptide fragment.

More recently antigen has been expressed as a fusion protein with or chemically conjugated to monoclonal antibodies and Fab fragments directed against FcγRI and FcγRII (Liu et al., 1996b; Guyre et al., 1997). Using tetanus toxoid epitopes conjugated to anti-FcγRI monoclonal antibody, one group found that peptides directed to FcγRI were 100 to 1000 fold more efficient than peptide alone in T-cell stimulation (Liu et al., 1996a). However, use of anti-FcγRI Fab' required chemical cross-linking to achieve maximal responses to antigen, thus implicating the low affinity IgG receptors (Keler et al., 2000). Disadvantages of this approach include the promiscuous binding of antigen-linked monoclonal antibody to FcγRI expressed on non-APCs. Monoclonal antibodies trigger effector functions poorly. Fab' fragments have the additional disadvantage of a short half-life in the circulation.

Attachment of antigen to the HCH2 polymers described herein for the purpose of targeting APCs has distinct advantages over existing strategies. HCH2 polymers present antigen to low affinity receptors (FcγRII and FcγRIII), thus bypassing competition from monomeric serum IgG for binding to FcγRI. Additionally there is no need for chemical cross-linking as is necessary when using anti-FcγRI Fab'. HCH2 polymers imitate immune complexes. Antigen presented in the context of an immune complex may be a particularly appropriate substrate for APCs. Antigen-linked HCH2 polymers efficiently trigger effector functions that augment the immune response.

2. HCH2 Polymers in Tolerance Induction.

Immunologic tolerance is characterized by the selective lack of an immune response, including lack of a pathogenic immune response to a specific antigen even while leaving other responses of the immune system intact. Induction and maintenance of T cell unresponsiveness to a specific antigen may be achieved by several mechanisms that can be broadly summarized as: 1) clonal deletion; 2) anergy; and 3) suppression. Clonal deletion is a process of negative selection whereby T cells with high affinity for self-antigens are deleted in the thymus. Deletion is achieved by programmed cell death (apoptosis). This process of negative selection in the thymus is known as 'central tolerance'. Anergy represents a state of immune inactivation characterized by abolished proliferative and cytokine responses. It is induced in cells that previously responded to a given antigen and results in an unresponsive state upon re-stimulation with antigen. Since this mechanism acts upon mature T cells that have exited the thymus and reside in the peripheral compartments, this form of tolerance is termed 'peripheral tolerance'. Anergy is induced by any of a number of molecular events and need not be permanent: it can be reversed by certain cytokines. Three common anergy-inducive mechanisms are T cell receptor (TCR) stimulation without co-stimulatory signals, sub-optimal TCR stimulation even in the presence of co-stimulation, and the autocrine inhibitory actions of IL-10. Suppression of T cell function is a third mechanism by which T cell tolerance can be achieved. Suppression ensues when regulatory T cells are induced to exert "non-specific" suppressive effects on antigen-specific T cells in their vicinity. This microenvironmental effect is also referred to as 'bystander suppression'

B cell tolerance involves concepts and mechanisms similar but not identical to those encountered in T cell tolerance. In mature B cells tolerance can be induced through a block in Ig-receptor signaling which results in impaired expression of the B7 costimulatory molecules.

Induction of tolerance to either self- or foreign-antigens provides an important therapeutic approach to the treatment of allergies, autoimmune disease and host vs. graft disease (transplant rejection). In addition, the therapeutic potential of many foreign biologically active agents is limited by their immunogenicity. Tolerance induction represents one approach for the control of immune responses directed against biologically active foreign agents, thus improving their therapeutic potential. In most instances the antigen to be tolerized is presented orally, intradermally, or intravenously. The source of antigen can be in the form of a peptide, a protein, or nucleic acid which can express a peptide or protein. The antigen is then internalized by antigen presenting cells (APC) and presented on the surface of the cell, most typically as a MHC I-antigen complex or as a MHC II-antigen complex.

The HCH2 polymers of the current invention have several advantageous aspects for use as vehicles for tolerance induction. Antigen(s) linked to the HCH2 polymers by chemical or genetic means are targeted to Fc receptors expressed on APC such as macrophages, B cells, and dendritic cells (DC). Fc-receptor-mediated internalization results in processing and presentation of antigen at the cell surface—the key first step in tolerance induction.

Macrophages and DC express Fc receptors for both IgG and IgE. HCH2 polymers are expressible which bind both classes of Fc receptor simultaneously—coaggregation of different Fc receptor classes may have advantages over targeting a single class of receptor. Ligation of FcRs induces secretion of IL10 from certain immune cells and, as already noted, IL10 induces anergy in T cells. As is observed for immune complexes, binding of HCH2 polymers to FcRs may induce a pattern of cytokine secretion that deviates T cell immune responses from a TH1 type response to a TH2 type response. TH2 type T cells favor the establishment and maintenance of immune tolerance. Therefore, antigens linked to the HCH2 polymers can promote tolerance induction by both the efficient presentation of antigen to APC and the simultaneous induction of mechanisms that favor establishment of immune tolerance.

L. Toxins

For certain applications, it is envisioned that therapeutic or pharmacological agents will be attached to the HCH2 fusion proteins, particularly cytotoxic or otherwise anti-cellular agents having the ability to kill or suppress the growth or cell division of neoplastic cells. In general, an aspect of the invention contemplates the use of any pharmacological agent that can be conjugated to the HCH2 fusion proteins which has been constructed to target a specific region, and delivered in active form to the targeted cell. Exemplary anti-cellular agents include chemotherapeutic agents, radioisotopes as well as cytotoxins. In the case of chemotherapeutic agents, agents such as a hormone such as a steroid, an anti-metabolite such as cytosine arabinoside, fluorouracil, methotrexate or aminopterin; an anthracycline; mitomycin C; a vinca alkaloid; demecolcine; etoposide; mithramycin; or an anti-tumor alkylating agent such as chlorambucil or melphalan, will be particularly preferred. Other embodiments may include agents such as a cytokine, growth factor, bacterial endotoxin or the lipid A moiety of bacterial endotoxin.

In certain preferred embodiments, the immunotoxins will include generally a plant-, fungus- or bacterium-derived toxin, such as an A chain toxin, a ribosome inactivating protein, α-sarcin, aspergillin, restrictocin, a ribonuclease, diphtheria toxin or pseudomonas exotoxin, to mention just a few examples. The use of toxin-protein constructs is well known in the art of immunotoxins, as is their attachment to antibodies. Of these, a particularly preferred toxin will be a deglycosylated ricin A chain. Deglycosylated ricin A chain is preferred because of its extreme potency and long half-life.

1. Preparation of Targeting Agent-toxin Conjugates

While the preparation of immunotoxins is, in general, well known in the art (see, e.g., U.S. Pat. No. 4,340,535, and EP 44167, both incorporated herein by reference), the inventors are aware that certain advantages may be achieved through the application of certain preferred technology, both in the preparation of the immunotoxins and in their purification for subsequent clinical administration Additionally, while numerous types of disulfide-bond containing linkers are known which can successfully be employed to conjugate the toxin moiety with the targeting agent, certain linkers will generally be preferred over other linkers, based on differing pharmacological characteristics and capabilities. For example, linkers that contain a disulfide bond that is sterically "hindered" are to be preferred, due to their greater stability in vivo, thus preventing release of the toxin moiety prior to binding at the site of action. A wide variety of cytotoxic agents are known that may be conjugated to HCH2 polymers. Examples include numerous useful plant-, fungus- or even bacterium-derived toxins, which, by way of example, include various A chain toxins, particularly ricin A chain, ribosome inactivating proteins such as saporin or gelonin, α-sarcin, aspergillin, restrictocin, ribonucleases such as placental ribonuclease, diphtheria toxin, and pseudomonas exotoxin, to name just a few.

Depending on the specific toxin compound used as part of the fusion protein, it may be necessary to provide a peptide spacer operatively attaching the targeting agent and the toxin compound which is capable of folding into a disulfide-bonded loop structure. Proteolytic cleavage within the loop would then yield a heterodimeric polypeptide wherein the targeting agent and the toxin compound are linked by only a single disulfide bond. See, for example, Lord et al. (1992). An example of such a toxin is a Ricin A-chain toxin.

When certain other toxin compounds are utilized, a non-cleavable peptide spacer may be provided to operatively attach the targeting agent and the toxin compound of the fusion protein. Toxins which may be used in conjunction with non-cleavable peptide spacers are those which may, themselves, be converted by proteolytic cleavage, into a cytotoxic disulfide-bonded form (see for example, Ogata et al., 1990). An example of such a toxin compound is a Pseudonomas exotoxin compound.

Nucleic acids that may be utilized herein comprise nucleic acid sequences that encode a targeting agent of interest and nucleic acid sequences that encode a toxin agent of interest. Such target agent-encoding and toxin agent-encoding nucleic acid sequences are attached in a manner such that translation of the nucleic acid yields the targeting agent/toxin compounds of the invention.

2. Attachment of Other Agents to Targeting Agents

It is contemplated that most therapeutic applications of the additional immunotoxin aspects of the present invention will involve the targeting of a toxin moiety to a tumor cell. This is due to the much greater ability of most toxins to deliver a cell killing effect as compared to other potential agents. However, there may be circumstances, such as when the target antigen does not internalize by a route consistent with efficient intoxication by targeting agent/toxin compounds, such as immunotoxins, where one will desire to target chemotherapeutic agents such as anti-tumor drugs, other cytokines, antimetabolites, alkylating agents, hormones, and the like. The advantages of these agents over their non-targeting agent conjugated counterparts is the added selectivity afforded by the targeting agent, such as an HCH2 polymer fusion protein. One might mention by way of example agents such as steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to targeting agents, such as antibodies or antibody fusion protein, for specific delivery to tissues is well established (see, e.g., Ghose and Blair, 1987).

A variety of chemotherapeutic and other pharmacological agents have now been successfully conjugated to antibodies and shown to function pharmacologically (see, e.g., Vaickus et al., 1991). Exemplary antineoplastic agents that have been investigated include doxorubicin, daunomycin, methotrexate, vinblastine, and various others (Dillman et al., 1988; Pietersz et al., 1988). Moreover, the attachment of other agents such as neocarzinostatin (Kimura et al., 1983), macromycin (Manabe et al., 1984), trenimon (Ghose, 1982) and α-amanitin (Davis and Preston, 1981) has been described.

M. Bispecific Antibodies

The use of bispecific antibodies (BsAbs) is contemplated in the fusion proteins and the methods for treating disease and targeting delivery sites of the current invention. In general, the preparation of BsAbs is also well known in the art, as exemplified by Glennie et al. (1987).

BsAbs have also been developed particularly for use as immunotherapeutic agents. As mentioned earlier in conjunction with antigen-induction, certain of these antibodies were developed to cross-link lymphocytes and tumor antigens (Nelson, 1991; Wunderlich, et al., 1992). Examples include chimeric molecules that bind T cells, e.g., at CD3, and tumor antigens, and trigger lymphocyte-activation by physically cross-linking the TCR/CD3 complex in close proximity to the target cell (Staerz et al., 1985; Perez et al., 1985; 1986a; 1986b; Ting et al., 1988).

Indeed, tumor cells of carcinomas, lymphomas, leukemias and melanomas have been reported to be susceptible to BsAb-mediated killing by T cells (Nelson, 1991; Segal et al., 1992). These types of BsAbs have also been used in several Phase I clinical trials against diverse tumor targets. The bispecific cross-linking antibodies may be administered as described in references such as Kroesen et al. (1997); Bolhuis et al. (1992); and Nitta et al. (1990).

While numerous methods are known in the art for the preparation of BsAbs, the Glennie et al. (1987) method involves the preparation of peptic $F(ab'\gamma)_2$ fragments from the two chosen antibodies, followed by reduction of each to provide separate $Fab'\gamma_{SH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired $F(ab'\gamma)_2$ heteroconjugate.

Another method for producing BsAbs is by the fusion of two hybridomas to form a quadroma (Fanger et al., 1992; Nolan et al., 1990; Menard et al., 1989). As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use of an alternative assay for the isolation of a preferred quadroma.

In more detail, one method of quadroma development and screening involves obtaining a hybridoma line that secretes the first chosen MAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1\times10^{-7}$M to $1\times10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques (Galfre et al., 1981), or by using the protocol described by Clark et al. (1988). Briefly, $4.5\times10^7$ HAT-sensitive first cells are mixed with $2.8\times10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. BsAb-containing cultures are identified using, for example, a solid phase isotype-specific ELISA and isotype-specific immunofluorescence staining.

In identification embodiments, ELISA, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the BsAbs are purified away from other cell products. This may be accomplished by a variety of protein isolation procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 3.0 citrate buffer. The eluted fractions containing the BsAbs, are dialyzed against an isotonic buffer. Alternatively, the eluate is passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie blue. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

Furthermore, recombinant technology is now available for the preparation of antibodies in general, allowing the preparation of recombinant antibody genes encoding an antibody having the desired dual specificity. Thus, after selecting the monoclonal antibodies having the most preferred binding characteristics, the respective genes for these antibodies can be isolated, e.g., by immunological screening of a phage expression library (Oi and Morrison, 1986; Winter and Milstein, 1991; Marks et al., 1991). Then, through rearrangement of Fab coding domains, the appropriate chimeric construct can be readily obtained.

N. Combined Treatment

Combination of the fusion proteins of the current invention with other therapeutic agents is contemplated for use in the clinical treatment of various diseases that involve altering immunity, inflammation or neoplasms.

Naturally, before wide-spread use, animal studies and clinical trials will be conducted. The various elements of conducting a clinical trial, including patient treatment and monitoring, will be known to those of skill in the art in light of the present disclosure.

The present invention contemplates that the fusion proteins may be used in combination with other therapies. Therapies for autoimmune diseases include but are not limited to interferon-β, interferon-α, i.v. immunoglobulins, monoclonal antibodies such as h5G1.1-mAb, polyclonal antibodies such as anti-RhoD (WinRho SDF), retinoic acid and other immunomodulatory agents such as glatiramer acetate.

Therapies for diseases that involve inflammation include, but are not limited to non-steroidal inflammatory drugs (NSAIDs) such as cyclo-oxygenase 2 (COX-2) inhibitors.

The present invention contemplates that the fusion proteins may be used as an adjuvant in combination with vaccines. Vaccines include, for example, mAb 105AD7 anti-idiotype vaccine, mAb 11D10 anti-idiotype vaccine, mAb 3H1 anti-idiotype vaccine, GM2, GM2-KLH, and MUC-1 antigen among many others.

Cancer therapies include a variety of combination therapies that are contemplated with the fusion proteins of the current invention including immunological, chemical and radiation based treatments. Combination immunotherapies include, for example, interleukin-2, monoclonal and/or bispecific antibodies such as Rituximab, Herceptin (Trastuzumab), mAb Lym-1, mAb m170, mAb BC8, mAb Anti-B1 (tositumomab), Campath-1H, anti-CEA mAb MN-14, mAb HuG1-M195, mAb HuM291, mAb 3F8, mAb C225 (cetuximab), anti-Tac mAb (daclizumab), and mAb hLL2 (epratuzumab).

Combination immunotherapies also include monoclonal antibodies (mAb) linked to toxins or other agents. Examples include mAb gemtuzumab ozogamicin (mylotarg), mAb Mono-dgA-RFB4, mAb ibritumomab tiuxetan (IDEC-Y2B8), and Anti-Tac(Fv)-PE38. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

For precancerous conditions such as benign prostatic hyperplasia, a second therapeutic agent selected from an α-1 adrenergic receptor blocker such as terazosin, doxazosin, prazosin, bunazosin, indoramin, tamsulosin, pracizin or alfuzosin; a 5-α-reductase enzyme blocker such as finasteride or an azasteroid derivative; a combination of an α-1 adrenergic receptor blocker, and a 5-α-reductase enzyme blocker, a potassium channel opener such as minoxidil, and a retinoic acid derivative.

Various combinations may be employed, for instance where the fusion protein of the current invention is "A" and the radio-, chemotherapeutic or other therapeutic agent is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapy including the fusion protein of the current invention may precede or follow the other agent treatment by intervals ranging from minutes to weeks. In embodiments where the other agent and fusion protein are applied separately to the cell, one would generally ensure that a significant period of time did not expire between the time of each delivery, such that the agent and the fusion protein would still be able to exert an advantageously combined effect on the cell. In such instances, it is contemplated that one would contact the cell with both modalities within about 12-24 h of each other and, more preferably, within about 6-12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) elapse between the respective administrations.

O. Pharmaceutical Compositions

Pharmaceutical compositions of the present invention comprise an effective amount of one or more fusion proteins, therapeutic agents or additional agent dissolved or dispersed in a pharmaceutically acceptable carrier. Aqueous compositions of the present invention comprise an effective amount of the fusion protein, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intranasal, intralesional, or even intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The fusion proteins of the present invention can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

In certain embodiments, the use of liposomes and/or nanoparticles is contemplated for the formulation and administration of the fusion proteins and/or analogs thereof. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

The therapeutic agent may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, by inhalation (e.g. aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the fusion proteins are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

P. Kits

Any of the compositions described herein may be comprised in a kit. In a non-limiting example, an immunoglobulin fusion protein, a nucleic acid coding for an immunoglobulin fusion protein and/or additional agent, may be comprised in a kit. The kits will thus comprise, in suitable container means, a fusion protein, a nucleic acid coding for a fusion protein and/or an additional agent of the present invention. The inventors envisage other components that may be included in a kit. These include but are not limited to immunodetection agents such as peroxidase and alkaline phosphatase linked monoclonal and polyclonal antibodies, immunoprecipitation reagents such as protein A- or protein G-linked beads, immune cell purification reagents such as magnetic beads, cloning reagents for the purpose of manipulating an expression vector, protein expression reagents including prokaryotic and eukaryotic cell lines for the purpose of protein expression.

The kits may comprise a suitably aliquoted fusion protein and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the fusion protein, lipid, additional agent, and any other reagent containers in close confinement for commercial sale. Such containers may include injection or blow-molded plastic containers into which the desired vials are retained.

Therapeutic kits of the present invention comprise an immunoglobulin fusion protein, polypeptide, peptide, inhibitor, gene, vector and/or other effectors. Such kits will generally contain, in suitable container means, a pharmaceutically acceptable formulation of an immunoglobulin fusion protein in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The immunoglobulin fusion protein composition may also be formulated into a syringeable composition, in which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the immunoglobulin fusion protein formulation is placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate immunoglobulin fusion protein within the body of an animal. Such an instrument may be a syringe, pipette, forceps, and/or any such medically approved delivery vehicle.

As used herein the specification, "a" or "an" may mean one or more. As used herein in the claim(s), when used in conjunction with the word "comprising", the words "a" or "an" may mean one or more than one. As used herein "another" may mean at least a second or more.

AIG is aggregated IgG; IC is an immune complex; a HCH2 unit comprises the hinge and CH2 domain of an immunoglobulin; FcγR is Fc gamma receptor; SLE is systemic lupus erythematosus; MS is multiple sclerosis; CDCC is complement-dependent cellular cytotoxicity; ADCC is antibody-dependent cell-mediated cytotoxicity; CDC is complement-dependent cytotoxicity; EAE is experimental autoimmune encephalomyelitis; NK cells are natural killer cells; and PBMC are peripheral blood mononuclear cells.

Q. EXAMPLES

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Framework Vector

The framework region of human $IgG_1$ comprised of H-CH2-CH3 was isolated from total RNA from cell line ARH-77 and subcloned using RT-PCR, a primer, FRM-5p-H3, that introduced a HindIII site immediately 5' of the hinge region and a second primer, FRM-3p-Sal, which introduced a SalI site immediately 3' of the stop codon (Table 5). Clone pFRM-HS was characterized by DNA sequencing and used for further expression construct assembly. Primers for this and subsequent steps involving IgG1 cloning were designed using sequence data from the human IgG1 constant region gene as a guide (accession #Z17370).

TABLE 5

Sequence of Primers used for PCR Amplification

| Name | Sequence | Seq ID No. |
|---|---|---|
| FRM-5P-H3 | GgccgctaAAGCTTGAGCCCAAATCTT GTGACAAAACTC | 1 |
| FRM-3P-Sal | GgccgctaGTCGACTCATTTACCCGGAG ACAGGGAGAG | 2 |
| Hinge1 | CccgtaGAATTCGAGCCCAAATCTTCT GACAAAACTCACACATCCCCACCGT CCCCA | 3 |

TABLE 5-continued

Sequence of Primers used for PCR Amplification

| Name | Sequence | Seq ID No. |
|---|---|---|
| CH2NH3 | GgccgcatAAGCTTggagccTCGCGATTT GGCTTTGGAGATGGTTTTCTC | 4 |
| SMA-DELH | GgccgcatCCCGGGGAGCCCAAATCTT CTGACAAAACT | 5 |
| CH2H3 | GgccgcatAAGCTTTTTGGCTTTGGAGA TGGTTTTCTC | 6 |
| CD8-5PXho | GgccgctaCTCGAGATGGCCTTACCAGT GACCGCCTTG | 7 |
| CD8-3P119Eco | GgccgctaGAATTCCGTCGTGGTGGGCT TCGCTGGCAG | 8 |

The small letters indicate bases used as clamps or spacers. Bold face letters denote the location of restriction sites.

Example 2

Hinge Mutagenesis and CH2 Subcloning

The FcγR binding region of Fc, composed of the hinge and CH2 domains (HCH2), was isolated as a separate monomer unit. The hinge region within the HCH2 monomer unit was modified using PCR mutagenesis to change the three cysteines that form inter-chain disulfide bridges between Fc units to serines. The FcγR binding domain was amplified using a 5' primer, Hinge1 (Table 5), which introduced single nucleotide changes in each of the three hinge cysteine codons resulting in their alteration to serine residues. The 5' primer also introduced an EcoRI site immediately 5' of the hinge region. The 3' primer, CH2NH3 (Table 5), directed the amplification of the CH2 domain and introduced an in-frame 3' NruI site separated by a 6 nucleotide spacer from a HindIII site. The PCR product was digested with EcoRI and HindIII and cloned into vector pBSKS+. The construct, composed of 5' EcoRI-HCH2-NruI-HindIII 3', is termed "ENH" to denote the sequence of restriction sites and served as the starting unit for polymer construction. Clone pENH18 was characterized by DNA sequencing and used in subsequent cloning steps.

Two additional constructs, an extension unit designated pSNH, and a capping unit designated pSH3, were generated. These varied from pENH18 only in their flanking restriction sites. pSNH has 5' SmaI-HCH2-NruI-HindIII 3' and was amplified using pENH18 as template and primers that introduced the flanking restriction sites (Table 5). The second construct, pSH3, contains 5' SmaI-HCH2-HindIII 3' and was amplified from pENH18 template using a 5' primer, SMA-DELH, and a 3' primer, CH2H3 (Table 5), which introduced a single HindIII site that flanks the 3' end of the CH2 domain. Both the pSNH and pSH3 plasmids were digested with SmaI and HindIII. The inserts were gel purified and stored for future use.

Example 3

Polymer Construction

Polymers composed of HCH2 units were built using the scheme presented in FIG. 1. The HCH2 polymers were constructed by the sequential addition of a single starting unit (ENH), multiple extension units (SNH), and ended by addition of a single capping unit (SH3). Clone pENH18 was digested with NruI and HindIII resulting in a 5' blunt end and a 3' sticky end. Next a SNH insert, digested as described above, was ligated into the linearized vector resulting in the in-frame insertion of a HCH2 repeat unit at the 3' end of the pENH18 starting unit. The insertion also regenerated the original sequence of restriction sites (NruI-spacer-HindIII) which were used in the next round of extension. The extension process continued with NruI and HindIII digestion followed by ligation with the next SNH insert as described above. This cycle of digestion and insertion was repeated as needed to generate the linear polymers. In the final round of polymer construction a 'capping' unit (SH3 insert) is ligated into the polymer instead of the SNH insert. This resulted in the loss of the internal cloning site. The result was the stepwise insertion of HCH2 units into the framework expression vector. Directionality of HCH2 insertion was maintained by the use of non-compatible flanking restriction sites. The junction between the HCH2 units was composed of the fusion of the 5' NruI half-site to the 3' SmaI half-site, resulting in an in-frame Gly-Ser spacer between the protein domains. The completed polymer constructs were liberated from the pBSKS+ cloning vector at the EcoRI and HindIII sites and cloned into like-digested pFRM-HS resulting in the in-frame joining of the HCH2 polymers to the IgG$_1$ framework region.

Example 4

Cloning of the Extracellular Domain of Human CD8α

The secretion signal and first 119 residues of the extracellular domain of human CD8α were amplified using PFU polymerase (Stratagene), CD8α cDNA, and primers that introduced flanking 5' XhoI and 3' EcoRI sites (Table 5). Primers were designed using sequence data from the human CD8α cDNA as a guide (accession #M12824). The PCR product was digested with XhoI and EcoRI and cloned into like-digested pBlueBac4.5 baculovirus transfer vector (Invitrogen). The resulting construct, pCD8Bac, was used as host for subsequent cloning steps.

Figure 2:
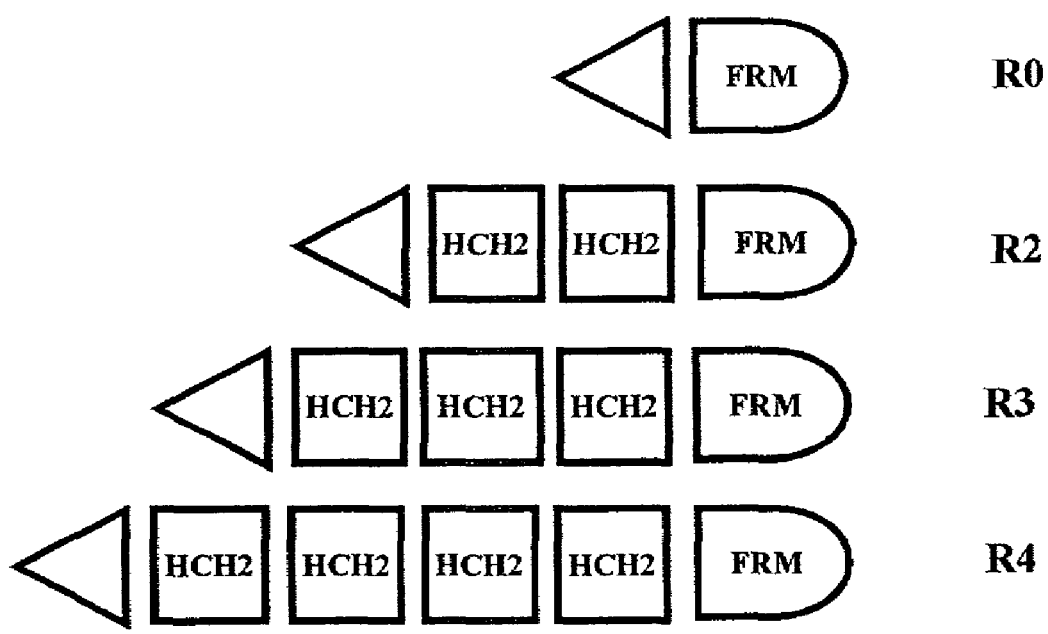
FIG. 2—Schematic representing fusion protein constructs. The triangle represents the leader sequence and amino-terminal domain which is comprised of either the first 119 amino acid residues from the extracellular domain of human CD8α or domain I of HSA. The boxes, labeled HCH2, represent repeat units comprised of the hinge and CH2 domains of human IgG1(amino acid residues 226-350). The element labeled FRM represents the framework region comprised of the hinge, CH2 and CH3 domains of human IgG1 (amino acid residues 226-457). RO, indicates framework without repeat units, R2, framework with 2 repeat units, R3, framework with 3 repeat units, R4, framework with 4 repeat units.

The polymer-framework constructs were liberated from the pBSKS+ cloning vector by digestion with EcoRI and SalI and united with the CD8α sequences by their ligation into like-digested pCD8Bac. The CD8-HCH2 polymer constructs were liberated from pCD8Bac at the BamHI and SalI sites, gel purified and ligated into the same sites in the pIE1-4 insect cell expression vector (Novagen). The pIE1-4 vector had been modified previously to accommodate the restriction sites that flank the inserts. The resulting expression constructs have the CD8α secretion signal and extracellular domain on their 5' termini fused to the HCH-2 polymer units in the middle and the framework domains on their 3' termini (FIG. 2).

Example 5

Establishment of Stable Expressing Polyclonal Cell Lines

Plasmid DNA destined for transfection was purified using Qaigen plasmid DNA isolation columns (Qaigen). The pelleted DNA was washed repeatedly with 70% ethanol, air dried and resuspended in sterile TE buffer. Sf9 insect cells (ATCC) were propagated in ExCell 420 medium (JRH Biosciences) containing 100 u/mL penicillin and 100 μg/mL streptomycin (Gibco). One day prior to transfection, 2×10$^6$ cells were plated onto 60 mm culture dishes in ExCell 420 medium supplemented with 10% Sf9 conditioned medium.

Sf9 cells were washed once and the medium replaced with 2 mL antibiotic-free ExCell 420. Transfection was mediated by the cationic lipid Cellfectin (Gibco). 5 μg of expression construct along with 1 μg of pIE-Neo or 6 μg of pBSKS as a negative control were added to 290 μL of antibiotic-free ExCell 420. In a separate tube 280 μL of antibiotic-free medium was mixed with 20 μL of Cellfectin reagent. The contents of the tubes were combined and the DNA-lipid complexes were allowed to form over a period of 30 min after which time they were added drop-wise to each 60 mm culture dish. Cells were incubated for 8 hours after which time 2 mL of medium was added. Incubation with the DNA-lipid complexes continued overnight. On the day after transfection the medium was removed and replaced with antibiotic containing medium supplemented with 10% Sf9 conditioned medium. On the second day post-transfection the cells were split into T25 flasks with selection medium composed of ExCell 420 supplemented with 10% conditioned Sf9 medium, 400 μg/mL of geneticin (G418)(Gibco), and antibiotics. Flasks were monitored for cell death; the pBSKS control cells died within 10 days. pIE-Neo containing transfectants showed robust growth. The cultures were expanded into T75 flasks and used as seed stocks for protein expression.

Example 6

Protein Expression and Purification

To express larger amounts of protein, 250 mL cultures were initiated in spinner and/or shaker flasks. Cultures were grown in ExCell 420 with 100 μg/mL G418 , 0.1% pluronic F-68, and antibiotics. Culture supernatants were centrifuged to remove cellular debris. PMSF (Sigma) and Pepstatin A (Sigma) were added to a final concentration of 1 mM and 1 μM respectively.

Conditioned medium was clarified by passage through a 0.45 μm filter and applied to 1 mL protein G-sepharose (Pharmacia) columns at a rate of 1 mL/min. Columns were washed with 100 mL PBS, pH 7.0 and proteins eluted with 3 mL of elution buffer (20 mM glycine, 150 mM NaCl, pH 3.0). Eluate was immediately brought to neutral pH by the addition of 100 μL of 1 M Tris, pH 9.0. Recombinant proteins were equilibrated in RPMI medium and concentrated using centrifugal concentrators with a MW cutoff of 30 kD (Amicon/Millipore). Protein concentrations were determined using the Bradford method (Biorad) with human IgG as the standard.

Example 7

Expression of HCH2 Polymers Fused to an Amino Terminal Human CD8α Domain

To demonstrate the utility of the vectors, the extracellular domain of human CD8α was expressed as a HCH2 polymer fusion protein. The secretion signal and first 119 residues of human CD8α were cloned into the amino termini of the HCH2 polymers. The expression constructs were inserted into the pIE1-4 vector (Novagen), which places the fusion constructs under the control of the baculovirus ie1 gene promoter which is constitutively active in Sf9 cells (Jarvis, et al., 1996). The use of transfected insect cells can result in improved expression of glycosylated secretory proteins due to more efficient processing and secretion than is achieved in virus infected cells (McCarroll, et al., 1997; Pfeifer, et al., 1998).

Four constructs were chosen for expression analysis, termed CD8R0 through CD8R4, which contain between 0 and 4 HCH2 units in the polymer in addition to the HCH2 unit within the framework (Table 6 and FIG. 2). As result of the covalent dimerization of the framework domains, the mature proteins contain between 2 and 10 HCH2 units in the CD8R0 through CD8R4 proteins respectively (Table 6). The fusion proteins were secreted in useful amounts from polyclonal cell lines established in Sf9 cells following transfection and selection with G418. The recombinant proteins were isolated in a single step from conditioned culture medium by passage over a protein G-sepharose column. The expressed polymers are stable, secreted, soluble and are readily concentrated to useful levels. The proteins are glycosylated, as documented by the difference in predicted and observed molecular weights. Yields correlate inversely with protein size and fall in the range of 0.8 to 2.0 µg/mL of conditioned medium.

Figure 3:
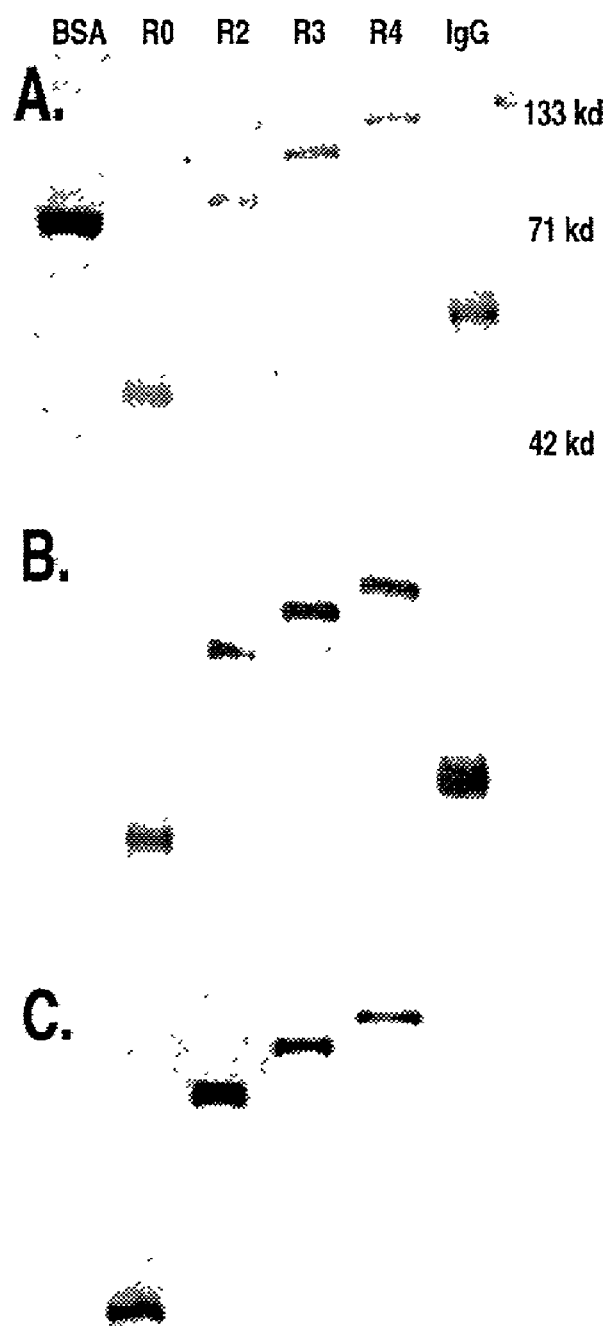
FIGS. 3A, and 3B, and 3C.—Western Blot analyses.

Results: As shown in FIG. 3A the HCH2 polymers are expressed, stable, and secreted. The observed molecular weight is larger than predicted for the peptide backbone alone (FIG. 2), which indicates that the proteins are glycosylated (see also Table 6). A Western blot probed with antibodies directed against human Fc reveals binding to the HCH2 polymers in a fashion similar to the IgG control (FIG. 3B). A similar blot probed with antibodies directed against human CD8α shows binding only to recombinant protein (FIG. 3C). Taken together, these results demonstrate that the HCH2 polymers contain both the CD8α and Fc antigenic determinants, indicating that the proteins are correctly expressed and secreted. Correlation of the amount of purified protein to original volume of conditioned medium gives yields that range from 2 µg/mL (CD8R0) to 0.8 µg/mL (CD8R4) of

TABLE 6

Number of HCH2 units, potential N-linked glycosylation sites, predicted molecular weights, and contribution of N-linked glycosylation to apparent molecular weight of CD8-HCH2 polymers fused to the IgG1 - Fc framework.

| Construct | Number of HCH2 units inserted | Number of HCH2 units in single chain | Number of HCH2 units in mature polypeptide | N-Linked glycosylation sites | Predicted MW (KD) | Apparent MW (KD) Control | Apparent MW (KD) PNGase + |
|---|---|---|---|---|---|---|---|
| CD8R0 | 0 | 1 | 2 | 2 | 39.5 | 44.2 | 43.3 |
| CD8R2 | 2 | 3 | 6 | 4 | 67.8 | 85.7 | 82.1 |
| CD8R3 | 3 | 4 | 8 | 5 | 82.0 | 104.8 | 97.5 |
| CD8R4 | 4 | 5 | 10 | 6 | 96.2 | 125.7 | 116.9 |

Example 8

Structural Integrity

To examine the structural integrity and antigenic content, the recombinant proteins were resolved on SDS-PAGE gels and analyzed by Western blot. Proteins were electrophoresed on 7% SDS-PAGE gels (Laemmli et al., 1970) and transferred to nitrocellulose membranes (MSI). Membranes were blocked overnight in 5% non-fat milk in Tris-buffered saline, pH 7.4 (TBS). For analysis of Fc domains, a total of 50 ng of recombinant protein or 0.5 µg of control proteins (human IgG and BSA) were loaded onto the gels. The membrane was incubated for two hours with horse radish peroxidase (HRP)-labeled goat anti-human Fc polyclonal antibody (Caltag) used at 1:10000 dilution in a binding buffer consisting of 0.1% non-fat milk and 0.1% normal goat serum in TBS. The blot was washed with TBS-tween and detection performed using the ECL-plus chemoluminescent reagent following manufacturers instructions (Amersham).

For CD8α Western blot analysis, recombinant proteins were loaded onto gels at 200 ng and controls were loaded at 0.5 ug per well. The membrane was incubated for two hours with mouse anti-human-CD8α monoclonal antibody (clone HIT8a, Pharmingen) used at 1:800 dilution in a binding buffer consisting of 0.2% non-fat milk and 0.1% normal human serum in TBS. Blots were washed as above and incubated with HRP conjugated rabbit anti-mouse IgG (DAKO) used at 1:1000 dilution in a binding buffer consisting of 0.1% non-fat milk, 0.1% normal human serum, 0.1% normal goat serum, and 0.03% Tween in Tris-buffered saline. Blots were washed and detected as above. For direct visualization of proteins, gels were stained with Coomassie brilliant blue.

culture medium. Yields correlated negatively with protein size and/or the number of HCH2 repeat units. No evidence for accumulation of misfolded or aggregated recombinant proteins was found in the Sf9 cell pellets implying some other basis for the bias against larger proteins.

Example 9

Dimerization of HCH2 Polypeptides Using Disulfide Linkages

One anticipated difficulty was the potential for mutated HCH2 units to compete with native hinge regions during oligomerization. This could potentially result in a significant amount of monomer production. The proteins were analyzed on SDS-PAGE gels under reducing and non-reducing conditions to determine if the HCH2 polymers form antibody-like covalent oligomers. In all cases the recombinant proteins formed dimers that could be reduced by 2-mercaptoethanol indicating that IgG-like oligomerization had occurred. However, both CD8R0 and CD8R4 produced detectable levels of monomers. Whether this resulted from post-secretion disulfide-bond reduction or a failure to oligomerize remains unresolved. The presence of monomers in the CD8R0 preparations argues against a competitive mechanism however.

Example 10

Cloning and Expression of Human Serum Albumin (HSA) Domain I Fused to HCH2 Polymers.

Previously, HCH2 polymers had been expressed as fusions with the extracellular domain of human CD8α. In order to discern which effects are attributable to the HCH2 polymers and which to the amino-terminal fusion partner, fusion proteins were constructed with the domain I of HSA fused to the HCH2 polymers. The biological activities of the CD8α-HCH2 polymers could then be compared to those of the HSA-HCH2 polymers. These experiment also serve to demonstrate the general utility of the expression system. The secretion signal and first 197 residues of domain I of HSA were amplified using RT-PCR, total RNA derived from cell line HEP G2 (ATCC HB-8065), and primers that introduced flanking 5' XhoI and 3' EcoRI sites. Primers were designed using sequence data from the HSA cDNA as a guide (accession #V00494). The PCR product was digested with XhoI and EcoRI and cloned into like-digested pFRM-HCH2 vectors. The pFRM-HCH2 vectors direct expression of N-terminal protein domains fused in-frame to HCH2 polymers with varying numbers of HCH2 repeats. The vector backbone is derived from the pIE1-4 insect cell expression vector (Novagen) which places fusion protein constructs under the control of the baculovirus ie1 gene promoter.

The HSA-HCH2 fusion constructs were stably transfected into SF9 cells as was done previously for the CD8α-HCH2 constructs. Similarly, four constructs were chosen for expression analysis, termed HSAR0 through HSAR4, which contain between 0 and 4 HCH2 units in addition to the HCH2 unit within the framework (FIG. 2). As a result of the covalent dimerization of the framework domains, the mature proteins contain between 2 and 10 HCH2 units in the HSAR0 through HSAR4 proteins respectively. Recombinant protein was isolated from conditioned medium as described in Example 6 above. The proteins were resolved on 7% SDS-Page gels and stained to reveal protein.

Results: HSA-HCH2 fusion proteins are expressed, secreted, and stable. The proteins can be isolated from conditioned medium and concentrated to useful levels. Yields are comparable to those observed for CD8α constructs. These results demonstrate the general utility of the HCH2 expression vectors with two different fusion partners. Also the results demonstrate the stability of the expressed HCH2 fusion proteins with different fusion partners. Experiments described below evaluate and compare the relative biological activities of the recombinant proteins.

Example 11

PBMC Purification, Proliferative Assays, and Cytokine Analysis

Peripheral blood mononuclear cells (PBMC) of six healthy donors were isolated from heparinized blood on a Ficoll-Paque gradient (Pharmacia Biotech Inc) and suspended in AIM V defined serum free medium (Gibco BRL). Recombinant protein stocks were initially prepared in RPMI 1640 (concentration $\geq 1$ mg/ml). Recombinant protein stocks were diluted in AIM V medium (Fisher Scientific) to achieve the desired final concentrations as indicated in the drawings. To prepare IgG aggregates, 4 mg of human IgG (Organen Teknika Corp.) was dissolved in 2 ml of saline and incubated at 57° C. for one hour. The heat aggregated IgG (AIG) obtained was diluted in AIM V medium to the desired final concentration as indicated in the drawings. rIL-2 (Pharmingen) was added at a final concentration of 1 ng/ml. To stimulate PBMC with the anti-CD16 mAb 3G8 (Caltag Laboratories), 50 μl of mAb 3G8 (10 μg/ml or dilutions thereof) in bicarbonate buffer (pH 8.4) was overlaid in each well of a 96 well flat bottom tissue culture plate (Corning Costar) for three hours at RT. The wells were then thoroughly washed with saline, aspirated, and used immediately thereafter for cell culture. PBMC were plated at a final concentration of $2 \times 10^6$ cells/ml in 96 well flat bottom plates (0.200 ml/well final volume) or 48 well flat bottom plates (1 ml/well final volume). For cytokine induction, cells were incubated for 48 hours in a humidified incubator at 37° C. in 5% atmospheric $CO_2$ and the supernatant harvested and centrifuged at 2100 rpm for 10 minutes to pellet cells and cell debris. The cell free supernatant was frozen at −80° C. until assayed for cytokine content. For proliferative assays, cells were incubated for 72 hours in a humidified incubator at 37° C. in 5% atmospheric $CO_2$. During the last 5 hours of culture, wells were pulsed with 1 μCi of [methyl-$^3$H] thymidine (Amersham Corp). Cells were harvested using a PhD cell harvester (Cambridge Technologies). Radioactivity was determined using a Beckman Scintillation Counter LS 5000TD (Beckman Instruments).

Example 12

IFN-γ and TNF-α ELISA

To detect IFN-γ and TNF-α a sandwich ELISA was used. To detect IFN-γ, the mouse anti-human antibody clone NIB42 was used as the capture antibody and the antibody clone 4S.B3 was used as the detecting antibody (both from Pharmingen Corporation). To detect TNF-α, the mouse anti-human antibody clone MAb1 was used as the capture antibody and the antibody clone MAb11 was used as the detecting antibody (both from Pharmingen Corporation). ELISA plates (Costar Corporation, Cambridge, Mass.) were coated with 0.1 ml/well of capture antibody at 0.75 μg/ml in carbonate buffer (0.5 M, pH 8.5). Plates were incubated overnight at room temperature (RT). 0.100 ml of 2% crystallized BSA in Dulbecco's phosphate buffered saline (DPBS) was added to each well for an additional 3 to 6 hours at room temperature. Plates were washed extensively with DPBS and recombinant IFN-γ or TNF-α (used as standards, Pharmingen Corp.) or cell supernatants were added. Recombinant IFN-γ or TNF-α was serially diluted 1:3 from 10 ng/ml to 0.15 ng/ml. Cell supernatants were assayed at 50% and 10% dilutions. Plates were incubated overnight at 4° C., wells were washed, and overlaid with 0.200 ml of biotinlyated detecting antibody at 0.75 μg/ml in 0.2% BSA in DPBS for 2 hours at room temperature. Wells were washed and overlaid with 0.200 ml of goat polyclonal affinity purified IgG reactive to biotin (1:400 in 1% DPBS, Zymed Laboratories, South San Francisco, Calif.) for 1 hour at RT. Wells were washed and 0.200 ml of ortho-phenylenediamine (4 mg/ml) in citrate buffer (0.1 M, pH 4.5) was added to each well. Plates were read on a Thermomax Microplate reader (Molecular Devices Corp., Menlo Park, Calif.).

Example 13

Assessment of HCH2 Polymer—FcγRIII Interactions

To assess potential HCH2 polymer—FcγRIII interactions, HCH2-polymers were assayed for their ability to activate NK cells within PBMC isolates. NK cells express both the low affinity IL-2 receptor, and FcγRIII (CD16) (Nagler et al., 1990). When primed with high levels of IL-2 (1 ng/mL), NK cells mount a proliferative response to CD16 ligation. This triggered response was used as a test of the fitness of IC, AIG and recombinant molecules to engage FcγR. Two different sets of HCH2 polymer constructs were tested for their ability to activate PBMC, one expressing the extracellular domain of CD8α (referred to as CD8R0, CD8R2, CD8R3, and CD8R4) and the other expressing the domain one of HSA (referred to as HSAR0, HSAR2, HSAR3, and HSAR4).

RESULTS: Immobilized anti-CD16 mAb 3G8, in the presence of IL-2, triggers NK cell proliferation and cytokine release through activation of the FcγIII receptor. PBMC isolates were incubated with medium alone, IL-2 (1 ng/ml) alone, immobilized anti-CD16 mAb alone, or with IL2 plus anti-CD16 mAb, and proliferative responses measured 3 days later. Neither IL-2 nor anti-CD16 mAb alone induce significant proliferative responses from PBMC. Proliferative responses in the presence of medium alone were 787±447, in the presence of IL-2 alone were 1957±1117, and in the presence of immobilized anti-CD16 mAb alone were 592±102. However there was a marked increase in proliferative response in the presence of both IL-2 and anti-CD16 mAb. Proliferative responses in the presence of both IL-2 and immobilized anti-CD16 mAb were 15499±2962. Data represent the average from four individuals±SEM.

Figure 4:
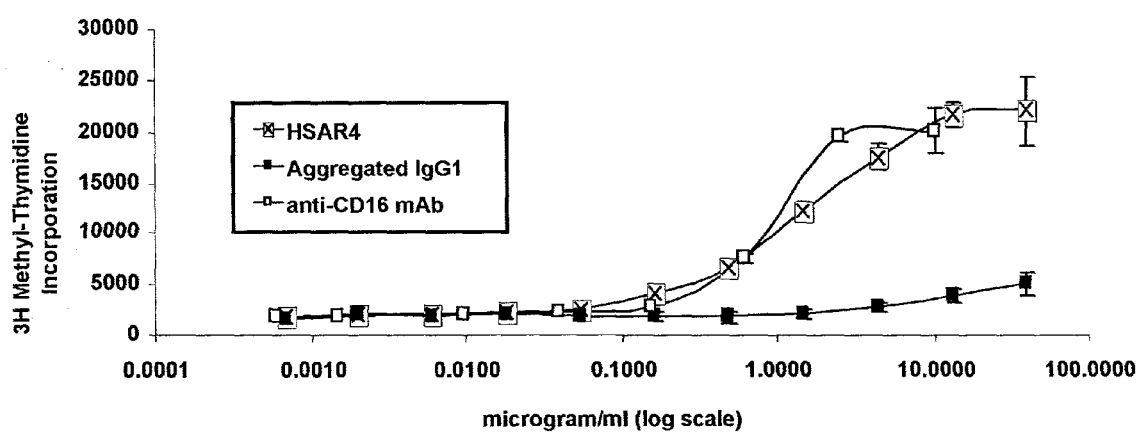
FIG. 4—HSAR4, immobilized anti-CD16 mAb 3G8, and aggregated IgG induce proliferative responses from PBMC in a dose-dependent and IL2-dependent manner. $2\times10^5$ freshly isolated PBMC were plated into 96 well plates in the presence of IL-2 (1 ng/mL) and immobilized anti-CD16 mAb 3G8 together, IL-2 (1 ng/mL) and HSAR4 together, or IL-2 (1 ng/mL) and AIG together for 72 hr. During the last 5 hr the cells were pulsed with 1 µCi of [methyl-$^3$H] thymidine. The graph compares the proliferative response of PBMC to varying dilutions of each reagent. CPM is shown on the y-axis and micrograms/ml of stimulus used is shown on the x-axis. Proliferative responses in the presence of medium alone were 787±447 and in the presence of IL-2 alone were 1957±1117. Data represent the average from four individuals±SEM.

Similarly, HCH2 polymer constructs, expressing the extracellular domain of CD8α were also tested for their ability to induce proliferative responses in PBMC. As shown in Table 7, the CD8α expressing constructs, CD8R0, CD8R2, CD8R3, and CD8R4, all induce proliferative responses in PBMC in the presence of IL-2. Thus, the ability to induce PBMC proliferation correlates with the number of HCH2 units indicating that the constructs mimic AIG function. As CD8R4 was the most effective construct in the assay, as documented in Table 7, it was compared to AIG directly. CD8R4 was as effective at 5 μg/mL as AIG at 125 μg/mL and proliferation was of the same magnitude as that observed using anti-CD16 mAb. Proliferative responses in the presence of 5 μg/mL of CD8R4 and IL-2 were 21694±4636 (18 fold induction over IL-2 alone) and in the presence of 125 μg/mL of AIG and IL-2 were 17388±1342 (16 fold induction over IL-2). HCH2 polymers containing the first domain of HSA were also tested for their ability to induce proliferative responses in PBMC. As shown in FIG. 4., the HCH2 polymer protein HSAR4 was as effective in activating PBMC to proliferate as was immobilized anti-CD16 Ab 3G8 and many times more effective than aggregated IgG.

TABLE 7

Proliferative responses from costimulation of PBMC with recombinant HCH2 polymers and IL-2

| Construct | Induction (CPM)* |
|---|---|
| IL-2 Alone | 2011 ± 714 |
| CD8R0 | 13036 ± 3339 |
| CD8R2 | 17696 ± 3876 |
| CD8R3 | 19293 ± 3412 |
| CD8R4 | 21010 ± 3425 |
| Significance | R0 vs R2 < 0.019 |
| (Student's paired t test) | R0 vs R3 < 0.025 |
|  | R0 vs R4 < 0.0097 |
|  | R2 vs R3 < 0.18 |
|  | R2 vs R4 < 0.036 |
|  | R3 vs R4 < 0.15 |

*Mean ± SEM

Example 14

PBMC Activation by HCH2 Polymer Proteins with Varying HCH2 Repeat Units

Figure 5:
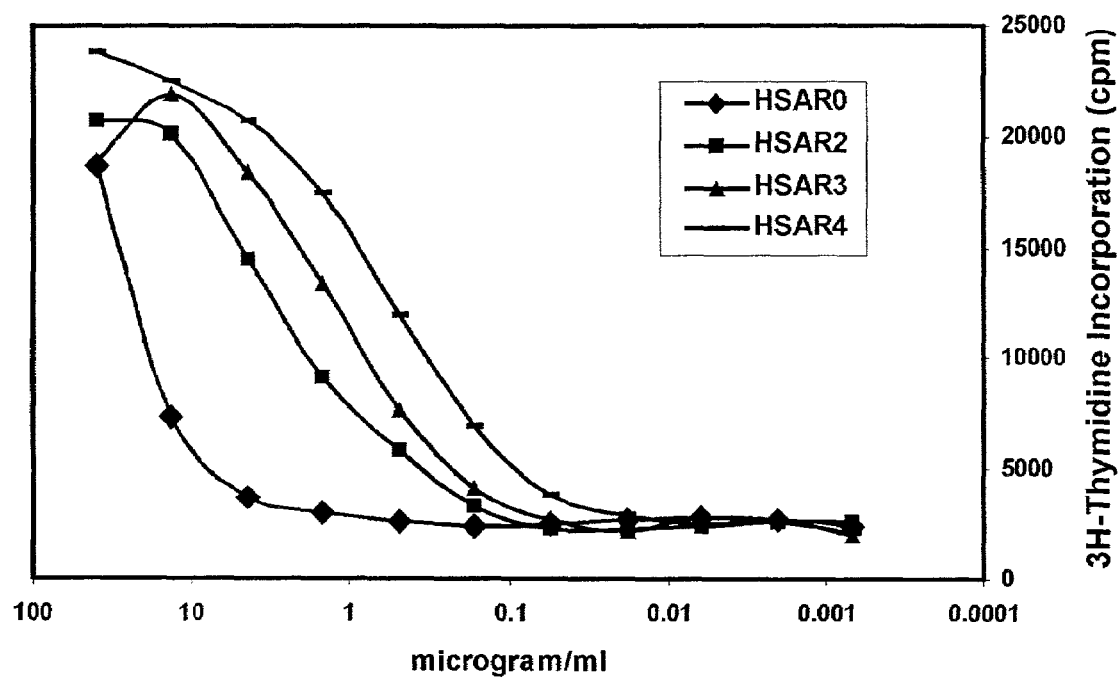
FIG. 5—PBMC activation with HCH2 polymer proteins correlates with the number of HCH2 region repeats indicating a high level of sensitivity of Fcγ receptors to HCH2 number in the HCH2 polymer proteins. $2\times10^5$ freshly isolated PBMC were plated into 96 well plates in the presence of medium alone, or with IL-2 (1 ng/nL) and varying concentrations of HSAR0, HSAR2, HSAR3, or HSAR4 for 72 hr. During the last 5 hr the cells were pulsed with 1 µCi of [methyl-$^3$H] thymidine. The graph compares the proliferative response of PBMC to varying dilutions of each HCH2 polymer protein used. CPM is shown on the y-axis and micrograms/ml of HCH2 polymer protein used is shown on the x-axis. Proliferative responses in the presence of medium alone were 803±1069 and in the presence of IL-2 alone were 2903±962. Proliferative responses in the presence of HSAR0, HSAR2, HSAR3, and HSAR4 in the absence of IL-2 were 1027±176, 1531±504, 1237±379, and 1661±592 respectively. Data represent the average from four individuals±SEM.

PBMC activation by HCH2 polymer proteins correlates with the number of HCH2 region repeats indicating a high level of sensitivity by Fcγ receptors to HCH2 number in the HCH2 polymer proteins (FIG. 5). PBMC were exposed to varying concentrations of different HCH2 polymer proteins containing varying numbers of HCH2 domains in the presence of IL-2 (FIG. 5). RESULTS: A dose dependent response is observed for each HCH2 polymer protein. PBMC respond better to HCH2 polymer proteins containing greater numbers of repeating HCH2 units. Thus, HCH2 polymer proteins can be utilized to discern subtle differences in receptor reactivity to Ig. As indicated in the legend of FIG. 5., proliferative responses to the HCH2 polymer proteins in the absence of IL-2 approximated those found in medium alone. Thus, the ability of the HCH2 polymer proteins to activate PBMC to proliferate is dependent upon co-stimulation with IL-2 as observed with immobilized anti-CD16 Ab. Data shown represent the means obtained using PBMC from four different donors.

Example 15

HCH2 Polymer Proteins that Express Different Protein Domains Activate PBMC in a Similar Manner To directly compare the biological function of HCH2 polymer proteins constructed with repeating HCH2 units along with domains from different proteins, the ability of HCH2 polymer proteins expressing domain one of HSA (HSAR0 and HSAR4) to activate PBMC was compared to that of HCH2 polymer proteins expressing the extracellular domain of CD8 alpha (CD8R0 and CD8R4) Table 8. HSAR0, HSAR4, CD8R0, and CD8R4 were used at a concentration of 5 μg/ml along with IL-2 (1 ng/ml) to activate PBMC as described in Example 8. RESULTS: As shown in Table 8, HSAR0, HSAR4, CD8R0, and CD8R4 all activate PBMC to proliferate in the presence of IL-2. An increase in the proliferative response is noted with constructs containing higher numbers of HCH2 repeat units irrespective of the coexpressed protein domain. Thus HCH2 polymer proteins may be constructed with varying numbers of HCH2 repeat units that coexpress domains from different types of proteins and still retain the biological activating properties of the HCH2 repeat units.

TABLE 8

Proliferative responses from costimulation of PBMC with recombinant HCH2 polymers and IL-2

| Culture Condition | cpm ± SEM |
|---|---|
| Medium | 653 ± 179 |
| IL-2 | 7132 ± 2423 |
| HSAR0 + IL-2 | 5219 ± 1125 |
| HSAR4 + IL-2 | 21837 ± 4868 |
| CD8R0 + IL-2 | 15991 ± 3320 |
| CD8R4 + IL-2 | 25684 ± 4636 |

Example 16

Cytokine Secretion Following Stimulation with HCH2 Polymer Proteins

HCH2 polymer proteins activate PBMC to secrete cytokines in a manner similar to the natural IgG$_1$ ligand and anti-CD16 mAb (Table 9). PBMC were activated with IL-2 alone or IL-2 plus immobilized anti-CD16 antibody 3G8 (10 μg/ml), aggregated IgG (40 μg/ml), or HSAR4 (40 μg/ml)

(Table 9). Both IFNγ and TNFα production by PBMC increase in the presence of anti-CD16 Ab, AIG, and HSAR4 compared to IL-2 alone.

TABLE 9

Cytokine secretion from PBMC stimulated with IL-2 alone, or with immobilized anti-CD16 mAb, aggregated IgG, or HSAR4

|  | TNF-α ± SEM (ng/ml) | IFN-γ ± SEM (ng/ml) |
|---|---|---|
| Medium | 0.01 ± .01 | 0 ± 0 |
| IL-2 | 0.80 ± 0.4 | 2.7 ± 2.1 |
| Immobilized anti-CD16 mAb + IL-2 | 3.32 ± 1.49 | 9.85 ± 3.38 |
| Aggregated IgG + IL-2 | 2.46 ± 0.76 | 13.01 ± 4.30 |
| HSAR4 + IL-2 | 4.94 ± 1.03 | 33.58 ± 2.53 |

HCH2 polymer proteins induce IFNγ and TNFα secretion from PBMC in a dose dependent manner (Table 10).

TABLE 10

Cytokine secretion following stimulation with HCH2 polymer proteins.

| | HSAR0 (μg/ml) + IL-2 | | | HSAR4 (μg/ml) + IL-2 | | | IL-2 | |
|---|---|---|---|---|---|---|---|---|
| | 10 | 5 | 1 | 10 | 5 | 1 | alone | medium |
| IFN-γ | 1.6 | .9 | .3 | 2.6 | 2.4 | 1.7 | .18 | .15 |
| THF-α | .34 | .17 | .2 | 1.9 | 1.5 | 1.2 | .2 | .18 |

PBMC were exposed to varying concentrations of two HCH2 polymer constructs, one, HSAR0, has no inserted HCH2 domains though as a result of the dimerization of the Fc framework region there are two HCH2 domains in the mature polypeptide, the other, HSAR4, has a total of ten HCH2 domains in the mature polypeptide (see Table 6). Both IFNγ and TNFα secretion were induced in PBMC stimulated with both constructs. At these high concentrations it is likely that some of the HSAR0 construct becomes immobilized on the well surface and effectively stimulate FcγRIIIa. At lower concentrations of protein, only HCH2 polymer HSAR4 induces cytokine secretion showing the effect of the additional HCH2 domains on receptor activation.

Example 17

Figure 6:
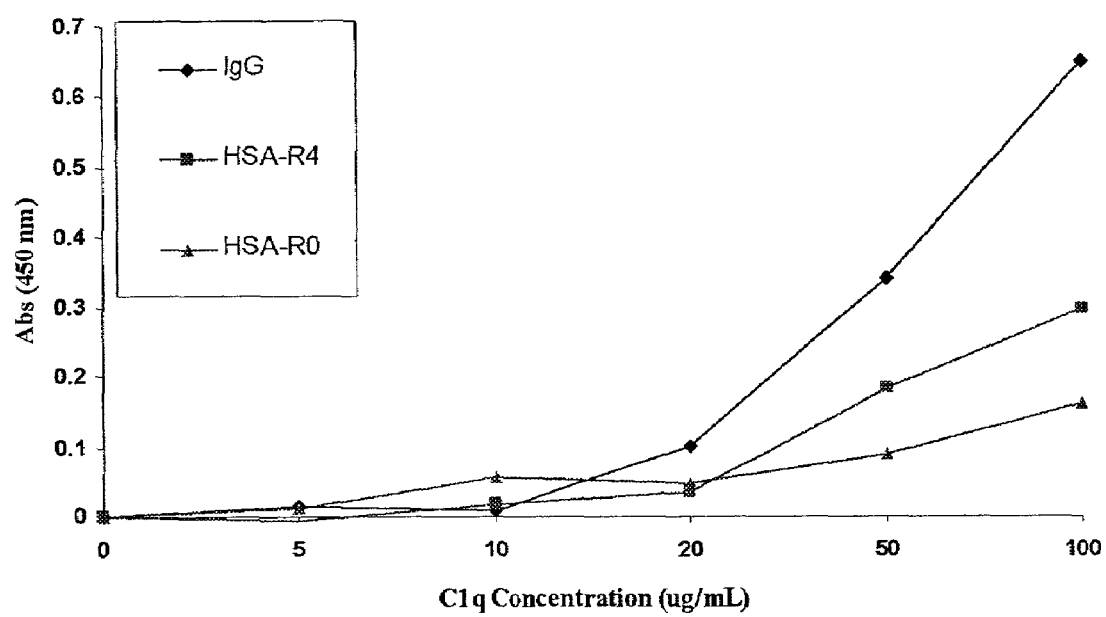
FIG. 6—C1q binding assay. Human IgG, HSAR0, or HSAR4 were allowed to bind overnight to 96-well plates at a concentration of 1 µg/mL. The next day the plates were washed and the immobilized proteins were incubated with human C1q at the indicated concentrations for 4 hours in PTG buffer. Bound C1q was detected with goat anti-human C1q polyclonal antibodies. The results demonstrate that HCH2 polymers expressed in insect cells engage C1q weakly.

HCH2 Polymers Can Be Expressed to Minimize Interaction with Complement Factor C1q For certain therapeutic applications, the binding of complement to the HCH2 polymers could pose an unwanted and potentially deleterious side effect. In addition, complement binding to the HCH2 polymers could confound results in certain studies. Insect cells are known to express proteins that have altered carbohydrate moieties. These alterations may weaken binding of complement factor C1q to these proteins. For this reason the binding of C1q to HCH2 polymers expressed in insect cell line SF9 was investigated. An assay examining the binding of C1q to human IgG or to HCH2 polymers expressed in insect cells was undertaken. Various concentrations of human C1q were allowed to bind to either human IgG or to the HCH2 polymers HSAR0 and HSAR4 previously immobilized onto wells of a 96 well ELISA plate. The extent of C1q binding was detected using a goat anti-human C1q polyclonal antibody. The results, shown graphically in FIG. 6, demonstrate that HCH2 polymers isolated from an insect cell expression system engage C1q more weakly than native IgG.

Example 18

EAE Induction

EAE was induced in SJL/J mice, six to seven weeks old. Each mouse received a total of 0.1 ml of adjuvant distributed over three sites on the back. Injections were delivered intradermally into shaved regions of the skin above the flanks and between the shoulder blades. To prepare adjuvant for immunization, myelin proteolipid protein peptide 139-151 (Peptides International, Louisville, Ky.) was dissolved in PBS at 1.5 μg/ml and emulsified with an equal volume of Complete Freund's adjuvant (Difco Laboratories, Detroit, Mich.). 200 ng of pertussis toxin (List Biological Labs Inc., Campbell, Calif.) in 0.1 ml of saline was injected into the tail vein of each mouse 1 day and 3 days after immunization. To determine the effect of the constructs on disease severity, mice were injected intraperitoneally with saline alone (150 μl total volume) or with saline containing HSAR0 (50 μg HSAR0/150 μl of saline) or with saline containing HSAR4 (50 μg HSAR4/150 μl of saline). Mice were injected with the constructs or saline control, 3 days before immunization, 1 day after immunization and 3 days after immunization. Clinical disease was graded on a scale of 0 to 5 of increasing severity; 0, no abnormality; 1, a flaccid tail; 2, a flaccid tail with mild hind limb weakness; 2.5, moderate hind leg weakness but not complete paralysis; 3, total paralysis of hind legs, 4, hind leg paralysis with forelimb weakness or paralysis; 5, moribund. Mice that became moribund were euthanized.

Figure 7:
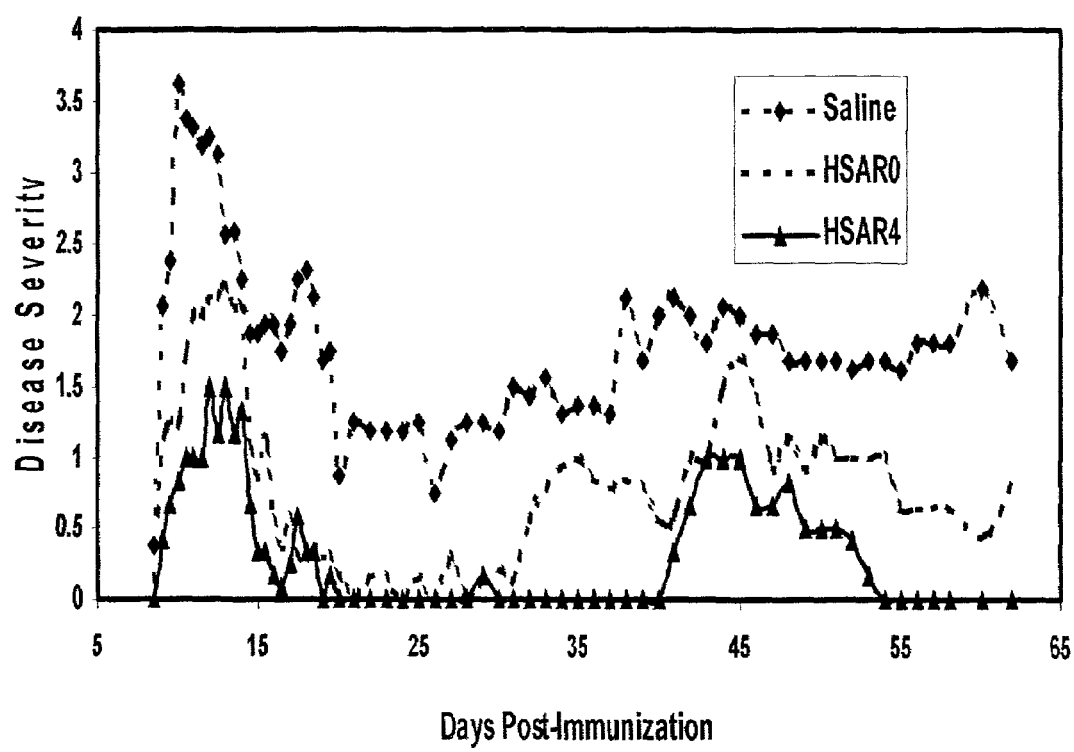
FIG. 7—EAE was induced in SJL/J mice with PLP peptide in complete Freund's adjuvant. Mice were treated with HSAR4 (50 µg/0.150 ml saline, given i.p.), HSAR0 (50 µg/0.150 ml saline, given i.p.) or saline alone three days prior to, 1 day after, and 3 days after, immunization with PLP peptide. Clinical disease was graded on a scale of 0 to 5 of increasing severity; 0, no abnormality; 1, flaccid tail; 2, flaccid tail with mild hind limb weakness; 2.5, moderate hind leg weakness but not complete paralysis; 3, total paralysis of hind legs, 4, hind leg paralysis with forelimb weakness or paralysis; 5, moribund. Mice that became moribund were sacrificed.

EAE in the SJL/J mouse strain is characterized by an early acute disease from which the mice recover partially or fully. The disease then relapses and becomes a chronic relapsing illness from which the mice seldom recover. RESULTS: As shown in FIG. 7, mice injected with HSAR4 displayed a less severe acute disease compared to mice injected with saline alone or with HSAR0. Mice injected with HSAR0 had an acute disease of intermediate severity compared to mice injected with HSAR4 or saline alone. All mice injected with HSAR4 or HSAR0 recovered from the acute illness while the majority of those treated with saline alone never recovered fully from the acute phase of the disease. Mice injected with HSAR4 displayed fewer relapses than mice treated with HSAR0 or saline alone. Data shown are the average clinical disease scores. N=8 mice for saline, n=8 for HSAR0 and n=6 for HSAR4. One mouse treated with HSAR0 became moribund on day 14 and was euthanized. A score of 5 was entered into the data for day 14 and thereafter entries were not made for this animal.

Mice treated with HSAR4 had significantly less severe disease during the acute phase and during the relapsing phase of the disease than did saline controls and this persisted for longer periods of time and to a greater extent than that observed for HSAR0 treated animals (p<0.05 vs. saline for each day of observation from the onset of disease on day 8 to day 13, and from days 15 to day 41, non-inclusive of day 26; unpaired student's t test). HSAR0 treated mice had significantly less severe disease compared to saline treated controls during both the acute phase of disease and during relapses (p<0.05 vs. saline for each day of observation from days 9 to 12, and from 16 to 19.5; unpaired student's t test). Significantly less disease activity was also observed at later time points in both the HSAR0 and HSAR4 treated groups compared to saline controls.

REFERENCES

The following references, to the extent that they provide exemplary procedural or other details supplementary to those set forth herein, are specifically incorporated herein by reference.

Achiron et al., Intravenous immunoglobulin treatment in multiple sclerosis. Effect on relapses. *Neurology* 50, 398-402, 1998.

Alcover et al., A soluble form of the human CD8 alpha chain expressed in the baculovirus system: biochemical characterization and binding to MHC class I. *Mol. Immunol.* 30, 55-67, 1993.

Anegon et al., Interaction of Fc receptor (CD16) ligands induces transcription of interleukin 2 receptor (CD25) and lymphokine genes and expression of their products in human natural killer cells. *J. Exp. Med* 167, 452-72, 1998.

Antel et al., Generation of suppressor cells by aggregated human globulin. *Clin. Exp. Immunol.* 43, 351-6, 1981.

Antibodies: A Laboratory Manual, Cold Spring Harbor Laboratory, 1988

Asghar, Pharmacological Manipulation of the complement system in human diseases. Front. Bioscience (On Line) 1, e15-26, 1996.

Ashkenazi and Chamow, Immunoadhesins as research tools and therapeutic agents. *Curr. Opin. Immunol.* 9, 195-200, 1997.

Berger et al., Immune complexes are potent inhibitors of interleukin-12 secretion by human monocytes. *Eur. J. Immunol.* 27, 2994-3000, 1997.

Bolhuis et al., Adoptive immunotherapy of ovarian carcinoma with bs-MAb-targeted lymphocytes: a multicenter study *Int J Cancer Suppl* 7, 78-81, 1992.

Brittenden et al., Natural Killer Cells and Cancer. *Cancer* 77, 1226-1243, 1996.

Capon et al., Designing CD4 immunoadhesins for AIDS therapy *Nature* 337, 525-31, 1989.

Cartron et al., Therapeutic activity of humanized anti-CD20 monoclonal antibody and polymorphism in IgG Fc receptor FcγRIIIa gene. *Blood* 99, 754-758, 2002.

Chamow and Ashkenazi, Immunoadhesins: principles and applications. *Trends Biotechnol.* 14, 52-60, 1996.

Clark et al., The potential of hybrid antibodies secreted by hybrid-hybridomas in tumour therapy *Int J Cancer Suppl* 2, 15-7, 1988.

Clynes et al., Uncoupling of immune complex formation and kidney damage in autoimmune glomerulonephritis. *Science* 279, 1052-4, 1998.

Clynes et al., Inhibitory Fc receptors modulate in vivo cytotoxicity against tumor targets. *Nat. Med.* 6, 443-446, 2000.

Cohen et al., *Bull. Rheum. Dis.*, 21:643, 1971.

Davis, M. T., et al., (1981) A conjugate of alpha-amanitin and monoclonal immunoglobulin G to Thy 1.2 antigen is selectively toxic to T lymphoma cells *Science* 213, 1385-8.

Dillman, R. O., et al., (1988) Superiority of an acid-labile daunorubicin-monoclonal antibody immunoconjugate compared to free drug *Cancer Res* 48, 6097-102.

Duncan, A. R., et al., (1988) Localization of the binding site for the human high-affinity Fc receptor on IgG. *Nature* 332, 563-4

Durandy, A., et al., (1981) Dysfunctions of pokeweed mitogen-stimulated T and B lymphocyte responses induced by gammaglobulin therapy. *J. Clin. Invest.* 67, 867-77.

Dwyer J. M.: Manipulating the immune system with immune globulins. New Engl. J. Med. 326, 107-16 (1992).

Edberg, J. C., and Kimberly, R. P. (1997) Cell type-specific glycoforms of Fc gamma RIIIa (CD16): differential ligand binding *J Immunol* 159, 3849-57

Edberg, J. C., et al., (1997) Analysis of FcgammaRII gene polymorphisms in Wegener's granulomatosis. *Exp Clin Immunogenet* 14, 183-95.

Edberg, J. C., et al., (1997) Cell type-specific glycoforms of Fc gamma RIIIa (CD16): differential ligand binding *J Immunol* 159, 3849-57.

Edwards et al., *Ann. Rheum. Dis.*, 46:773-6, 1987.

Eilat, D., et al., (1992) Secretion of a soluble, chimeric gamma delta T-cell receptor-immunoglobulin heterodimer *Proc Natl Acad Sci USA* 89, 6871-5.

EP 44167

Fanger, M. W., et al., (1992) Bispecific antibodies *Crit Rev Immunol* 12, 101-24.

Fazekas, F., et al., (1997) Randomised placebo-controlled trial of monthly intravenous immunoglobulin therapy in relapsing-remitting multiple sclerosis. *Lancet* 349, 589-93

Ferreri, N. R., et al., (1986) Release of leukotrienes C4 and B4 and prostaglandin E2 from human monocytes stimulated with aggregated IgG, IgA, and IgE *J Immunol* 136, 4188-93.

Foreign Patent Documents:

Fortis, C., et al., (1999) Dual role of TNF-α in NK/LAK cell-mediated lysis of chronically HIV-infected U1 cells. Concomitant enhancement of HIV expression and sensitization of cell-mediated lysis. *Eur. J. Immunol.* 29, 3654-3662.

Galfre, G., et al., (1981) Preparation of monoclonal antibodies: strategies and procedures *Methods Enzymol* 73, 3-46.

Galon, J., et al., (1997) Affinity of the interaction between Fc gamma receptor type III (Fc gammaRIII) and monomeric human IgG subclasses. Role of Fc gammaRIII glycosylation *Eur J Immunol* 27, 1928-32

Geha R. S. & F. S. Rosen: Intravenous immunoglobulin therapy. In: Therapeutic Immunology (Eds. Austen K. F., S. J. Burakoff, F. S. Rosen, T. B. Storm) Blackwell Science, Cambridge, Mass., pp. 280-296 (1996).

Gessner, J. E., et al., (1998) The IgG Fc receptor family. *Ann. Hematol.* 76, 231-48

Ghose, T., et al., (1982) Inhibition of a mouse hepatoma by the alkylating agent Trenimon linked to immunoglobulins *Cancer Immunol Immunother* 13, 185-9.

Ghose, T., et al., (1987) The design of cytotoxic-agent-antibody conjugates *Crit Rev Ther Drug Carrier Syst* 3, 263-359.

Glennie, M. J., et al., (1987) Preparation and performance of bispecific F(ab' gamma)2 antibody containing thioether-linked Fab' gamma fragments *J Immunol* 139, 2367-75.

Goldstein, G. (1987) Overview of the development of Orthoclone OKT3: monoclonal antibody for therapeutic use in transplantation *Transplant Proc* 19, 1-6.

Gomez-Guerrero, C., et al., (2000) Administration of IgG Fc fragments prevents glomerular injury in experimental immune complex nephritis. *J. Immunol.* 164, 2092-101

Gray, J. D., et al., (1994) The role of transforming growth factor beta in the generation of suppression: an interaction between CD8+ T and NK cells *J Exp Med* 180, 1937-42

Guyre, P. M., et al., (1997) Increased potency of Fc-receptor-targeted antigens *Cancer Immunol Immunother* 45, 146-8.

Harris, D. T., et al., (1989) Induction of activation antigens on human natural killer cells mediated through the Fc-gamma receptor. *J. Immunol.* 143, 2401-6

Hayes, R., et al., (2001) Adoptive cellular immunotherapy for the treatment of malignant gliomas. *Crit. Rev. Oncology/Hematology* 39, 31-42.

Hudson, P. J. (Opin Investig Drugs 2000 Jun) Recombinant antibodies: a novel approach to cancer diagnosis and therapy *Expert* 9, 1231-42.

Hulett, M. D., and Hogarth, P. M. (1994) Molecular basis for Fc receptor function. *Adv in Immunol.* 57, 1-127.

Jarvis, D. L., et al., (1996) Immediate-early baculovirus vectors for foreign gene expression in transformed or infected insect cells. *Protein Exp. Purif.* 8, 191-203

Johannesson et al., 1999, "Bicyclic tripeptide mimetics with reverse turn inducing properties." *J. Med. Chem.* 42:601-608.

Johnson, P., and Glennie, M. (2001) Rituximab: mechanisms and applications. *Brit. J Cancer* 85, 1619-1623.

Johnson et al., "Peptide Turn Mimetics," In: *Biotechnology and Pharmacy*, Pezzuto et al., eds., Chapman and Hall, New York, 1993.

Keler, T., et al., (Immunol Dec. 15, 2000) Targeting weak antigens to CD64 elicits potent humoral responses in human CD64 transgenic mice *J* 165, 6738-42.

Kroesen, B. J., et al., (1997) Approaches to lung cancer treatment using the CD3 x EGP-2-directed bispecific monoclonal antibody BIS-1 *Cancer Immunol Immunother* 45, 203-6.

Kurosaki, T., et al., (1991) A subunit common to an IgG Fc receptor and the T-cell receptor mediates assembly through different interactions *Proc Natl Acad Sci USA* 88, 3837-41

Kyte and Doolittle, "A simple method for displaying the hydropathic character of a protein," *J. Mol. Biol.,* 157(1): 105-132, 1982.

Laemmli, U. K. (1970) Cleavage of structural proteins during the assembly of the head of bacteriophage T4. *Nature* 227, 680-5

Lanier, L. L., et al., (1989) Co-association of CD3 zeta with a receptor (CD16) for IgG Fc on human natural killer cells *Nature* 342, 803-5

Lanier, L. L., et al., (1991) Molecular and functional analysis of human natural killer cell-associated neural cell adhesion molecule (N-CAM/CD56) *J Immunol* 146, 4421-6

LaSalle, J. M., et al. (1994) T cell anergy *Faseb J* 8, 601-8.

Legge, K. et al., (2000) Coupling of peripheral tolerance to endogenous interleukin 10 promotes effective modulation of myelin-activated T cells and ameliorates experimental allergic encephalomyelitis. *J. Exp. Med* 191, 2039-52

Lieberman, J. D., *Rheum. Dis. Clin. North. Am.,* 14:223-243, 1988

Liu, C., et al., (1996) F(c)gammaRI-targeted fusion proteins result in efficient presentation by human monocytes of antigenic and antagonist T cell epitopes *J Clin Invest* 98, 2001-7.

Liu, C., et al., (1996) Fc gamma RII on human B cells can mediate enhanced antigen presentation *Cell Immunol* 167, 188-94.

Lord, J. M., et al., (1992) Cell surface and intracellular functions for galactose binding in ricin cytotoxicity *Biochem Soc Trans* 20, 734-8.

Lord, J. M., et al., (1992) Chimeric proteins containing ricin A chain *Targeted Diagn Ther* 7, 183-90.

Lubbe et al., *Lancet,* 1361-1363, 1983.

Lund, J., et al. (1991) Human Fc gamma RI and Fc gamma RII interact with distinct but overlapping sites on human IgG. *J. Immunol.* 147, 2657-62

Majeau, G. R., et al., (1994) Mechanism of lymphocyte function-associated molecule 3-Ig fusion proteins inhibition of T cell responses. Structure/function analysis in vitro and in human CD2 transgenic mice *J Immunol* 152, 2753-67.

Manabe, Y., et al., (1984) Production of a monoclonal antibody-methotrexate conjugate utilizing dextran T-40 and its biologic activity *J Lab Clin Med* 104, 445-54.

Marks, J. D., et al., (1991) By-passing immunization. Human antibodies from V-gene libraries displayed on phage *J Mol Biol* 222, 581-97.

McCarroll, L., and King, L. A. (1997) Stable insect cell cultures for recombinant protein production. *Curr. Opin. Biotechnol.* 8, 590-4

McLean, G., et al., (2000) Human and murine immunoglobulin expression vector cassettes. *Mol. Immunol.* 37, 837-845.

Menard, S., et al., (1989) Hybrid antibodies in cancer diagnosis and therapy *Int J Biol Markers* 4, 131-4.

Meyerson, H. J., et al., (1996) Functional dissociation of CD8 alpha's Ig homologue and connecting peptide domains *J. Immunol.* 156, 574-84

Meyerson, H. J., et al., (1996) Functional dissociation of CD8 alpha's Ig homologue and connecting peptide domains *J Immunol* 156, 574-84.

Miller, K. L., et al., (1996) A novel role for the Fc receptor gamma subunit: enhancement of Fc gamma R ligand affinity *J Exp Med* 183, 2227-33

Miller, M. L., *Curr. Opin. Rheum.,* 4:693-699, 1992.

Miyagi, F., et al., (1997) Fc portion of intravenous immunoglobulin suppresses the induction of experimental allergic neuritis. *J. Neuroimmunol.* 78, 127-31

Moingeon, P., et al., (1992) CD3 zeta dependence of the CD2 pathway of activation in T lymphocytes and natural killer cells *Proc Natl Acad Sci USA* 89, 1492-6

Morgan, A., et al., (1995) The N-terminal end of the CH2 domain of chimeric human IgG1 anti-HLA-DR is necessary for C1q, Fc gamma RI and Fc gamma RIII binding. *Immunology* 86, 319-24

Morgan, B. P. (2000) The complement system: an overview. *Mol Biol Methods* 150, 1-13.

Morrison, S. L., et al., (1986) Production of novel immunoglobulin molecules by gene transfection *Mt Sinai J Med* 53, 175-80.

Nagler, A., et al., (1990) Constitutive expression of high affinity interleukin 2 receptors on human CD16-natural killer cells in vivo. *J. Exp. Med.* 171, 1527-33

Nelson, H. (1991) Targeted cellular immunotherapy with bifunctional antibodies *Cancer Cells* 3, 163-72.

Nitta, T., et al., (1990) Induction of cytotoxicity in human T cells coated with anti-glioma x anti-CD3 bispecific antibody against human glioma cells *J Neurosurg* 72, 476-81.

Nolan, O., et al., (1990) Bifunctional antibodies: concept, production and applications *Biochim Biophys Acta* 1040, 1-11.

Norderhaug, L., et al., (1997) Versatile vectors for transient and stable expression of recombinant antibody molecules in mammalian cells. *J. Immun. Meth.* 204, 77-87

Ogata, M., et al., (1990) Processing of Pseudomonas exotoxin by a cellular protease results in the generation of a 37,000-Da toxin fragment that is translocated to the cytosol *J Biol Chem* 265, 20678-85.

Ohtsuka, K., et al., (1998) Decreased production of TGF-beta by lymphocytes from patients with systemic lupus erythematosus *J Immunol* 160, 2539-45

Passwell, J. H., et al., (1979) Increased prostaglandin production by human monocytes after membrane receptor activation *J Immunol* 123, 115-20.

Perez, P., et al., (1985) Specific targeting of cytotoxic T cells by anti-T3 linked to anti-target cell antibody *Nature* 316, 354-6.

Perez, P., et al., (1986) Specific lysis of human tumor cells by T cells coated with anti-T3 cross-linked to anti-tumor antibody *J Immunol* 137, 2069-72.

Pfeifer, T. A. (1998) Expression of heterologous proteins in stable insect cell culture. *Curr. Opin. Biotechnol.* 9, 518-21

Pietersz, G. A., et al., (1988) Immunochemotherapy of a murine thymoma with the use of idarubicin monoclonal antibody conjugates *Cancer Res* 48, 926-31

Pietersz, G. A., et al., (1988) Specific in vitro anti-tumour activity of methotrexate-monoclonal antibody conjugates prepared using human serum albumin as an intermediary *Immunol Cell Biol* 66, 43-9.

Ptak, W., et al., (2000) Heat-aggregated immunoglobulins increase in vivo immunogenicity of mouse hapten (TNP)-derivatized macrophages by upregulation of interleukin-12 secretion and expression of B7-1 and B7-2 costimulatory molecules. *Scand. J. Immunol.* 51, 479-84

Raghavan, M., and Bjorkman, P. J. (1996) Fc receptors and their interactions with immunoglobulins. *Ann. Rev. Cell. Dev. Biol.* 12, 181-220

Remington's Pharmaceutical Sciences, 18th Ed. Mack Printing Company, 1990.

Rosenstein, M., et al., (1984) Lymphokine-activated killer cells: lysis of fresh synergic natural killer-resistant murine tumor cells by lymphocytes cultured in interleukin-2. *Cancer Res.* 44, 1949-1953.

Shields, R. L., et al., (2001) High resolution mapping of the binding site on human IgG1 for FcγRI, FcγRII, FcγRIII, and FcRn and design of IgG1 variants with improved binding to the FcγR. *J. Biol. Chem.* 276, 6591-6604.

Silman et al., *Ann. Rheum. Dis.*, 47:988-92, 1988.

Sondermann, P., et al., (2000) The 3.2-Å crystal structure of the human IgG1 Fc fragment-FcγRIII complex. *Nature* 406, 267-273.

Sorensen, P. S., et al., (1998) Intravenous immunoglobulin G reduces MRI activity in relapsing multiple sclerosis *Neurology* 50, 1273-81.

Staerz, U. D., et al., (1985) Hybrid antibodies can target sites for attack by T cells *Nature* 314, 628-31.

Steinberg and Steinber, *Arthritis. Rheum.*, 34:945-950, 1991.

Swain, S. L., et al. (1988) The role of IL4 and IL5: characterization of a distinct helper T cell subset that makes IL4 and IL5 (Th2) and requires priming before induction of lymphokine secretion *Immunol Rev* 102, 77-105.

Ting, C. C., et al., (1988) Augmentation by anti-T3 antibody of the lymphokine-activated killer cell-mediated cytotoxicity *J Immunol* 141, 741-8.

Traunecker, A., et al., (1989) Highly efficient neutralization of HIV with recombinant CD4-immunoglobulin molecules *Nature* 339, 68-70.

U.S. Pat. No. 4,196,265
U.S. Pat. No. 4,340,535
U.S. Pat. No. 4,554,101
U.S. Pat. No. 4,658,019
U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,714,147
U.S. Pat. No. 5,830,731
U.S. Pat. No. 5,840,833
U.S. Pat. No. 5,859,184
U.S. Pat. No. 5,922,845
U.S. Pat. No. 5,929,237
U.S. Pat. No. 5,998,166
U.S. Pat. No. 6,046,310

Vaickus, L., et al., (1991) Overview of monoclonal antibodies in the diagnosis and therapy of cancer *Cancer Invest* 9, 195-209.

Venables, P. J. W., *British Medical Journal,* 307:663-666, 1993.

Vita et al., 1998, "Novel miniproteins engineered by the transfer of active sites to small natural scaffolds." *Biopolymers* 47:93-100.

Vivier, E., et al., (1991) CD2 is functionally linked to the zeta-natural killer receptor complex *Eur J Immunol* 21, 1077-80

Volk, H. D., et al., (1986) Suppression of the local graft-vs.-host reaction in rats by treatment with a monoclonal antibody specific for the interleukin 2 receptor *Eur J Immunol* 16, 1309-12.

Vyse and Walport, *Br. F Hosp. Med.,* 50:121-132, 1993.

Wallace, D. J., et al., (1993) The relevance of antimalarial therapy with regard to thrombosis, hypercholesterolemia and cytokines in SLE *Lupus* 2 Suppl 1, S13-5.

Weisshoff et al., "Mimicry of beta II'-turns of proteins in cyclic pentapeptides with one and without D-amino acids." *Eur. J. Biochem.* 259:776-788, (1999).

White, D. M., et al., (2001) Design and Expression of Polymeric Immunoglobulin Fusion Proteins: A Strategy for Targeting Low-Affinity Fc Receptors. *Protein Expression and Purification* 21, 446-455

Wiesenhutter, C., et al., (1984) IgG aggregates of different sizes stimulate or suppress Ig secretion by human lymphocytes in vitro. *J. Clin. Immunol.* 4, 124-33

Wilke et al., (1991) *Clin. Exp. Rheumatol,* 9:581-587,.

Winter, G., et al., (1991) Man-made antibodies *Nature* 349, 293-9.

WO9942077

Wu, J., et al., (1997) A novel polymorphism of FcgammaRIIIa (CD16) alters receptor function and predisposes to autoimmune disease *J Clin Invest* 100, 1059-70.

Wunderlich, J. R., et al., (1992) Bispecific antibodies and retargeted cellular cytotoxicity: novel approaches to cancer therapy *Int J Clin Lab Res* 22, 17-20.

Young, et al., "Influence of immunoglobulin heavy- and light-chain expression on B-cell differentiation," *Genes Develop.,* 8:1043-1057, 1994.

Zaghouani, H., et al., (1993) Presentation of a viral T cell epitope expressed in the CDR3 region of a self immunoglobulin molecule *Science* 259, 224-7.

Zanetti, M., et al., (1992) Theoretical and practical aspects of antigenized antibodies *Immunol Rev* 130, 125-50.

What is claimed is:

1. A polypeptide with an immunoglobulin framework consisting of an Fc region linked to two arms;
wherein
each arm consists of an HCH2 polymer linked to a protein or portion thereof;
the HCH2 polymer consists of two to six linear copies of an HCH2 monomer;
the HCH2 monomer consists of at least a portion of an HCH2 region of human IgG1 or at least a portion of an HCH2 region of human IgG3, wherein the at least a portion of an HCH2 region of human IgG1 and the at least a portion of an HCH2 region of human IgG3 include a hinge region;
at least one hinge region cysteine of the HCH2 monomer is mutated to serine; and
the polypeptide targets to cells expressing low affinity FcγR, or binds to low affinity FcγR.

2. The polypeptide of claim 1, wherein the HCH2 monomer targets to and/or binds to the same receptor as the Fc region.

3. The polypeptide of claim 1, wherein the HCH2 monomer comprises at least SEQ ID NO: 9.

4. The polypeptide of claim 1, wherein the HCH2 monomer comprises at least SEQ ID NO: 10 and wherein the at least one hinge region cysteine to serine mutation occurs in at least one of the hinge cysteines in SEQ ID NO: 10.

5. The polypeptide of claim 1, wherein the HCH2 monomer comprises at least SEQ ID NO: 10 and wherein the at least one hinge region cysteine to serine mutation occurs in the three hinge cysteines in SEQ ID NO: 10.

6. The polypeptide of claim 1, wherein the protein or portion thereof is selected from the group consisting of: HSA, domain I of HSA (SEQ ID NO: 11), domain II of HSA (SEQ ID NO: 12), domain III of HSA (SEQ ID NO: 13), CD8α, CD8β, and CD8.

7. The polypeptide of claim 1, wherein the protein or portion thereof is domain I of HSA (SEQ ID NO: 11).

8. The polypeptide of claim 1, wherein the protein or portion thereof comprises at least a portion of a sequence selected from the group consisting of a CD8α, an HSA, and a transporter protein.

9. The polypeptide of claim 1, wherein the protein or portion thereof comprises at least a portion of a sequence from HSA.

10. The polypeptide of claim 1, wherein the protein or portion thereof comprises at least a portion of a sequence from myelin basic protein.

11. The polypeptide of claim 1, wherein the protein or portion thereof comprises at least a portion of a sequence from proteolipid protein.

12. The polypeptide of claim 1, wherein the protein or portion thereof comprises one or more of a soluble protein domain, a transporter protein domain, a ligand binding domain, or a cell surface receptor domain.

13. The polypeptide of claim 1, wherein the protein or portion thereof comprises at least a portion of a protein selected from the group consisting of a toxin antigen sequence, a viral antigen sequence, and a tumor antigen sequence.

14. The polypeptide of claim 1, wherein the polypeptide is soluble in aqueous solution.

15. The polypeptide of claim 1, wherein the polypeptide is between 26 kDa and 1500 kDa.

16. The polypeptide of claim 1, wherein the polypeptide is between 45 kDa and 600 kDa.

17. The polypeptide of claim 1, wherein the HCH2 polymer consists of two to six linear copies of the HCH2 monomer and wherein the HCH2 monomer consists of an HCH2 region of human IgG1.

18. The polypeptide of claim 1, wherein the HCH2 polymer consists of three to four linear copies of the HCH2 monomer and wherein the HCH2 monomer consists of an HCH2 region of human IgG1.

19. The polypeptide of claim 1, wherein the polypeptide is adapted for use as a vaccine.

20. The polypeptide of claim 1, wherein the HCH2 polymer consists of two to four linear copies of the HCH2 monomer and the protein or portion thereof comprises a CD8α polypeptide.

21. The polypeptide of claim 1, wherein the HCH2 polymer consists of two to four linear copies of the HCH2 monomer and the protein or portion thereof comprises domain I of HSA.

22. The polypeptide of claim 1, wherein the polypeptide induces proliferation of PBMCs with greater potency than aggregated IgG.

23. The polypeptide of claim 1, wherein the hinge region cysteines of all copies of the HCH2 monomer are mutated to serine.

24. A polypeptide with an immunoglobulin framework consisting of an Fc region linked to two arms;
wherein
each arm consists of an HCH2 polymer linked to domain I of HSA (SEQ ID NO: 11);
the HCH2 polymer consists of four linear copies of an HCH2 monomer;
the HCH2 monomer consists of at least a portion of an HCH2 region of human IgG1, wherein the at least a portion of an HCH2 region of human IgG1 includes a hinge region;
the hinge region cysteines of the HCH2 monomer are mutated to serine; and
the polypeptide targets to cells expressing low affinity FcγR, and/or binds to low affinity FcγR.

* * * * *

SEQUENCE LISTING

<160> NUMBER OF SEQ ID NOS: 13

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ggccgctaaa gcttgagccc aaatcttgtg acaaaactc                              39

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ggccgctagt cgactcattt acccggagac agggagag                               38

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cccgtagaat tcgagcccaa atcttctgac aaaactcaca catccccacc gtcccca          57

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ggccgcataa gcttggagcc tcgcgatttg gctttggaga tggttttctc                  50

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggccgcatcc cggggagccc aaatcttctg acaaaact                               38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6

-continued

```
ggccgcataa gcttttggc tttggagatg gttttctc                                    38
```

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7

```
ggccgctact cgagatggcc ttaccagtga ccgccttg                                   38
```

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8

```
ggccgctaga attccgtcgt ggtgggcttc gctggcag                                   38
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Glu Leu Leu Gly Gly Pro Ser
1               5

<210> SEQ ID NO 10
<211> LENGTH: 125
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys
        115                 120                 125

<210> SEQ ID NO 11
<211> LENGTH: 197
<212> TYPE: PRT
<213> ORGANISM: human

<400> SEQUENCE: 11

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Gly Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg
        195
```

<210> SEQ ID NO 12
<211> LENGTH: 198
<212> TYPE: PRT
<213> ORGANISM: human

<400> SEQUENCE: 12

```
Glu Gly Lys Ala Ser Ser Ala Lys Gln Arg Leu Lys Cys Ala Ser Leu
1               5                   10                  15

Gln Lys Phe Gly Glu Arg Ala Phe Lys Ala Trp Ala Val Ala Arg Leu
            20                  25                  30

Ser Gln Arg Phe Pro Lys Ala Glu Phe Ala Glu Val Ser Lys Leu Val
        35                  40                  45

Thr Asp Leu Thr Lys Val His Thr Glu Cys Cys His Gly Asp Leu Leu
    50                  55                  60

Glu Cys Ala Asp Asp Arg Ala Asp Leu Ala Lys Tyr Ile Cys Glu Asn
65                  70                  75                  80

Gln Asp Ser Ile Ser Ser Lys Leu Lys Glu Cys Cys Glu Lys Pro Leu
                85                  90                  95

Leu Glu Lys Ser His Cys Ile Ala Glu Val Glu Asn Asp Glu Met Pro
            100                 105                 110

Ala Asp Leu Pro Ser Leu Ala Ala Asp Phe Val Glu Ser Lys Asp Val
        115                 120                 125

Cys Lys Asn Tyr Ala Glu Ala Lys Asp Val Phe Leu Gly Met Phe Leu
```

```
            130                 135                 140

Tyr Glu Tyr Ala Arg Arg His Pro Asp Tyr Ser Val Val Leu Leu Leu
145                 150                 155                 160

Arg Leu Ala Lys Thr Tyr Glu Thr Thr Leu Glu Lys Cys Cys Ala Ala
                165                 170                 175

Ala Asp Pro His Glu Cys Tyr Ala Lys Val Phe Asp Glu Phe Lys Pro
            180                 185                 190

Leu Val Glu Glu Pro Gln
        195

<210> SEQ ID NO 13
<211> LENGTH: 205
<212> TYPE: PRT
<213> ORGANISM: human

<400> SEQUENCE: 13

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Glu Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu
        195                 200                 205
```